US005871753A

United States Patent [19]
Crabtree et al.

[11] Patent Number: 5,871,753
[45] Date of Patent: Feb. 16, 1999

[54] REGULATED TRANSCRIPTION OF TARGETED GENES AND OTHER BIOLOGICAL EVENTS

[75] Inventors: Gerald R. Crabtree, Woodside, Calif.; Stuart L. Schreiber, Boston, Mass.; David M. Spencer, Los Altos, Calif.; Thomas J. Wandless, Cambridge; Peter Belshaw, Somerville, both of Mass.; Steffan Ho, Menlo Park, Calif.

[73] Assignees: Board of Trustees of the Leland Stanford Junior University, Palo Alto, Calif.; President and Fellows of Harvard College, Cambridge, Mass.

[21] Appl. No.: 473,985

[22] Filed: Jun. 7, 1995

Related U.S. Application Data

[60] Division of Ser. No. 179,748, Jan. 7, 1994, abandoned, which is a continuation-in-part of Ser. No. 92,977, Jul. 16, 1993, abandoned, which is a continuation-in-part of Ser. No. 17,931, Feb. 12, 1993, abandoned.

[51] Int. Cl.$^6$ .......................... A61K 45/00; A61K 38/13; C07K 5/12; C07D 491/06
[52] U.S. Cl. ........................ 424/280.1; 530/317; 514/27; 514/183
[58] Field of Search ........................ 424/280.1; 435/183; 530/317; 514/27, 183

[56] References Cited

U.S. PATENT DOCUMENTS

| 5,120,727 | 6/1992 | Kao et al. ................................ 540/456 |
| 5,162,333 | 11/1992 | Failli et al. ............................. 514/291 |
| 5,171,671 | 12/1992 | Evans et al. ........................... 435/69.1 |

FOREIGN PATENT DOCUMENTS 23550 11/1993 WIPO.

OTHER PUBLICATIONS

Irving and Weiss, "The Cytoplasmic Domain of the T Cell Receptor ζ Chain is Sufficient to Couple to Receptor–Associated Signal Transduction Pathways"; *Cell* 64:891–901 (1991).

Kinet, "Antibody–Cell Interactions: Fc Receptors"; *Cell* 57:351–354 (1989).

Orloff et al., "Family of Disulphide–Linked Dimers Containing the ζ and η Chains of the T–Cell Receptor and the γ Chain of Fc Receptors"; *Nature* 347:189–191 (1990).

Durand et al., "Characterization of Antigen Receptor Response Elements Within the Interleukin–2 Enhancer"; *Mol. Cell Biol.* 8(2):1715–1724 (1988).

Letourneur and Klausner, Activation of T Cells by a Tyrosine Kinase Activation Domain in the Cytoplasmic Tail of CD3 ε; *Science* 255:79–82 (1992).

Flanagan et al., "Nuclear Association of a T–Cell Transcription Factor Blocked by FK–506 and Cyclosporin A"; *Nature* 352:803–807 (1991).

Byrn et al., "Biological Properties of a CD4 Immunoadhesin"; *Nature* 344:667–670 (1990).

Lanier et al., "Co–association of CD3ζ with a Receptor (CD16) for IgG Fc on Human Natural Killer Cells"; *Nature* 342:803–805 (1989).

Mattila et al., "The Actions of Cyclosporin A and FK506 Suggest a Novel Step in the Activation of T Lymphocytes"; *EMBO J.* 9(13):4425–4433 (1990).

Verweij et al., "Cell Type Specificity and Activation Requirements for NFAT–1 (Nuclear Factor of Activated T–Cells) Transcriptional Activity Determined by a New Method Using Transgenic Mice to Assay Transcriptional Activity of an Individual Nuclear Factor"; *J. Biol. Chem.* 265(26):15788–15795 (1990).

Clark et al., "The B Cell Antigen Receptor Complex: Association of Ig–α and IG–β with Distinct Cytoplasmic Effectors"; *Science* 258:123–126 (1992).

Shaw et al., "Identification of a Putative Regulator of Early T Cell Activation Genes"; *Science* 241:202–205 (1988).

Weissman et al., "Molecular Cloning and Chromosomal Localization of the Human T–Cell Receptor ζ Chain: Distinction from the Molecular CD3 Complex"; *Proc. Natl. Acad. Sci. USA* 85:9709–9713 (1988).

Emmel et al., "Cyclosporin A Specifically Inhibits Function of Nuclear Proteins Involved in T–Cell Activation"; *Science* 246:1617–1620 (1989).

Eberle and Nuninger, "Synthesis of the Main Metabolite (OL–17) of Cyclosporin A"; *J. Org. Chem.* 57:2689–2691 (1992).

Traber et al., "Cyclosporins –New Analogues by Precursor Directed Biosynthesis"; *J. Antibiotics* 42:591–597 (1989).

Patchett et al., "Analogs of Cyclosporin A Modified at the D–ALA$^8$ Position"; *J. Antibiotics* 45:94–102 (1992).

Donald et al., "C10 N–Acyl Modified FK–506: A Possible Hybrid Analogue of the Transition State of Peptidyl–Prolyl Cis–Trans Isomerization"; *Tetrahedron Letters* 31:1375–1378 (1991).

(List continued on next page.)

*Primary Examiner*—James Ketter
*Assistant Examiner*—William Sandals
*Attorney, Agent, or Firm*—Matthew P. Vincent; Isabelle M. Clauss; David L. Berstein, Esq.

[57] ABSTRACT

Methods and compositions are provided for modified cells, where a chimeric protein consisting of a ligand binding domain fused to an action domain is employed which initiates a signal which activates a biological process: transcription of at least one gene, usually a second construct introduced into the host cells; exocytosis; or an extracellular process. The second construct optimally present provides for a promoter which responds to a transcriptional activation action domain to provide for transcription, when an appropriate ligand binds to the ligand binding domain. Exemplary of the system is the use of an FKBP/CD3ζ or transcription factor fusion protein, using dimeric FK506 or FK520 as the ligand and a promoter responsive to NF-AT or other transcription factor requiring two molecules for transcriptional activation.

35 Claims, 22 Drawing Sheets

OTHER PUBLICATIONS

Nussbaumer et al., C9–Imino and C10–Amino Derivatives of Ascomycin (21–Ethyl–FK506); *Tetrahedron Letters* 33:3845–3846 (1992).

Evans et al., "Rhodium(I)–and Iridium(I)–Catalyzed Hydroboration Reactions: Scope and Synthetic Applications"; *J. Am. Chem. Soc.* 114:6671–6679 (1992).

Evans et al., "Mechanistic Study of the Rhodium(I)–Catalyzed Hydroboration Reaction"; *J. Am. Chem. Soc.* 114:6679–6685 (1992).

Ghosh et al., "N,N'–Disuccinimidyl Carbonate: A Useful Reagent for Alkoxycarbonylation of Amines"; *Tetrahedron Letters* 33:2781–2784 (1992).

Zelle et al., "A Systematic Degradation of Zincophorin: A Stereoselective Synthesis of the $C_{17}$–$C_{25}$ Fragment"; *J. Org. Chem.* 51:5032–5036 (1986).

Krishnamurthy, "Lithium Tris[(3–ethyl–3–pentyl)oxy]aluminum Hydride. A New Remarkably Chemoselective Reagent for the Reduction of Aldehydes in the Presence of Ketones"; *J. Org. Chem.* 46:4628–4629 (1981).

Fisher et al., "On the Remarkable Propensity for Carbon–Carbon Bond Cleavage Reactions in the $C_8$–$C_{10}$ Region of FK–506"; *J. Org. Chem.* 56:2900–2907 (1991).

VanRheenen et al., "An Improved Catalytic $OsO_4$ Oxidation of Olefins to Cis–1,2–Glycols Using Tertiary Amine Oxides as the Oxidant"; *Tetrahedron Letters* 23:1973–1976 (1976).

Fields, S. and Song, O., "A novel genetic system to detect protein–protein interactions"; *Nature* 340:245–246 (1989).

Schreiber, "Chemistry and Biology of the Immunophilins and Their Immuno–suppressive Ligands", *Science* 251:283–287 (1991).

Palmiter et al., "Transgenic Mice", *Cell* 41:343–345 (1985).

Itoh et al., "Effect of bcl–2 on Fas Antigen–Mediated Cell Death", *Journal of Immunology* 151:621–627 (1993).

Itoh and Nagata, "A Novel Protein Domain Required for Apoptosis", JBC 268:10932–10937 (1993).

Ptashne et al., "Activators and Targets", *Nature* 346:329–331 (1990).

Construction of intracellular signalling chimera:

1. PCR myristoylated CD3ζ

2. Cut and clone PCR fragment

*The MZE series contains a 9aa HA epitope at the 3' end.

3. SEQUENCE insert

4. Cut at XhoI or SalI and add FKBP domains

Construction of extracellular signaling chimera:

1. PCT murine signal peptide

2. PCT CD3 trans-membrane and cytoplasmic domains

Tζζ pBluescript plasmid #SPZ/KS
SEQUENCE insert*

Cut XhoI

CYCC

```
                          XhoI        homology
6568:    5'-CGACACTCGAGGTGACGGACAAGGTC-3'

SalI        homology
6569:    5'-CGACAGTCGACCCAATCAGGGACCTC-3'
```

EPITOPE

```
                   XhoI       BsiWI
7850:    5'-TCGAGTATCCGTACGACGTACCAGACTACGCAG-3'
                 Y   P   Y   D   V   P   D   Y   A

SalI
7851:    5'-TCGACTGCGTAGTCTGGTACGTCGTACGGATAC-3'
```

EPITOPE: 5SEP, 3XEP

```
                   SalI
8922:    5'-TCGACTATCCGTACGACGTACCAGACTACGCAC-3'

XhoI
8923:    5'-TCGAGTGCGTAGTCTGGTACGTCGTACGGATAG-3'
```

Myristoylation from c-src 5SMXZ

```
                   SacII                Myristoylation Signal
8908:    5'-CGACACCGCGGCCACCATGGGGAGTAGCAAGAGCAAGCCT
                         KOZAK M   G   S   S   K   S   K   P XhoI      ζ-homology
         AAGGACCCCAGCCAGCGCCTCGAGAGGAGTGCAGAGACTG-3'
          K   D   P   S   Q   R   L   E   R   S   A   E   T
```

5XTZ

Tac | CD3ζ

```
                   XhoI      homology
8912:    5'-CGACACTCGAGGAGCTCTGTGACGATG-3'
                              E   L   C   D   D
```

FIG. 4B

Scheme 2: Synthesis of Dimers 1) 2M NH3 / MeOH
2) formic acid / acetic anhydride or acetic anhydride SeO2

Lit ref: N.H. Sigal & F.J. Dumont, Ann. Rev. Immunol. p519 1992

Lit refs: D.K. Donald et.al. Tetrahedron Letters p1375, 1991, P.Kocovsky, Tetrahedron Letters p5521, 1992

N,N'-Disuccinimidyl carbonate, Et3N, CH3CN

An additional modified FK520 (FK1040) that interferes with FKBP12 yet should bind the FKBP12 mutant: F36A or F99A or Y26A, or combinations thereof is Scheme 3

REGULATED TRANSCRIPTION OF TARGETED GENES AND OTHER BIOLOGICAL EVENTS

CROSS-REFERENCE TO RELATED APPLICATIONS

This is a divisional of application Ser. No. 08/179,748, filed Jan. 7, 1994 now abandoned, which is a continuation-in-part of application of U.S. Ser. No. 092,977, filed Jul. 16, 1993 now abandoned, which in turn is a continuation-in-part application of U.S. Ser. No. 08/017,931, filed Feb. 12, 1993 now abandoned, the contents of each application are incorporated by reference into the present disclosure.

STATEMENT OF RIGHTS

This invention was made in the course of work supported by the U.S. Government. The U.S. Government therefore has certain rights in the invention.

TECHNICAL FIELD

The field of this invention is the oligomerizing of chimeric proteins with a dimeric non-peptidic organic molecule, in part, exemplified by recombinant modifications of host cells, finding application in gene therapy or other applications of inducible transcription in transduced cells.

BACKGROUND

The genomic complexity of mammals, particularly humans, allows for numerous genetic and physiological changes during conception, development of the fetus, and during adult life. Subsequently, pathologic changes may occur, due to autoimmune diseases, exposure to mutating agents, and the like. In addition, there are various recessive genes, which can result in diseases when the resulting progeny is homozygous for the recessive trait. For the most part, individuals having a variety of genetic diseases or pathological indications associated with autoimmune diseases, such as diabetes, have, for the most part, been dependent upon the administration of drugs. Drugs have not been entirely satisfactory for a number of different reasons. Frequently, the drugs have side effects which are detrimental to the host and result in pathological events. For some diseases, drugs are merely palliative or nay not even be available. In other situations, regular administration of drugs can be difficult to maintain, particularly with the elderly or mentally impaired, who find it difficult to perform a strict regimen.

With The advent of recombinant technology, the possibility of modifying endogenous cells or cells which can be safely administered to a host has offered new avenues of investigation for therapeutic treatments. However, there are many concerns related to the use of gene therapy. In some cases, one is solely concerned with introducing cells into the host which can function in place of defective wild-type cells. In other situations, one may wish to provide cells which can produce a secreted product which can then fulfill a desired function. However, in normal physiological operation, the secretion of product is usually controlled based on need and, frequently, may involve providing a localized concentration of the secreted product, rather than a systemic availability. It is therefore of substantial interest to be able to develop gene therapies, which can meet manifold therapeutic needs as required by the sick and impaired.

The levels of production of proteins by human cells varies by as much as 1 to $10^6$ fold during development and in response to physiologic and pathologic stimuli. (E. H. Davidson, Gene Activity in Development 1986, 3rd Edition, Academic Press, Orlando, Fla.) Since any protein if overexpressed nay have toxic and harmful effects, it is essential that any introduced gene be carefully regulated.

Furthermore, there is usually a minimum level of therapeutic effect. By monitoring the level of the protein product in the tissue, organ or vascular system, in a system subject to extrinsic control, one can determine the level of the protein product, and use the extrinsic control to provide the desired level.

Besides intracellular opportunities for therapy, there are also possibilities where control of extracellular events may be of interest. In a variety of situations, such as homing, blood coagulation, clot dissolution, cell activation, and the like, the ability to bring together two or more different proteins rapidly could provide for new opportunities for controlling physiology and therapies.

RELEVANT LITERATURE

Clark, et al., Science (1992) 258, 123 describe cytoplasmic effectors of the B-cell antigen receptor complex. Durand, et al., Mol. Cell. Biol. (1988) 8, 1715, Verweij, et al., J. Biol. Chem. (1990) 265, 15788 and Shaw, et al., Science (1988) 241, 202 report that the NF-AT-directed transcription is rigorously under the control of the antigen receptor. Inhibition of NF-AT-directed transcription by cyclosporin A and FK506 is reported by Emmel, et al., Science (1989) 246, 1617 and Flanagan, et al., Nature (1991) 352, 803. Durand, et al., Mol. Cell. Biol. (1988) 8, 1715 and Mattila, et al., EMBO J. (1990) 9, 4425 describe the NF-AT binding sites. References describing the ζ chain include Orloff, et al., Nature (1990) 347, 189–191; Kinet, et al., Cell (1989) 57, 351–354; Weissman, et al., Proc. Natl. Acad. Sci. USA (1988) 85, 9709–9713 and Lanier, Nature (1989) 342, 803–805. A CD4 immunoadhesin is described by Byrn, et al. Nature (1990) 44, 667–670. A CD8-ζ-fused protein is described by Irving, et al., Cell (1992) 64, 891. See also, Letourner and Klausner, Science (1992) 255, 79.

Illustrative articles describing transcriptional factor association with promoter regions and the separate activation and DNA binding of transcription factors include: Keegan et al., Nature (1986) 231, 699; Fields and Song, ibid (1989) 340, 245; Jones, Cell (1990) 61, 9; Lewin, Cell (1990) 61, 1161; Ptashne and Gann, Nature (1990) 346, 329; Adams and Workman, Cell (1993) 72, 306.

Illustrative articles describing vesicle targeting and fusion include: Sollner at al. (1993) Nature 362, 318–324, and Bennett and Scheller (1993) Proc. Natl. Acad. Sci. USA 90, 2559–2563.

SUMMARY OF THE INVENTION

Novel chimeric proteins and small organic molecules capable of oligomerizing the chimeric proteins are provided. Genes encoding the novel chimeric proteins, and optionally target genes, are provided for introduction into cells resulting in a modified genome and phenotype. Also provided are methods and compositions for producing and using the cells. The cells are characterized by having at least one chimeric-r-used protein capable of causing a cellular event, optionally, a first series of constructs expressing the chimeric protein(s), and an optionally second or second series of construct(s) expressing one or more transcripts which are under the transcriptional control of a signal which results from oligomerization of said chimeric-fused membrane protein upon binding to an appropriate ligand. Particularly, the cells find use in gene therapy.

Alternatively, the chimeric fused proteins and oligomerizing molecules may be used extracellularly to bring together proteins which act in concert to initiate a physiological action.

BRIEF DESCRIPTION OF THE FIGURES

FIGS. 4A, 4B and 4C are sequences of the primers (SEQ ID NOS. 4 through 40) used in the constructions or the plasmids employed in the subject invention.

FIGS. 3A and 9D are the chemical structures of the allyl-linked FK506 variants and the cycloboxyl-linked FK506 variants, respectively.

DESCRIPTION OF THE SPECIFIC EMBODIMENTS

I. Generic Discussion

Figure 1:
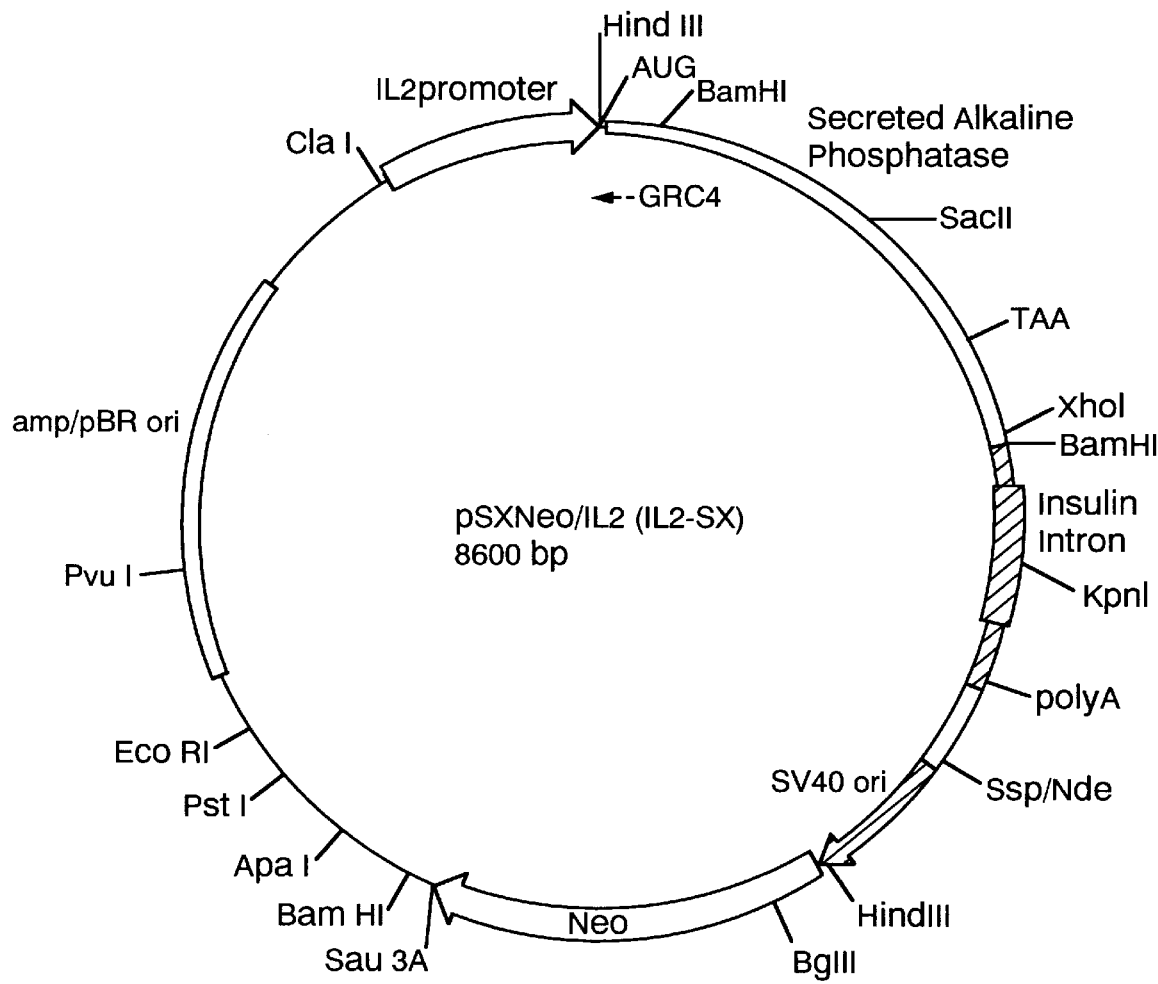
FIG. 1 is diagram of the plasmid pSXNeo/IL2 (IL2-SX) and NF-AT-SX.

A system is provided using a combination of chimeric fused proteins and small organic molecules for oligomerizing the chimeric fused proteins. The fused proteins have a binding domain for binding to the small organic oligomerizing molecules and an action domain, which can effectuate a physiological action as a result of oligomerization of the chimeric fused proteins. (By physiological action is intended a change in state, such as a physical state, e.g. conformational change, change in binding partner, cell death, initiation of transcription, channel opening, ion release, e.g. $Ca^{+2}$ etc. or a chemical state, such as a chemical reaction, e.g. acylation, methylation, hydrolysis, phosphorylation or dephosphorylation, change in redox state, rearrangement, or the like.) For intracellular chimeric fused proteins, a cellular targeting sequence (include organelle targeting amino acid sequences) will also be present.

As a first application of the subject invention, cells are modified so as go be responsive to the oligomerizing molecules. The cells may find use in gene therapy, as well as other applications where inducible transcription or translation (both are included under the term expression) is desired. The cells are characterized by having at least a first or first series (the series may include only one construct) of constructs integrated into the cell genome, and desirably a second or second series (the series may include only one construct) of constructs integrated into the cell genome.

The nature and number of constructs will depend on the nature of the chimeric used protein, and the role it plays in the cell. Where the chimeric fused protein is to be associated with expression of a gene, so that an intracellular cellular targeting sequence will be employed which will direct the chimeric fused protein to be associated with the cellular surface membrane, or associated with an organelle e.g. nucleus or vesicle, then there will normally be at least two series of constructs: a first series which directs expression, and desirably a second series which results in expression of a desired RNA transcript or protein.

Only a single construct in the first series will be required where a homooligomer, usually a homodimer, is involved, while two or more, usually not more than three constructs may be involved, where a heterooligomer is involved. The expression products of the first series of constructs will be associated with actuation of one transcription and will normally be directed to the surface membrane or the nucleus, where the oligomerized chimeric fusion protein is able to initiate, directly or indirectly, the transcription of one or more target genes. A second series of additional constructs will be required where an exogenous gene(s) is introduced, whose transcription will be activated by the oligomerizing of the chimeric fused protein.

A different first series of constructs may be employed where the chimeric fused proteins are intracellular and can act directly without initiation of transcription of another gene. For example, proteins associated with exocytosis may be expressed inducibly or constitutively, where the proteins will not normally complex except in the presence of the oligomerizing molecule. By employing proteins which do not complex in the host cell; are inhibited by complexation with other proteins, which inhibition may be overcome by oligomerization with the ligand, require activation through a process which is not available in the host cell; or by modifying the proteins which direct fusion of a vesicle with the plasma membrane to form chimeric fused proteins, where the extent of complex formation and membrane fusion is enhanced in the presence of the oligomerizing molecule, exocytosis may be induced by the oligomerizing molecule.

Other intracellular proteins, such as multi-subunit kinases, phosphatases and cell cycle control proteins may be similarly modified and used.

The series of constructs may be defined as follows:

(1) constructs which encode a chimeric fused protein comprising a binding domain and an action domain, where the binding domain is extracellular or intracellular and the action domain is intracellular and when the chimeric fused protein is oligomerized by itself or with a different fused protein comprising a different action domain, a signal is induced which results in a series of events resulting in transcriptional activation of one or more genes;

(2) constructs which encode a protein having a binding domain and an action domain, where the binding domain and action domain are in the nucleus and when the protein is oligomerized by itself or with a different action domain induces initiation of transcription directly by the complex of the oligomerized domains binding to the DNA transcriptional initiation region;

(3) constructs which encode a binding domain and an action domain, where the binding domain and the action domain are cytoplasmic and oligomerization of different action domains results in exocytosis; and (4) constructs which encode a binding domain and an action domain, where the binding domain and action domain are extracellular and the action domain is associated with initiating a biological activity.

II. Transcription Regulation

The construct(s) of groups (1) and (2) will be considered first. Group (1) constructs will differ from group (2) constructs in their effect. Group (1) constructs will normally be pleiotropic, activating a number of wild-type genes, as well as the target gene(s). In addition, the response of the expression products of group (1) genes to the ligand will be relatively slow. Group (2) constructs can be directed to a specific target gene and will be capable of limiting the number of genes which will be transcribed. The response of expression products of group (2) constructs to the ligand will be very rapid.

The subject system for groups (1) and (2) will include a first series of constructs which comprises the chimeric fused proteins, usually involving from one to three, usually one to two, different constructs. The system usually will also include a second series of constructs which will provide for expression of one or more genes, usually an exogenous gene, in the sense that the gene is not normally expressed by the cell, because of the nature of the cell, a genetic defect, the gene is from a different species or is a mutated or synthetic gene, or The fused chimeric protein construct of groups (1), (2) and (3) are characterized by having an intracellular cellular targeting domain comprising a sequence which directs the chimeric protein to the desired compartment, e.g. surface membrane, nucleus, vesicular membrane, or other site, where a desired physiological activity may be initiated by the oligomerization, at least dimerization, of the chimeric fused protein.

Also present is a second or binding domain which is capable of binding an epitope or binding site of a ligand. Since the ligand can be dimeric or higher order in the number of epitopes present in the ligand that can be bound by the same or different binding domains, oligomers of the chimeric fused protein can be formed in the presence of the ligand. The binding domain may have one or a plurality of binding sites, so that homooligomers may be formed with a divalent ligand. In this way the ligand is able to oligomerize the chimeric fused protein by having two or more epitopes to which the second domain may bind, thus providing for higher order oligomerization of the chimeric fused protein.

The third and action domain will be a functional domain in initiating a biological activity, by virtue of the oligomerization of the binding domain and association of the action domains. Thus, the third domain may be associated with transduction of a signal as a result of the binding of the ligand, where the signal results in the transcription of one or more genes, depending on the particular intermediate components involved in the signal transduction. The third domains may be transcription factors, where the oligomerization of the transcription factors results in the initiation of transcription of one or more target genes, endogenous and/or exogenous. The third domains may be proteins associated with fusion of vesicle membranes with the surface or other membrane, e.g. proteins of the SNAP and SNARE groups (See, Sollner et al. (1993) Nature 362, 318 and 353; Cell (1993) 72, 43).

A. Surface Membrane Receptor

The first chimeric fused proteins to be discussed will be the proteins involved with the surface membrane which are capable of transducing a signal which results in the transcription of one or more genes, where the process will involve a number of auxiliary proteins resulting in a cascade with the final step of binding of transcription factors to the target and potentially other gene promoter regions. The fused protein comprises a signal sequence, which may be subject to processing, so as not to be present in the mature protein. The fused protein also comprises a binding domain capable of binding a pre-determined ligand, a membrane binding domain which includes a transmembrane domain or an attached lipid for translocating the fused protein to the cell surface/membrane and retaining the protein bound to the cell surface membrane, and, as the action domain, a cytoplasmic signal initiation domain. The cytoplasmic signal initiation domain is capable of initiating a signal which results in transcription of a gene having a recognition sequence for the initiated signal in the transcriptional initiation region.

The gene which is regulated by the signal from the chimeric protein will be referred to as the "target" gene. The molecular portion of the chimeric protein which provides for binding to a membrane is the "retention domain," a moiety which is directly bound to the lipid layer of the membrane, such as through lipid participation in the membrane or extending through the membrane, or the like, where the protein becomes translocated to and bound to the membrane, particularly the cellular membrane.

B. Nuclear Transcription Factors

Another first construct involves a cellular targeting sequence which provides for the protein to be translocated to the nucleus. This signal consensus sequence has a plurality of basic amino acids, referred to as a bipartite basic repeat. This sequence may appear in any portion of the molecule internal or proximal to the N- or C-terminus and results in the chimeric fused protein being inside the nucleus. There will be at least two chimeric proteins, including one having an action domain which binds to the DNA of the transcription initiation region and a second chimeric protein, which comprises an activation domain, which together with the DNA binding domain can initiate transcription. The two action domains or transcription factors may be derived from the same or different protein molecule.

The transcription factors may be endogenous or exogenous to the cellular host. If the transcription factors are exogenous, functional in the host and can cooperate with the endogenous RNA polymerase (rather than having to introduce a gene which encodes an exogenous RNA polymerase), then an exogenous promoter region functional with the fused transcription factors can be provided with the second construct, so as to restrict the gene(s) which are transcribed to those having the exogenous promoter region.

A large number of transcription factors are known which require two subunits for activity or a single transcription factor can be divided into two separate functional domains, so that each domain is inactive, but when brought together in close proximity, the two domains are active. Transcription factors which may find use include yeast GAL4, which may be divided into two domains as described by Fields and Song, supra. The authors use a fusion of GAL4(1–147)-SNF1 and SNF4-GAL4(768–881), where the SNF1 and −4 may be replaced by the subject binding proteins as binding domains. Combinations of GAL4 and VP16 or HNF-1 may be employed. Other transcription factors are members of the Jun, Fos, and ATP/CREB families, Oct1, Sp1, HNF-3, the steriod receptor superfamily, and the like.

Instead of using the combination of a DNA binding domain and a naturally occurring activation domain or modified form thereof, the activation domain may be substituted with one of the binding proteins associated with bridging between the activation domain and RNA polymerase, particularly RNA polymerase II. These proteins include the proteins referred to as TAF's, the TFII proteins, particularly B and D, or the like. Thus, one may use any one or combination of proteins, for example, fused proteins or binding motifs thereof, which serve in the bridge between the DNA binding protein and RNA polymerase and provide for initiation of transcription. Preferably, the protein closest to the RNA polymerase will be employed in conjunction with the DNA binding domain to provide for initiation of transcription. If desired, the subject constructs can provide for three or more, usually not more than about 4, proteins to be brought together to provide the transcription initiation complex.

Rather than have an activation domain as an action domain, an inactivation domain may be employed, such as ssn-6/TUP-1. In this manner, regulation results in turning off the transcription of a gene which is constitutively expressed. For example, in the case of gene therapy one may provide for constitutive expression of a hormone, such as growth hormone, blood proteins, immunoglobulins, etc. By employing constructs which involve a DNA binding domain joined to a ligand binding domain and an inactivation domain bound to a ligand binding domain, the expression of the gene can be inhibited.

These second domains are fused to the third domain providing the chimeric protein in the same manner as described for the other constructs. For the most part, the N-terminus of the transcription factor will be bound to the C-terminus of the binding domain, although in many situations the reverse may be true, for example, where a single transcription factor having two domains is divided into two subunits to become part of two different constructions.

III. Exocytosis

Another use for the oligomerization mechanism is exocytosis, where export of a protein rather than transcription is controlled by the ligand. This may be used in conjunction with the expression of one or more proteins of interest, rather than providing for secretion of the protein of interest by providing a signal sequence for directing secretion of the protein of interest. In this situation there would be two different first constructs. One construct would direct the protein to the vesicle to be integrated into the vesicular membrane. This is described by Sollner et al., supra. Proteins which may find use as the vesicle binding protein include VAMP (synaptobrevin), SNC2, rab3, SEC4, etc., individually or in combination. The cellular membrane protein may include syntaxin, SSO1, SSO2, neurexin, etc., individually or in combination. The other construct would provide for transport to the surface membrane and employs the myristoyl signal sequence, as described above. The encoded proteins are described in the above references and, all or functional part, may serve as the action domains. These constructs could be used in conjunction with the expression of an exogenous protein, properly encoded for transport to a vesicle or for an endocytotic endogenous protein, to enhance export of the endogenous protein.

Various mechanisms may be employed for exocytosis. Depending on the cell type and which protein is limiting for endocytosis in the cell, one or more of the vesicle bound proteins or cellular proteins may be encoded by one or more constructs having a response element which is activated by the ligand. Of particular interest is the combination of VAMP and syntaxin. Alternatively, one may provide for constitutive expression of non-limiting proteins controlling exocytosis. And provide for ligand regulated expression of the exocytosis limiting protein. Finally, one can provide for constitutive expression of the chimeric proteins associated with exocytosis, so that exocytosis is controlled by oligomerizing the chimeric proteins with the ligand. By employing appropriate binding domains, one can provide for different chimeric proteins to be oligomerized on the vesicle surface to form an active complex, and/or linking of the vesicle protein(s) with the cell membrane surface protein through the ligand. The chimeric proteins may not provide for exocytosis in the absence of the ligand due to modifications in the ligand which substantially reduce the binding affinity between the proteins governing exocytosis, such as deletions, mutations, etc. These modifications can be readily determined by employing overlapping fragments of the individual proteins and determining which fragments retain activity. The fragments may be further modified by using alanine substitutions to determine the individual amino acids which substantially affect binding. (Beohncke et al., J. Immunol. (1993) 150, 331–341; Evavold et al., ibid (1992) 148, 347–353)

The proteins assembled in the lumen of the vesicle, as well as the fused proteins associated with exocytosis may be expressed constitutively or inducibly, as described above. Depending on the purpose of the exocytosis, whether endogenous or exogenous proteins are involved, whether the proteins to be exported are expressed constitutively or inducibly, whether the same ligand may be used for initiating transcription of the fused proteins associated with exocytosis and the proteins to be exported, or whether the different proteins are to be subject to different inducible signals, may determine the manner in which expression is controlled. In one aspect, the exocytosis mechanism would be the only event controlled by the ligand. In other aspects, both expression of at least one protein and exocytosis may be subject to ligand control.

Various proteins may be modified by introduction of a cellular targeting sequence for translocation of the protein to a vesicle without loss of the physiological activity of the protein. By using exocytosis as the delivery mechanism, relatively high dosages may be delivered within a short period of time to produce a high localized level of the protein or a high concentration in the vascular system, depending on the nature of the host. Proteins of interest include insulin, tissue plasminogen activator, cytokines, erythropoietin, colony stimulating factors, growth factors, inflammatory peptides, cell migration factors, etc.

Coding sequences for directing proteins to a vesicle are available from the vesicle binding proteins associated with exocytosis. See, for example, Sollner, et al. supra IV. Other Regulatory Systems Other biological functions which may be controlled by oligomerization of particular activities associated with individual proteins are protein kinase or phosphatase activity, reductase activity, cyclooxygenase activity, protease activity or any other enzymatic reaction dependent on subunit association. Also, one may provide for association of G proteins with a receptor protein associated with the cell cycle, e.g. cyclins and cdc kinases, multiunit detoxifying enzymes, etc.

V. Components of Constructs

The second or additional constructs (target genes) associated with group (1) and (2) chimeric fused proteins comprise a transcriptional initiation region having the indicated target recognition sequence or responsive element, so as to be responsive to signal initiation from the activated receptor or activated transcription factors resulting in at least one gene of interest being transcribed to a sequence(s) of interest, usually mRNA, whose transcription and, as appropriate, translation may result in the expression of a protein and/or the regulation of other genes, e.g. antisense, expression of transcriptional factors, expression of membrane fusion proteins, etc.

For the different purposes and different sites, different binding domains and different cytoplasmic domains will be used. For chimeric fused protein receptors associated with the surface membrane, if the binding domain is extracellular, a variety of surface membrane protein extracellular domains may be employed. Similarly, different cytoplasmic or intracellular domains of the surface membrane proteins which are able to transduce a signal may be employed, depending on which endogenous genes are regulated by the cytoplasmic portion. Where the chimeric fused protein is internal, internal to the surface membrane protein or associated with an organelle, e.g. nucleus, vesicle, etc., the binding domain protein will be restricted to proteins which can bind molecules which will be able to cross the surface membrane or other membrane, as appropriate. Therefore, these binding proteins will generally bind to small naturally occurring or synthetic ligand molecules which do not involve proteins or nucleic acids.

A. Cytoplasmic domains

For the construct for the chimeric fused protein receptor of group (1), various cytoplasmic domains of cell surface membrane receptors may be employed, including mutants thereof, where the recognition sequence involved in initiating transcription associated with the cytoplasmic domain is known or a gene responsive to such sequence is known. Mutant receptors of interest will dissociate transcriptional activation of a target gene from activation of genes which may be associated with harmful side effects, such as deregulated cell growth or inappropriate release of cytokines. The receptor-associated cytoplasmic domains of particular interest will have the following characteristics: transcription of relatively few genes (desirably fewer than 100), generally innocuous genes, will be initiated in the cellular host by the signal which is initiated; the other factors necessary for transcription are present in the cellular host; genes which are activated other than the target genes will not affect the intended purpose for which these cells are to be used; oligomerization of the cytoplasmic domain or other available mechanism results in signal initiation; and joining of the cytoplasmic domain to the binding domain will not interfere with signalling. A number of different cytoplasmic domains are known. Many of these domains are tyrosine kinases or are complexed with tyrosine kinases, e.g. CD3ζ, IL-2R, IL-3R, etc. For a review see Cantley, et al., *Cell* (1991) 64, 281. Tyrosine kinase receptors which are activated by cross-linking, e.g. dimerization (based on nomenclature first proposed by Yarden and Ulrich, *Annu. Rev. Biochem.* (1988) 57, 443, include subclass I: EGF-R, ATR2/neu, HER2/neu, HER3/c-erbB-3, Xmrk; subclass II: insulin-R, IGF-1-R [insulin-like growth factor receptor], IRR; subclass III: PDGF-R-A, PDGF-R-B, CSF-1-R (M-CSF/c-Fms), c-kit; and subclass IV: FGF-R, flg [acidic FGF], bek [basic FGF]); neurotrophic tryosine kinases: Trk family, includes NGF-R, Ror1,2. Receptors which associate with tyrosine kinases upon cross-linking include the CD3ζ-family: CD3ζ and CD3η(found primarily in T cells, associates with Fyn); β and γ chains of $Fc_\gamma RI$ (found primarily in mast cells and basophils); γ chain of $Fc_\gamma RIII/CD16$ (found primarily in macrophages, neutrophils and natural killer cells); CD3γ, -δ, and -ε (found primarily in T cells); Ig-α/MB-1 and Ig-β/B29 (found primarily in B cells). Other cytoplasmic domains are derived from the lymphokine receptor β-chain family and include the β chain of receptors for GM-CSF, IL-2, -3, -5 and -6 (found primarily in various hematopoietic cells). AIC2B associates with Lyn; β-chain of IL-2R associates with Lck, IL-6R/gp130 IL-2β (cytoplasmic homologous); gp130; and the IFN receptor family, particularly α and γ-IFN-binding receptors.

Other receptors may include receptors for the ligands IL-4, IL-7 (interacts with p59fyn); erythropoietin (EPOR), G-CSF, leukemia inhibitory factor (LIF), ciliary neurotrophic factor (CNTR), growth hormone (GH), and prolactin (PRL). All have an extracellular cysteine motif (4 aligned cysteine residues) and the WS motif (WSXWS) and no kinase domain. Also, EPO, IL-2, 3, and 4 share additional features in their cytoplasmic domains.

The tyrosine kinases associated with activation and inactivation of transcription factors are of particular interest in providing specific pathways which can be controlled and can be used to initiate or inhibit expression of an exogenous gene.

The following table provides a number of receptors and characteristics associated with the receptor and their nuclear response elements that activate genes. The list is not exhaustive, but provides exemplary systems for use in the subject invention.

TABLE 1

| Ligand | DNA Element | Binding Factor(s) | Gene | Reference |
| --- | --- | --- | --- | --- |
| Insulin and others | cAMP responsive element (cre) | LRFI | jun-β many genes | Mol. Cell Biol. (1992), 12, 4654 PNAS, 83, 3439 |
| PDGF, FGF, TGF and others | SRE | SRF/SREBP | c-fos | Mol. Cell Biol. (1992), 12, 4769 |
| EGF | VL30 RSRF | | RVL-3 virus c-jun | Mol. Cell Biol. (1992), 12, 2793 Mol. Cell Biol. (1992), 12, 4472 |
| IFN-α | ISRE | ISGF-3 | | Gene Dev. (1989) 3, 1362 |
| IFN-γ | GAS | GAF | GBP | Mol. Cell. Biol. (1991) 11, 182 |
| PMA and TCR | | AP-1 | many genes | Cell (1987) 49, 729–739 |
| TNFα | | NFκB | many genes | Cell (1990) 62, 1019–1029 |
| Antigen | ARRE-1 | OAP/Oct-1 | many genes | Mol. Cell. Biol. (1988) 8, 1715 |
| Antigen | ARRE-2 | NFAT | IL-2 enhancer | Science (1988) 241, 202 |

In many situations mutated cytoplasmic domains may be available where the signal which is transduced may vary from the wild type, resulting in a restricted pathway as compared to the wild-type pathway(s) or a different pathway. For example, in the case of growth factors, such as EGF and FGF, mutations have been reported where the signal is uncoupled from cell growth but is still maintained with c-fos (Peters, et al., *Nature* (1992) 358, 678).

The tyrosine kinase receptors may be found on a wide variety of cells throughout the body. In contrast, the CD3ζ-family, the Ig family and the lymphokine β-chain receptor family are found primarily on hematopoietic cells, particularly T-cells, B-cells, mast cells, basophils, macrophages, neutrophils, and natural killer cells. The signals required for NF-AT transcription come primarily from the zeta (ζ) chain of the antigen receptor and to a lesser extent CD3γ, δ, ε.

The cytoplasmic domain, as it exists naturally or may be truncated, modified or mutated, will be at least about 10, usually at least about 30 amino acids, more usually at least about 50 amino acids, and generally not more than about 400 amino acids, usually not more than about 200 amino acids. (See Romeo, et al., *Cell* (1992) 68, 889–893.) While any species may be employed, preferably the species which is employed will be endogenous to the host cell. However, in many cases, the cytoplasmic domain from a different species may effectively be used. Any of the above indicated cytoplasmic domains may find use, as well as others which are presently known or may subsequently be discovered.

For the most part, the other chimeric fused proteins associated with transcription factors, will differ primarily in having a cellular targeting sequence which directs the chimeric fused protein to the internal side of the nuclear membrane and having transcription factors or portions thereof as the action domains. Usually, the transcription factor action domains may be divided into "DNA binding domains" and "activation domains." One may provide for a DNA binding domain with one or more ligand binding domains and an activation domain with one or more ligand binding domains. In this way the DNA binding domain may be coupled to a plurality of binding domains and/or activation domains. Otherwise, the discussion for the chimeric fused proteins associated with the surface membrane for signal transduction is applicable to the chimeric fused proteins for direct binding to genomic DNA. Similarly, the chimeric fused protein associated with exocytosis will differ primarily as to the proteins associated with fusion of the vesical membrane with the surface membrane, in place of the transducing cytoplasmic proteins.

B. Cellular Targeting Domains

A signal peptide or sequence provides for transport of the chimeric fused protein to the cell surface membrane, where the same or other sequences may encode binding of the chimeric fused protein to the cell surface membrane. While there is a general motif of signal sequences, two or three N-terminal polar amino acids followed by about 15–20 primarily hydrophobic amino acids, the individual amino acids may be widely varied. Therefore, substantially any signal peptide may be employed which is functional in the host and may or may not be associated with one of the other domains of the chimeric fused protein. Normally, the signal peptide is processed and will not be retained in the mature chimeric fused protein. The sequence encoding the signal peptide is at the 5'-end of the coding sequence and will include the initiation methionine codon.

The choice of membrane retention domain is not critical to this invention, since it is found that such membrane retention domains are substantially fungible and there is no critical amino acid required for binding or bonding to another membrane region for activation. Thus, the membrane retention domain may be isolated from any convenient surface membrane or cytoplasmic protein, whether endogenous to the host cell or not.

There are two different membrane retention domains: a transmembrane retention domain, which is an amino acid sequence which extends across the membrane; and a lipid membrane retention domain, which lipid associates with the lipids of the cell surface membrane.

For the most part, for ease of construction, the transmembrane domain of the cytoplasmic domain or the receptor domain will be employed, which may tend to simplify the construction of the fused protein. However, for the lipid membrane retention domain, the processing signal will usually be added at the 5' end of the coding sequence for N-terminal binding to the membrane and proximal to the 3' end for C-terminal binding. The lipid membrane retention domain will have a lipid of from about 12 to 24 carbon atoms, particularly 14 carbon atoms, more particularly myristoyl, joined to glycine. The signal sequence for the lipid binding domain is an N-terminal proximal sequence and may be varied widely, usually having glycine at residue 2 and lysine or arginine at residue 7 (Kaplan, et al., *Mol. Cell. Biol.* (1988) 8, 2435). Peptide sequences involving post-translational processing to provide for lipid membrane binding are described by Carr, et al., *PNAS USA* (1988) 79, 6128; Aitken, et al., *FEBS Lett.* (1982) 150, 314; Henderson, et al., *PNAS USA* (1983) 80, 319; Schulz, et al., *Virology* (1984), 123, 2131; Dellman, et al., *Nature* (1985) 314, 374; and reviewed in *Ann. Rev. of Biochem.* (1988) 57, 69. An amino acid sequence (SEQ ID NO. 1) of interest includes the sequence M-G-S-S-K-S-K-P-K-D-P-S-Q-R. Various DNA sequences may be used to encode such sequence in the fused receptor protein.

Generally, the transmembrane domain will have from about 18–30 amino acids, more usually about 20–30 amino acids, where the central portion will be primarily neutral, non-polar amino acids, and the termini of the domain will be polar amino acids, frequently charged amino acids, generally having about 1–2 charged, primarily basic amino acids at the termini of the transmembrane domain followed by a helical break residue, e.g. pro- or gly-.

C. Ligand Binding Domain

The ligand binding domain may be any convenient domain which will allow for induction using a natural or unnatural ligand, preferably an unnatural synthetic ligand. The binding domain may be internal or external to the cellular membrane, depending upon the nature of the construct, and the choice of ligand. A wide variety of binding proteins, including receptors, are known, which include binding proteins associated with the cytoplasmic regions indicated above. Of particular interest are binding proteins for which there are known synthetic ligands or such ligands may be readily produced. These receptors or ligand binding domains include the FKBP or cyclophilin receptor, and other receptors indicated above, the steriod receptor, the tetracycline receptor, and the like, as well as unnatural receptors, which may be obtained from antibodies, particularly the heavy or light chain subunit, mutated sequences thereof, random amino acid sequences obtained by stochastic procedures, combinatorial syntheses, and the like. For the most part, the receptor domains will be at least about 50 amino acids, and fewer than about 350 amino acids, usually fewer than 200 amino acids, either as the natural domain or truncated active portion thereof.

The receptor domain may be internalized or externalized depending upon the construction of the chimeric gene and the availability of an appropriate ligand. For hydrophobic ligands, the binding domain may be on either side of the membrane, but for hydrophilic ligands, particularly protein ligands, the binding domain will usually be external, unless there is a transport system for internalizing the ligand in a form in which it is available for binding. The receptor domain can be internalized by having a signal peptide and transmembrane domain encoded 5' or 3' of the receptor domain or by having a lipid attachment signal sequence 5' of the receptor domain. Where the receptor domain is between the signal peptide and the transmembrane domain, the receptor domain will be externalized.

The receptor may be subject to mutagenesis for a variety of reasons. The mutagenized protein may provide for higher binding affinity, allow for discrimination by the ligand or the naturally occurring receptor and the mutagenized receptor, provide opportunities to design a receptor ligand pair, or the like. The change in the receptor may involve changes in amino acids known to be at the binding site, random mutagenesis using combinatorial techniques, where the codons for the amino acids associated with the binding site or other amino acids associated with conformational changes may be subject to mutagenesis by changing the codon(s) for the particular amino acid, either with known changes or randomly, expressing the resulting proteins in an appropriate prokaryotic host and then screening the resulting proteins for binding. Illustrative of this situation is to modify Phe36 to Ala and/or Asp37 to Gly or Ala to accommodate a substituent at positions 9 or 10 of FK506 or FK520.

Antibody subunits, e.g. heavy or light chain, particularly fragments, more particularly all or part of the variable region, may be used as the binding domain. Antibodies may be prepared to haptenic molecules which are physiologically acceptable and the individual submits screened for binding affinity. The cDNA encoding the subunits may be isolated and modified by deletion of the constant region, portions of the variable region, mutagenesis of the variable region, or the like, to obtain a binding protein domain that has the appropriate affinity for the ligand. In this way, almost any physiologically acceptable haptenic compound may be employed as the ligand or to provide an epitope for the ligand. Instead of antibody units, natural receptors may be employed, where the binding domain is known and there is a useful ligand for binding.

The ability to employ in vitro mutagenesis or combinatorial modifications of sequences encoding proteins allows for the production of libraries of proteins which may be screened for binding affinity for different ligands. For example, one may totally randomize a sequence of 1 to 5, 10 or more codons, at one or more sites in a DNA sequence encoding a binding protein, make an expression construct and introduce the expression construct into a unicellular microorganism, and develop a library. One can then screen the library for binding affinity to one or desirably a plurality of ligands. The best affinity sequences which are compatible with the cells into which they would be introduced may then be used as the binding domain. The ligand would be screened with the host cells to be used to determine the level of binding of the ligand to endogenous proteins. A binding profile could be defined weighing the ratio of binding affinity to the mutagenized binding domain with the binding affinity to endogenous proteins. Those ligands which have the best binding profile could then be used as the ligand.

D. Multimerization

The transduced signal will normally result by oligomerization of the construct as a result of ligand binding, although other binding events, for example allosteric activation, may be employed to initiate a signal. The construct of the chimeric protein will vary as to the order of the various domains and the number of repeats of an individual domain. For the extracellular receptor domain in the 5'–3' direction of transcription, the construct will comprise the signal peptide, the receptor domain, the transmembrane domain and the signal initiation domain, which last domain will be intracellular (cytoplasmic). However, where the receptor domain is intracellular, different orders may be employed, where the signal peptide may be followed by either the receptor or signal initiation domain, followed by the remaining domain, or with a plurality of receptor domains, the signal initiation domain may be sandwiched between receptor domains. Usually, the active site of the signal initiation domain will be internal to the sequence and not require a free carboxyl terminus. Either of the domains may be multimerized, particularly the receptor domain, usually having not more than about 5 repeats, more usually not more than about 3 repeats.

For multimerizing the receptor, the synthetic ligand for the receptor domains of the chimeric surface membrane proteins will usually be multimeric in the sense that it will have at least two binding sites, with each of the binding sites capable of binding to the receptor domain. Desirably, the subject ligands will be a dimer or higher order oligomer, usually not greater than about tetrameric, of small synthetic organic molecules, the individual molecules being at least about 150 D and less than about 5 kD, usually less than about 3 kD. A variety of pairs of synthetic ligands and receptors may be employed. For example, for natural receptors dimeric FK506 may be used with the FKBP receptor, dimerized cyclosporin A may be used with the cyclophilin receptor, dimerized estrogen with the estrogen receptor, dimerized glucocorticoids with the glucocorticoid receptor, dimerized tetracycline with the tetracycline receptor, dimerized vitamin D with the vitamin D receptor, and the like, or higher orders of the ligands, e.g. trimeric. For unnatural receptors, e.g. antibody subunits or modified antibody subunits, any of a large variety of compounds may find use. A significant characteristic of these ligand binding units are that they bind the receptor with high affinity ($K_d \leq 10^{-8}$M) and are able to be dimerized chemically.

The ligand may have different molecules with different epitopes. Thus, the ligand link chimeric fused proteins having the same or different binding domains, e.g. FK506 and cyclosporin.

V. Cells

The cells which are involved will be mammalian cells, particularly primate, more particularly human, but may be associated with any animal of interest, particularly domesticated animals, such as equine, bovine, murine, ovine, canine, feline, etc. Among these species, various types of cells may be involved, such as hematopoietic, neural, mesenchymal, cutaneous, mucosal, stromal, muscle, spleen, reticuloendothelial, epithelial, endothelial, hepatic, kidney, gastrointestinal, pulmonary, etc. Of particular interest are hematopoietic cells, which may include any of the nucleated cells which may be involved with the lymphoid or myelomonocytic lineages. Of particular interest are members of the T- and B-cell lineages, macrophages and monocytes, myoblasts and fibroblasts. Also of particular interest are stem and progenitor cells, such as hematopoietic neural, stromal, muscle, hepatic, pulmonary, gastrointestinal, etc.

The cells may be autologous cells, syngenic cells. allogenic cells and even in some cases, xenogeneic cells. The cells may be modified by changing the major histocompatibility complex ("MHC", profile, by inactivating $\beta_2$-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

In some instances specific clones or oligoclonal cells may be of interest, where the cells have a particular specificity, such as T cells and B cells having a specific antigen specificity or homing target site specificity.

VI. Ligands

The ligands which may be used may be varied widely, being derived from naturally occurring compounds or from synthetic compounds. The criteria for the ligand are that the ligand is physiologically acceptable, has a reasonable therapeutic dosage range, desirably, can be taken orally (stable in the gastrointestinal system and absorbed into the vascular system), as appropriate, can cross the cellular and other membranes, as necessary, and binds to the receptor domain with reasonable affinity. A first desirable criterion is that the compound is relatively physiologically inert, but for its activating capability with the receptors. The less the ligand binds to native receptors and the lower the proportion of total ligand which binds to natural receptors, the better the response will normally be. Particularly, the ligand should not have a strong biological effect on native proteins. For the most part, the ligands will be non-peptide and non-nucleic acid.

The subject compounds will for the most part have two or more units, where the units may be the same or different, joined together through a central linking group, where the units will be individual compounds capable of binding the receptor domain, where each of the units will usually be joined to the linking group at the same sites.

As indicated above, there are a variety of naturally-occurring receptors for small non-proteinaceous organic molecules, which small organic molecules fulfill the above criteria, and can be dimerized at various sites to provide a ligand according to the subject invention. Substantial modifications of these compounds are permitted, so long as the binding capability is retained and with the desired specificity. Many of the compounds will be macrocyclics, e.g. macrolides.

Preferred ligands comprise dimers of compounds binding to the FKBP protein, which includes homo- and heteromultimers (usually 2–4, more usually 2–3 units) of cyclosporin A, cyclophilin, FK506, FK520, and derivatives thereof, and rapamycin, retaining their binding capability to the natural or mutagenized binding domain. Sites of interest for linking of FK506 include positions involving annular carbon atoms from about 17 to 24 and substituent positions bound to those annular atoms, e.g. 21 (allyl), 22, 37, 38, 39 and 40, or 32 (cyclohexyl), while the same positions except for 21 are of interest for FK520. For cyclosporin, sites of interest include MeBmt, position 3 and position 8.

Of particular interest is to modify the ligand so as to change its binding characteristics, particularly as to the binding to the naturally occurring receptor for the ligand. Concomitantly, one would change the binding protein to accommodate the change in the ligand. For example, one could modify the groups at position 9 or 10, so as to increase their steric requirement, by substituting the hydroxyl with a group having greater steric requirements, or modifying the carbonyl at position 10, substituting the carbonyl with a group having greater steric requirements or functionalizing the carbonyl, e.g. forming an N-substituted Schiff's base or imine, to enhance the bulk at that position. Various functionalities which may be conveniently introduced at those sites are alkyl groups to form ethers, acylamido groups, N-alkylated amines, where a 2-hydroxyethylimine can also form a 1,3-oxazoline, or the like. Generally, the substituents will be from about 1 to 6, usually 1 to 4, and more usually 1 to 3 carbon atoms, with from 1 to 3, usually 1 to 2 heteroatoms, which will usually be oxygen, sulfur, nitrogen, or the like. By using different derivatives of the basic structure, one may create different ligands with different conformational requirements for binding. By mutagenizing receptors, one may have different receptors or substantially the same sequence having different affinities for modified ligands not differing significantly in structure.

Other ligands which may find use are steroids. The steroids may be oligomerized, so that the natural biological activity is substantially diminished, while the steroid retains its binding capability. Glucocorticoids and estrogens may find use. Various drugs may find application, where the drug is known to bind to a particular receptor with high affinity, particularly, where the binding domain or the receptor is known, so that the entire protein is not required to provide the binding domain. For this purpose, enzymes and enzyme inhibitors may find use.

A. Linkers

Various functionalities may be involved in the linking, such as amide groups, including carbonic acid derivatives, ethers, esters, including organic and inorganic esters, amino, or the like. To provide for linking, the particular monomer may be modified by oxidation, hydroxylation, substitution, reduction, etc., to provide a site for coupling. Depending on the monomer, various sites may be selected as the site of coupling.

The multimeric ligands may be synthesized by any convenient means, where the linking group will be at a site which does not interfere with the binding of the binding site of a ligand to the receptor. Where the active site for physiological activity and binding site of a ligand to the receptor domain are different, it will usually be desirable to link at the active site to inactivate the ligand. Various linking groups may be employed, usually of from 1–30, more usually from about 1–20 atoms in the chain between the two molecules (other than hydrogen), where the linking groups will be primarily composed of carbon, hydrogen, nitrogen, oxygen, sulphur and phosphorous. The linking groups may involve a wide variety of functionalities, such as amides and esters, both organic and inorganic, amines, ethers, thioethers, disulfides, quaternary ammonium salts, hydrazines, etc. The chain may include aliphatic, alicyclic, aromatic or heterocyclic groups. The chain will be selected based on ease of synthesis and the stability of the multimeric ligand. Thus, if one wishes to maintain long-term activity, a relatively inert chain will be used, so that the multimeric ligand link will not be cleaved. Alternatively, if one wishes only a short half-life in the blood stream, then various groups may be employed which are readily cleaved, such as esters and amides, particularly peptides, where circulating and/or intracellular proteases may cleave the linking group.

Various groups may be employed as the linking group between ligands, such as alkylene, usually of from 2 to 20 carbon atoms, azalkylene (where the nitrogen will usually be between two carbon atoms), usually of from 4 to 18 carbon atoms), N-alkylene azalkylene (see above), usually of from 6 to 24 carbon atoms, arylene, usually of from 6 to 18 carbon atoms, ardialkylene, usually of from 8 to 24 carbon atoms, bis-carboxamido alkylene of from about 8 to 36 carbon atoms, etc. Illustrative groups include decylene, octadecylene, 3-azapentylene, 5-azadecylene, N-butylene 5-azanonylene, phenylene, xylylene, p-dipropylenebenzene, bis-benzoyl 1,8-diaminooctane, and the like.

B. Ligand Characteristics

For intracellular binding domains, the ligand will be selected to be able to be transferred across the membrane in a form where it is active, that is, it will be membrane permeable. Various ligands are hydrophobic or may be made so by appropriate modification with lipophilic groups. Particularly, the linking bridge may serve to enhance the lipophilicity of the ligand by providing aliphatic side chains of from about 12 to 24 carbon atoms. Alternatively, one or more groups may be provided which will enhance transport across the membrane, desirably without endosome formation.

In some instances, multimeric ligands need not be employed. For example, molecules may be employed where two different binding sites provide for dimerization of the receptor. In other instances, binding of the ligand may result in a conformational change of the receptor domain, resulting in activation, e.g. oligomerization, of the receptor. Other mechanisms may also be operative for inducing the signal, such as binding a single receptor with a change in conformation resulting in activation of the cytoplasmic domain.

C. Ligand Antagonists

Monomeric ligands may find use for reversing the effect of the multimeric ligand. Thus, if one wishes to rapidly terminate the effect of cellular activation, a monomeric ligand may be used. Conveniently, the parent compound may be modified at the same site as the multimer, using the same procedure, except substituting a monofunctional compound for the polyfunctional compound. Instead of the polyamines, monoamines, particularly of from 2 to 20, usually 2 to 12 carbon atoms may be used, such as ethylamine, hexylamine, benzylamine, etc. Alternatively, the parent compound may be used, where the parent compound does not have an undesirable physiological activity.

VII. Target Gene

A Transcription Initiation Region

The second gene which is introduced will have a responsive element in the 5' region, which responds to the signal induced by the chimeric fused receptor protein. Therefore, it will be necessary to know at least one transcription initiation system, e.g. factor, which is activated either directly or indirectly, by the cytoplasmic domain or can be activated by association of two domains. It will also be necessary to know at least one promoter region which is responsive to the resulting transcription initiation system. Either the promoter region or the gene under its transcriptional control need be known.

Where the responsive element is known, it may be included in the construct to provide an expression cassette for integration into the genome. It is not necessary to have isolated the particular sequence of the responsive element, so long as a gene is known which is activated by the cytoplasmic domain upon natural ligand binding to the protein comprising the cytoplasmic domain. Homologous recombination can then be used for insertion of the gene of interest downstream from the promoter region to be under the transcriptional regulation of the endogenous promoter region. Where the specific responsive element sequence is known, that may be used in conjunction with a different transcription initiation region, which may have other aspects, such as a high or low activity as to the rate of transcription, binding of particular transcription factors and the like.

The expression construct will therefore have at its 5' end in the direction of transcription, the responsive element and the promoter sequence which allows for induced transcription initiation of a target gene of interest, usually a therapeutic gene. The transcriptional termination region is not as important, and may be used to enhance the lifetime of or make short half-lived mRNA by inserting AU sequences which serve to reduce the stability of the mRNA and, therefore, limit the period of action of the protein. Any region may be employed which provides for the necessary transcriptional termination, and as appropriate, translational termination. The responsive element may be a single sequence or may be oligomerized, usually having not more than about 5 repeats, usually having about 3 repeats.

B. Product

A wide variety of genes may be employed, where the gene may encode a protein of interest or an antisense sequence of interest or a ribozyme of interest. The target gene can be any sequence of interest which provides a desired phenotype. The target gene may express a surface membrane protein, a secreted protein, a cytoplasmic protein, or there may be a plurality of target genes which may express different types of products. The target gene may be an antisense sequence which may modulate a particular pathway by inhibiting the translation of a transcriptional regulation protein or turn on a particular pathway by inhibiting the translation of an inhibitor of the pathway. The target gene may encode a ribozyme which may modulate a particular pathway by interfering, at the RNA level, with the expression of a relevant transcriptional regulator or with the expression of an inhibitor of a particular pathway. The proteins which are expressed, singly or in combination, may involve homing, cytotoxicity, proliferation, immune response, inflammatory response, clotting or dissolving of clots, hormonal regulation, or the like. The proteins expressed could be naturally-occurring, mutants of naturally-occurring proteins, unique sequences, or combinations thereof. The gene may be any gene which is secreted by a cell, so that the encoded product may be made available at will, whenever desired or needed by the host. Various secreted products include hormones, such as insulin, human growth hormone, glucagon, pituitary releasing factor, ACTH, melanotropin, relaxin, etc.; growth factors, such as EGF, IGF-1, TGF-$\alpha$, -$\beta$, PDGF, G-CSF, M-CSF, GM-CSF, FGF, erythropoietin, megakaryocytic stimulating and growth factors, etc.; interleukins, such as IL-1 to -11; TNF-$\alpha$ and -$\beta$, etc.; and enzymes, such as tissue plasminogen activator, members of the complement cascade, perforins, superoxide dismutase, coagulation factors, anti-thrombin-III, Factor VIIIc, Factor VIIIvW, $\alpha$-anti-trypsin, protein C, protein S, endorphins, dynorphin, bone morphogenetic protein, CFTR, etc.

The gene may be any gene which is naturally a surface membrane protein or made so by introducing an appropriate signal peptide and transmembrane sequence. Various proteins may include homing receptors, e.g. L-selectin (Mel-14), blood-related proteins, particularly having a kringle structure, e.g. Factor VIIIc, Factor VIIIvW, hematopoietic cell markers, e.g. CD3, CD4, CD8, B cell receptor, TCR subunits $\alpha$, $\beta$, $\gamma$, $\delta$, CD10, CD19, CD28, CD33, CD38, CD41, etc., receptors, such as the interleukin receptors IL-2R, IL-4R, etc., channel proteins, for influx or efflux of ions, e.g. $H^+$, $Ca^{+2}$, $K^+$, $Na^+$, $Cl^-$, etc., and the like; CFTR, tyrosine activation motif, zeta activation protein, etc.

Proteins may be modified for transport to a vesicle for exocytosis. By adding the sequence from a protein which is directed to vesicles, where the sequence is modified proximal to one or the other terminus, or situated in an analogous position to the protein source, the modified protein will be directed to the Golgi apparatus for packaging in a vesicle. This process in conjunction with the presence of the chimeric fused proteins for exocytosis allows for rapid transfer of the proteins to the extracellular medium and a relatively high localized concentration.

Also, intracellular proteins may be of interest, such as proteins in metabolic pathways, regulatory proteins, steroid receptors, transcription factors, etc., particularly depending upon the nature of the host cell. Some of the proteins indicated above may also serve as intracellular proteins.

The following are a few illustrations of different genes. In T-cells, one may wish to introduce genes encoding one or both chains of a T-cell receptor. For B-cells, one could provide the heavy and light chains for an immunoglobulin for secretion. For cutaneous cells, e.g. keratinocytes, particularly stem cell keratinocytes, one could provide for infectious protection, by secreting $\alpha$-, $\beta$- or $\gamma$-interferon, antichemotactic factors, proteases specific for bacterial cell wall proteins, etc.

In addition to providing for expression of a gene which may have therapeutic value, there will be many situations where one may wish to direct a cell to a particular site. The site may include anatomical sites, such as lymph nodes, mucosal tissue, skin, synovium, lung or other internal organs or functional sites, such as clots, injured sites, sites of surgical manipulation, inflammation, infection, etc. By providing for expression of surface membrane proteins which will direct the host cell to the particular site by providing for binding at the host target site to a naturally-occurring epitope, localized concentrations of a secreted product may be achieved. Proteins of interest include homing receptors, e.g. L-selectin, GMP140, CLAM-1, etc., or addressins, e.g. ELAM-1, PNAd, LNAd, etc., clot binding proteins, or cell surface proteins that respond to localized gradients of chemotactic factors. There are numerous situations where one would wish to direct cells to a particular site, where release of a therapeutic product could be of great value.

In many situations one may wish to be able to kill the modified cells, where one wishes to terminate the treatment, the cells become neoplastic, in research where the absence of the cells after their presence is of interest, or other event. For this purpose one may provide for the expression of the Fas antigen, TNF receptor, or other apoptotic initiating protein fused to a binding domain. (Watanable-Fukunaga et al. Nature (1992) 356, 314–317) In the original modification, one may provide for constitutive expression of such constructs, so that the modified cells have such proteins on their surface or present in their cytoplasm. Alternatively, one may provide for controlled expression, where the same or different ligand may initiate expression and initiate apoptosis. By providing for the cytoplasmic portions of the Fas antigen or TNF receptor in the cytoplasm joined to binding regions different from the binding regions associated with expression of a target gene of interest, one can kill the modified cells under controlled conditions.

C. Illustrative Exemplifications

One example would be a treatment for cardiac patients or patients susceptible to stroke. Cells could be administered to the patient which would be retained for extended periods of time. Illustrative cells include plasma cells, B-cells, T-cells, or other hematopoietic cells. The cell would be modified to express a protein which binds to a blood clot, e.g. having a kringle domain structure or an adhesive interactive protein, e.g. CD41, and to express a clot dissolving protein, e.g. tissue plasminogen activator, streptokinase, etc. In this way, upon activation the cells would accumulate at the site of the clot and provide for a high localized concentration.

Another example is reperfusion injury. Cells of limited lifetime could be employed, e.g. macrophages or polymorphonuclear leukocytes ("neutrophils"). The cells would have a neutrophil homing receptor to direct the cells to a site of reperfusion injury. The cell would also express superoxide dismutase, to destroy singlet oxygen and inhibit radical attack on the tissue.

A third example is autoimmune disease. Cells of extended lifetime, e.g. T cells could be employed. The constructs would provide for a homing receptor for homing to the site of autoimmune injury and for cytotoxic attack on cells causing the injury. The therapy would then be directed against cells causing the injury. Alternatively, one could provide for secretion of soluble receptors or other peptide or protein, where the secretion product would inhibit activation of the injury causing cells or induce anergy. Another alternative would be to secrete an antiinflammatory product, which could serve to diminish the degenerative effects.

A fourth example would involve treatment of chronic pain with endorphin via encapsulation. A stock of human fibroblasts is transfected with a construct in which the chimeric transcriptional regulatory protein controls the transcription of human endorphin. The DNA construct would consist of three copies of the binding site for the HNF-1' transcription factor (SEQ ID NO. 2 ) GTTAAGTTAAC upstream of a TATAAA site and a transcriptional initiation site. The endorphin cDNA would be inserted downstream of the initiation site and upstream of a polyadenylation and termination sequences. Optionally, the endorphin cDNA is outfitted with "pest" sequences to make the protein unstable or AUUA sequences in the 3' nontranslated region of the mRNA to allow it to be degraded quickly.

The fibroblasts are also transfected with a construct having two transcription units, one of which would encode the HNF-1' cDNA truncated to encode just the DNA binding sequences from amino acids 1 to 250 coupled to a trimeric FKBP binding domain under the transcriptional and translational control of regulatory initiation and termination regions functional in the fibroblasts. The construct would include an additional transcription unit driven by the same regulatory regions directing the production of a transcriptional activation domain derived from HNF-4 coupled to trimeric FKBP'. (The prime intends an altered FKBP that binds at nM concentration to a modified FK506. The modification inhibits binding to the endogenous FKBP.)

These genetically modified cells would be encapsulated to inhibit immune recognition and placed under the patient's skin or other convenient internal site. When the patient requires pain medication, the patient administers a dimeric ligand FK506–FK506', where about 1 $\mu$g to 1 mg would suffice. In this manner one could provide pain relief without injections or the danger of addiction.

A fifth example is the treatment of osteoporosis. Lymphocytes can be clonally developed or skin fibroblasts grown in culture from the patient to be treated. The cells would be transfected as described above, where a bone morphogenic factor cDNA gene would replace the endorphin gene. For lymphocytes, antigen specific clones could be used which would allow their destruction with antibodies to the idiotype of the sIg. In addition, administration of the antigen for the sIg would expand the cell population to increase the amount of the protein which could be delivered. The lymphocyte clones would be infused and the ligand administered as required for production of the bone morphogenic factor. By monitoring the response to the ligand, one could adjust the amount of bone morphogenic factor which is produced, so as to adjust the dosage to the required level.

A sixth situation has general application in conjunction with gene therapies involving cells which may be required to be destroyed. For example, a modified cell may become cancerous or result in another pathologic state. Constructs would be transfected into the modified cells having the necessary transcriptional and translational regulatory regions and encoding a protein which upon oligomerization results in cell death, e.g. apoptosis. Nor example, the Fas antigen or apo-1 antigen induces apoptosis in most cell types (Trauth et al. (1989) Science 245, 301–305; Watanaba-Fukunaga et al. (1992) Nature 356, 314) In this manner by co-transfecting the protective constructs into cells used for gene therapy or other purpose, where there may be a need to ensure the death of a portion or all of the cells, the cells may be modified to provide for controlled cytotoxicity by means of the ligand.

Another situation is to modify antigen specific T cells, where one can activate expression of a protein product to activate the cells. The T cell receptor could be directed against tumor cells, pathogens, cells mediating autoimmunity, and the like. By providing for activation of the cells, for example, an interleukin such as IL-2, one could provide for expansion of the modified T cells in response to a ligand. Other uses of the modified T cells would include expression of homing receptors for directing the T cells to specific sites, where cytotoxicity, upregulation of a surface membrane protein of target cells, e.g. endothelial cells, or other biological event would be desired.

Another alternative is to export hormones or factors which are exocytosed. By providing for enhanced exocytosis, a greater amount of the hormone or factor will be exported; in addition, if there is a feedback mechanism based on the amount of the hormone or factor in the cytoplasm, increased production of the hormone or factor will result. Or, one may provide for induced expression of the hormone or factor, so that expression and export may be induced concomitantly.

One may also provide for proteins in retained body fluids, e.g. vascular system, lymph system, cerebrospinal fluid, etc. By modifying cells which can have an extended lifetime in the host, e.g. hematopoietic cells, keratinocytes, muscle cells, etc. particularly, stem cells, the proteins can be maintained in the fluids for extended periods of time. The cells may be modified with constructs which provide for secretion or endocytosis. The constructs for secretion would have as the cellular targeting domain, a signal peptide, and then as in the case of the other chimeric fused proteins, a binding domain and an action domain. The action domains may be derived from the same or different proteins. For example, with tissue plasminogen activator, one could have the clot binding region as one action domain and the plasminogen active site as a different action domain. Alternatively, one could provide enhanced blockage of homing, by having a binding protein, such as LFA-1 as one action domain and a selectin as a second action domain. By modifying subunits of proteins, e.g. integrins, T-cell receptor, sIg, or the like, one could provide soluble forms of surface membrane proteins which could be brought together to bind to a molecule. Other opportunities are complement proteins, platelet membrane proteins involved in clotting, autoantigens on the surface of cells, and pathogenic molecules on the surface of infectious agents.

VIII. Introduction of Constructs into Cells

The constructs can be introduced as one or more DNA molecules or constructs, where there will usually be at least one marker and there may be two or more markers, which will allow for selection of host cells which contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. The construct(s) once completed and demonstrated to have the appropriate sequences may then be introduced into the host cell by any convenient means. The constructs may include viral sequences for transfection, if desired. Alternatively, the construct may be introduced by fusion, electroporation, biolistics, transfection, lipofection, or the like. The host cells will usually be grown and expanded in culture before introduction of the construct(s), followed by the appropriate treatment for introduction of the construct(s) and integration of the construct(s). The cells will then be expanded and screened by virtue of a marker present in the construct. Various markers which may be used successfully include hprt, neomycin resistance, thymidine kinase, hygromycin resistance, etc.

In some instances, one may have a target site for homologous recombination, where it is desired that a construct be integrated at a particular locus. For example, if one wishes to knock-out the native gene and replace the native gene with the gene encoded for by the construct, it would be desirable to provide for homologous recombination. Alternatively, instead of providing a gene, the transcriptional initiation region may be modified to be responsive to the signal initiating domain. Thus, an endogenous gene such as tPA, SOD, or the like, would be controlled by administration of the ligand. For homologous recombination, one may use either Ω or O-vectors. See, for example, Thomas and Capecchi, *Cell* (1987) 51, 503–512; Mansour, et al., *Nature* (1988) 336, 348–352; and Joyner, et al., *Nature* (1989) 338, 153–156.

The constructs may be introduced as a single DNA molecule encoding all of the genes, or different DNA molecules having one or more genes. The constructs may be introduced simultaneously or consecutively, each with the same or different markers. In an illustrative example, one construct would contain a therapeutic gene under the control of a specific responsive element, another encoding the receptor fusion protein comprising the signaling region fused to the ligand receptor domain. There could be introduced a third DNA molecule encoding a homing receptor or other product that increases the efficiency of delivery of the therapeutic product.

IX. Administration of Cells and Ligands

The cells which have been modified with the DNA constructs are then grown in culture under selective conditions and cells which are selected as having the construct may then be expanded and further analyzed, using, for example, the polymerase chain reaction for determining the presence of the construct in the host cells. Once the modified host cells have been identified, they may then be used in accordance with their intent.

Depending upon the nature of the cells, the cells may be administered in a wide variety of ways. Hematopoietic cells may be administered by injection into the vascular system, there being usually at least about $10^4$ cells and generally not more than about $10^{10}$, more usually not more than about $10^8$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Alternatively, with skin cells which may be used as a graft, the number of cells would depend upon the size of the layer to be applied to the burn or other lesion. Generally, for myoblasts or fibroblasts, the number of cells will at least about $10^4$ and nor more than about $10^8$ and may be applied as a dispersion, generally being injected at or near the site of interest. The cells will usually be in a physiologically-acceptable medium.

Instead of ex vivo modification of the cells, in many situations one may wish to modify cells in vivo. For this purpose, various techniques have been developed for modification of target tissue and cells in vivo. A number of virus vectors have been developed, such as adenovirus and retroviruses, which allow for transfection and random integration of the virus into the host. See, for example, Dubensky et al. (1984) Proc. Natl. Acad. Sci. USA 81, 7529–7533; Kaneda et al., (1989) Science 243, 375–378; Hiebert et al.

(1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The vector may be administered by injection, e.g. intravascularly or intramuscularly, inhalation, or other parenteral mode.

In accordance with in vivo genetic modification, the manner of the modification will depend on the nature of the tissue, the efficiency of cellular modification required, the number of opportunities to modify the particular cells, the accessibility of the tissue to the DNA composition to be introduced, and the like. By employing an attenuated or modified retrovirus carrying a target transcriptional initiation region, if desired, one can activate :he virus using one of the subject transcription factor constructs, so that the virus may be produced and transfect adjacent cells.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

The ligand providing for activation of the cytoplasmic domain nay then be administered as desired. Depending upon the binding affinity of the ligand, the response desired, the manner of administration, the half-life, the number of cells present, various protocols may be employed. The ligand may be administered parenterally or orally. The number of administrations will depend upon the factors described above. The ligand may be taken as a pill, powder, or dispersion, injected intravascularly, intraperitoneally, subcutaneously, by inhalation, or the like. The particular method of administration will depend upon the above factors, so that no general rules can be given. For the most part, the manner of administration will be determined empirically.

In the event that the activation by the ligand is to be reversed, the monomeric compound may be administered or other single binding site compound which can compete with the ligand. Thus, in the case of an adverse reaction or the desire to terminate the therapeutic effect, the monomeric binding compound can be administered in any convenient way, particularly intravascularly, if a rapid reversal is desired. Alternatively, one may provide for the presence of an inactivation domain with a DNA binding domain, or apoptosis by having Fas or TNF receptor present as constitutively expressed constructs.

The particular dosage of the ligand for any application may be determined an accordance with the procedures used for therapeutic dosage monitoring, where maintenance of a particular level of expression is desired over an extended period of times, for example, greater than about two weeks, or where there is repetitive therapy, with individual or repeated doses of ligand over short periods of time, with extended intervals, for example, two weeks or more. A dose of the ligand within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the ligand is chronically administered, once the maintenance dosage of the ligand is determined, one could then do assays at extended intervals to be assured that the cellular system is providing the appropriate response and level of the expression product.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells which could be administered to the population at large, each patient would be monitored for the proper dosage for the individual.

The subject methodology and compositions may be used for the treatment of a wide variety of conditions and indications. For example, B- and T-cells may be used in the treatment of cancer, infectious diseases, metabolic deficiencies, cardiovascular disease, hereditary coagulation deficiencies, autoimmune diseases, joint degenerative diseases, e.g. arthritis, pulmonary disease, kidney disease, endocrine abnormalities, etc. Various cells involved with structure, such as fibroblasts and myoblasts, may be used in the treatment of generic deficiencies, such as connective tissue deficiencies. arthritis, hepatic disease, etc. Hepatocytes could be used in cases where Large amounts of a protein must be made to complement a deficiency or to deliver a therapeutic product to the liver or portal circulation.

The following examples are offered by way illustration and not by way limitation.

EXPERIMENTAL

Cellular Transformations and Evaluation

Example 1

Induction of isolated IL-2 Enhancer-Binding Transcription Factors by cross-Linking the CD3ζ Chain of the T-Cell Receptor The plasmid pSXNeo/IL2 (IL2-SX) (FIG. 1), placing the placental secreted alkaline phosphatase gene under the control of human IL-2 promoter (−325 to +47; MCB(86) 6, 3042), and variants (i.e. NFAT-SX, NFκB-SX, OAP/Oct1-SX, and AP-1-SX) under the control of the minimal IL-2 SX, promoter (−325 to −294 and −72 to +47) plus synthetic oligomers, containing various promoter elements (i.e. NFAT, NKκKB, OAP/Oct-1, and AP1, respectively), were made by three piece ligations of 1) pPL/SEAP (Berger, et al., Gene (1988) 66,1) cut with SspI and HindIII; 2) pSV2/Neo (Southern and Berg, J. Mol. Appl. Genet. (1982) 1, 332) cut with NdeI, blunted with Klenow, then cut with PvuI; and 3) various promoter-containing plasmids (i.e. NFAT-CD8, κB-CD8, cx12lacZ-Oct-1, AP1-LUCIF3H, or cx15IL2) (described below) cut with PvuI and HindIII. NFAT-CD8 contains 3 copies of the NFAT-binding site (−286 to −257; Genes and Dev. (1990) 4, 1823) and cx12lacZ-Oct contains 4 copies of the OAP/Oct-1/(ARRE-1) binding site (MCB, (1988) 8, 1715) from the human IL-2 enhancer; κB-CD8 contains 3 copies of the NFκB binding site from the murine κ light chain (EMBO (1990) 9, 4425) and AP1-LUCIF3H contains 5 copies of the AP-1 site (5'-TGACTCAGCGC-3') from the metallothionen promoter.

Figure 5:
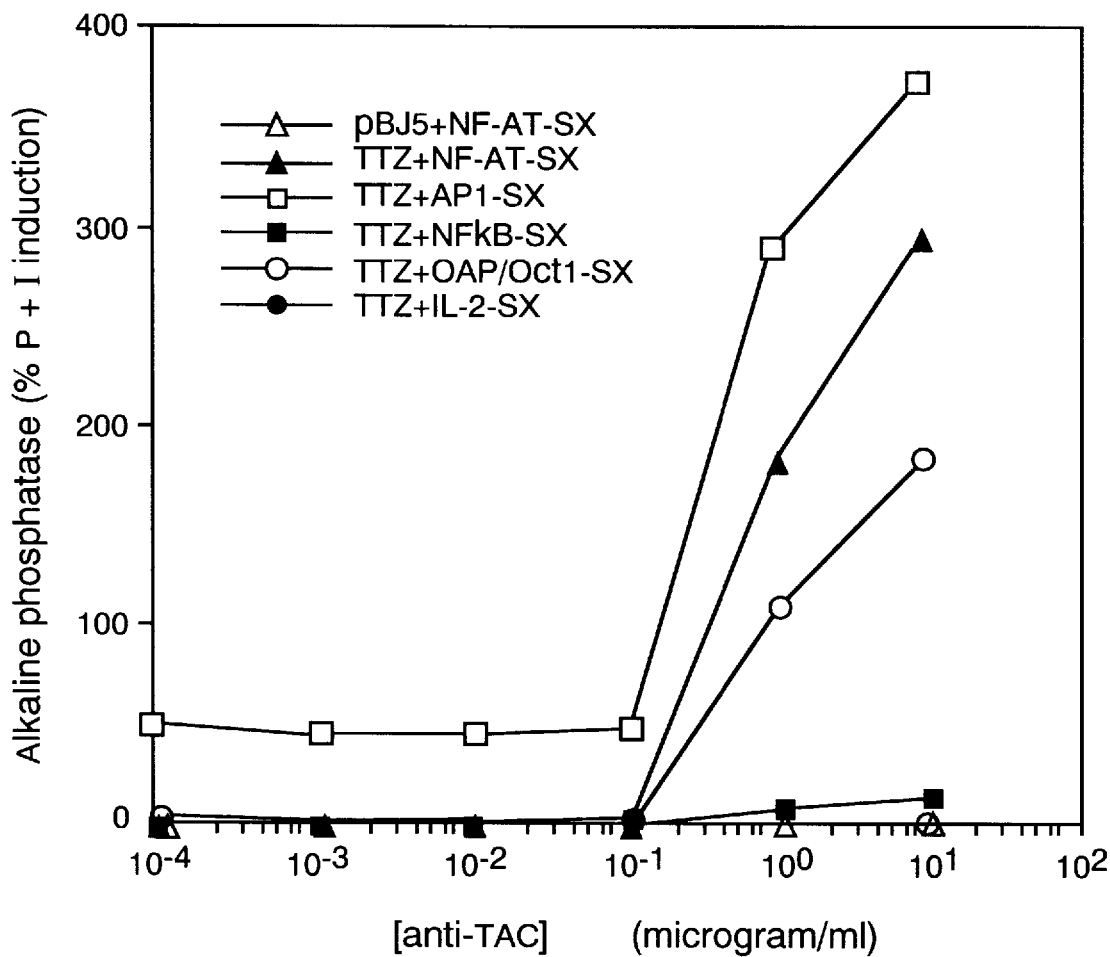
FIG. 5 is a chart of the response of reporter constructs having different enhancer groups to reaction of the receptor TAC/CD3 zeta with a ligand.

In each transfection, 5 μg of expression vector, pCDL-SRα (MCB 8, 466–72) (Tac-IL2 receptor α-chain), containing the chimeric receptor TAC/TAC/ZETA (TTZ) (PNAS 88, 8905–8909), was co-transfected along with various secreted alkaline phosphatase-based reporter plasmids (see map of pSXNeo/IL2 in FIG. 1) in TAg Jurkat cells (a derivative of the human T-cell leukemia line Jurkat stably transfected with the SV40 large T antigen (Northrup, et al., J. Biol. Chem. [1993]). Each reporter plasmid contains a multimerized oligonucleotide of the binding site for a distinct IL-2 enhancer-binding transcription factor within the context of the minimal IL-2 promoter or, alternatively, the intact IL-2 enhancer/promoter upstream of the reporter gene. After 24 hours, aliquots of cells (approximately $10^5$) were placed in microtiter wells containing log dilutions of bound anti-TAC (CD25) mAb (33B3.1; AMAC, Westbrook, Me.). As a positive control and to control for transfection efficiency, ionomycin (1 μm) and PMA (25 ng/ml) were added to aliquots from each transfection. After an additional 14 hour incubation, the supernatants were assayed for the alkaline phosphatase activity and these activities were expressed relative to that of the positive control samples. The addition of 1 ng/ml FK506 dropped all activity due to NFAT to background levels, demonstrating that deactivations are in the same pathway as that blocked by FK506. Each data point obtained was the average of two samples and the experiment was performed several times with similar results. See FIG. 5. The data show that with a known extracellular receptor, one obtains an appropriate response with a reporter gene and different enhancers. Similar results were obtained when a MAb against the TcR complex (i.e. OKT3) was employed.

Example 2
Inhibitory Activity of the Immunosuppressant Drugs FK506 and Cyclosporin A (CsA) or the Dimeric Derivative Compounds FK1012A (8), FK1012B (5), and CsA dimer (PB-1-218)

Figure 6:
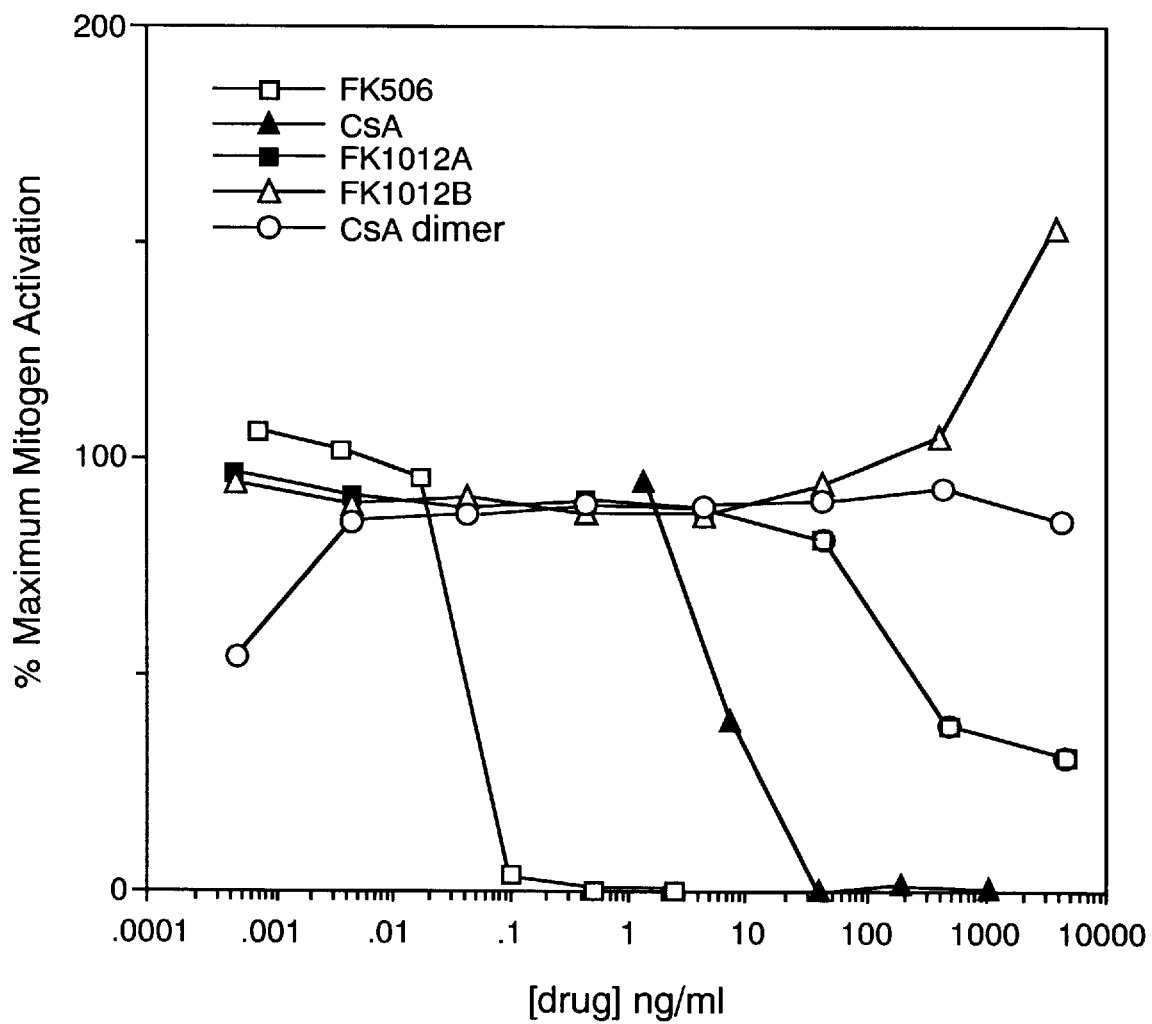
FIG. 6 is a chart of the activity of various ligands with the TAg Jurkat cells described in Example 1.

Ionomycin (1 μm) and PMA (25 ng/ml) were added to $10^5$ TAg-Jurkat cells. In addition, titrations of the various drugs were added. After 5 hours the cells were lysed in mild detergent (i.e. TRITON X-100) and the extracts were incubated with the β-galactosidase substrate, MUG (methyl galactosidyl umbelliferone) for 1 hour. A glycine/EDTA stop buffer was added and the extracts assayed for fluorescence. Each data point obtained was the average of two samples and the experiment was performed several times with similar results. Curiously, FK1012B appears to augment mitogen activity slightly at the highest concentration (i.e. 5 μg/ml); however, a control experiment shows that FK1012B is not stimulatory by itself. See FIG. 6.

Figure 7:
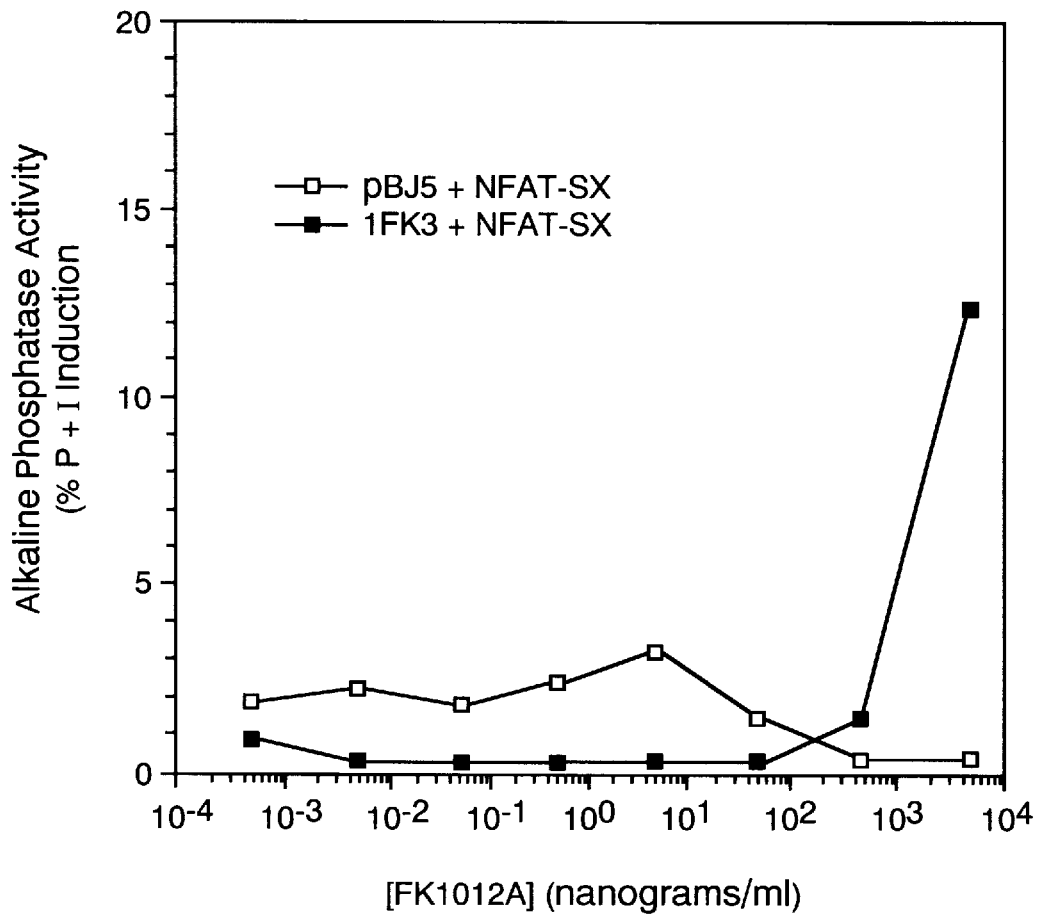
FIG. 7 is a chart of the activity of the ligand FK1012A with the extracellular receptor FKBPx3/CD3 zeta.

Example 3
Activity of the Dimeric FK506 Derivative, FK1012A, on the Chimeric FKBP12/CD3ζ (1FK3) Receptor 5 μg of the eukaryotic expression vector, pBJ5, (based on pCDL-SRα with a polylinker inserted between the 16S splice site and the poly A site) containing the chimeric receptor (1FK3), was co-transfected with 4 μg of the NFAT-inducible secreted alkaline phosphatase reporter plasmid, NFAT-SX. As a control, 5 μg of pBJ5 was used, instead of 1FK3/pBJ5, in a parallel transfection. After 24 hours, aliquots of each transfection containing approximately $10^5$ cells were incubated with log dilutions of the drug, FK1012A, as indicated. As a positive control and to control for transfection efficiency, ionomycin (1 μm) and PMA (25 ng/ml) were added to aliquots from each transfection. After an additional 14 hour incubation, the supernatants were assayed for alkaline phosphatase activity and these activities were expressed relative to that of the positive control samples. The addition of 2 ng/ml FK506 dropped all stimulations to background levels, demonstrating that the activations are in the same pathway as that blocked by FK506. Hence, FK506 or cyclosporin will serve as effective antidotes to the use of these compounds. Each data point obtained was the average of two samples and the experiment was performed several times with similar results. See FIG. 7.

Figure 2:
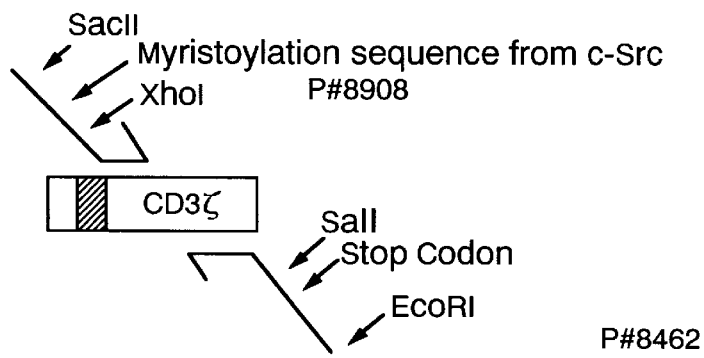
FIG. 2 is a flow diagram or the preparation of the intracellular signaling chimera plasmids p#MXFn and p#MFnZ, where n indicates the number of binding domains.
Figure 2:
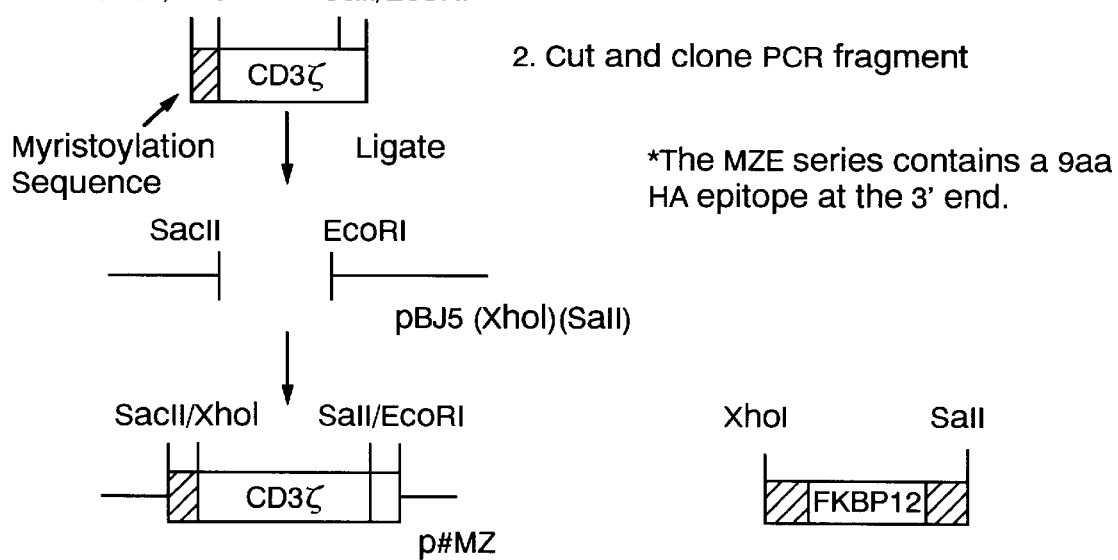
Figure 2:
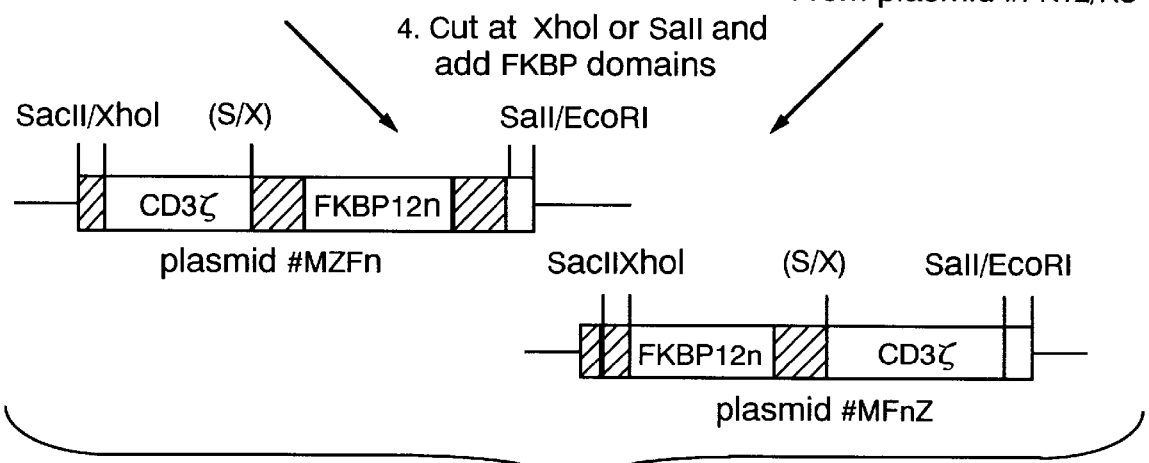
Figure 3A:
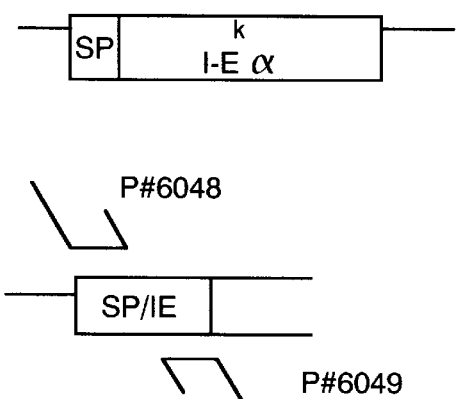
FIGS. 3A and 3B are a flow diagram of the preparation of the extracellular signalling chimera plasmid p#1FK3/pBJ5.
Figure 3A:
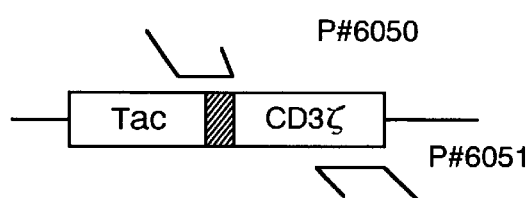
Figure 3A:
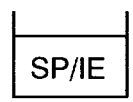
Figure 3A:
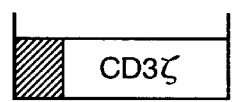
Figure 3A:
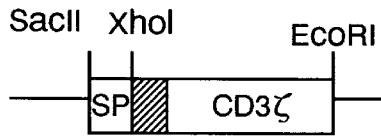
Figure 3B:
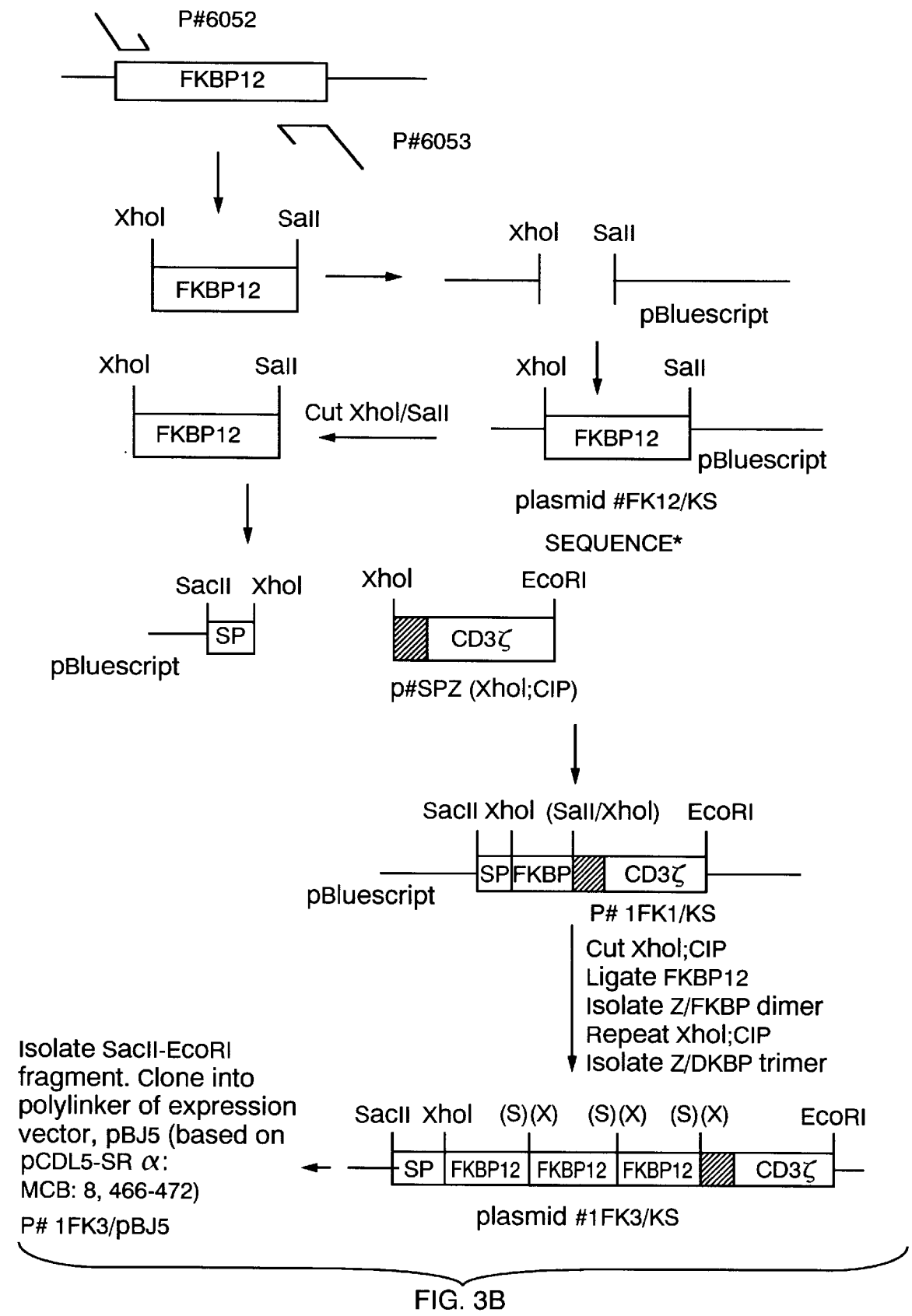
Figure 8:
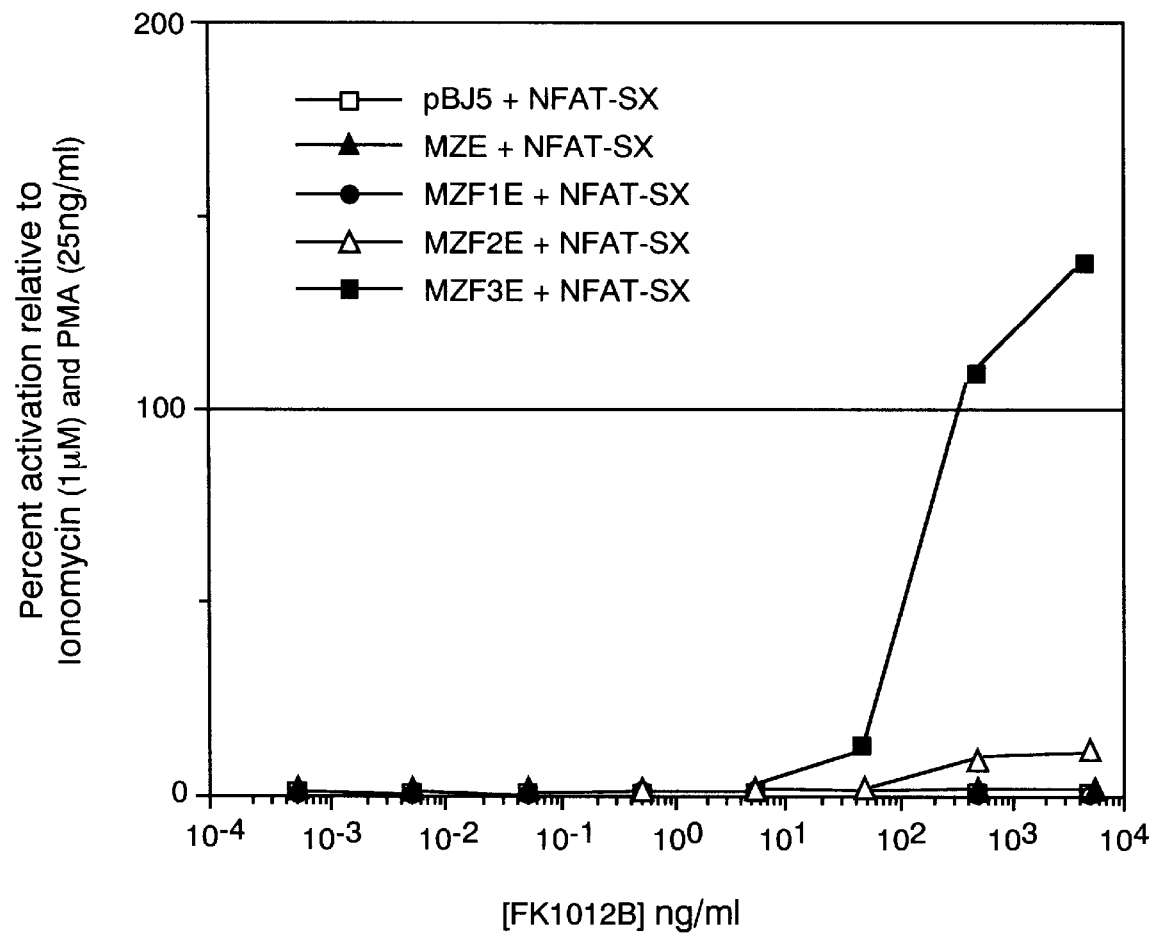
FIG. 8 is a chart of the activation of an NFAT reporter via signalling through a myristoylated CD3ζ/FKBP12 chimera.
Figure 9A:
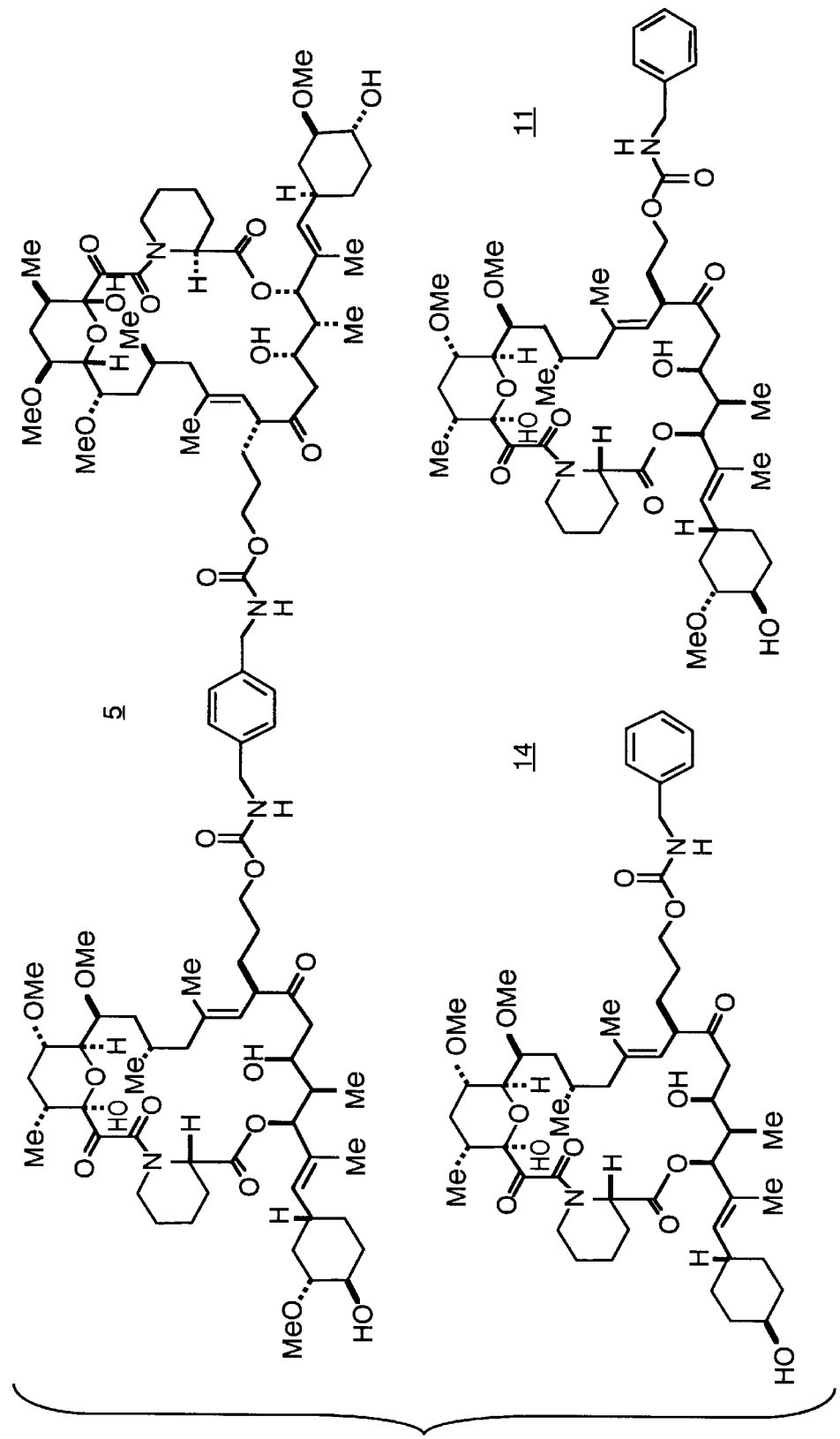
Figure 9B:
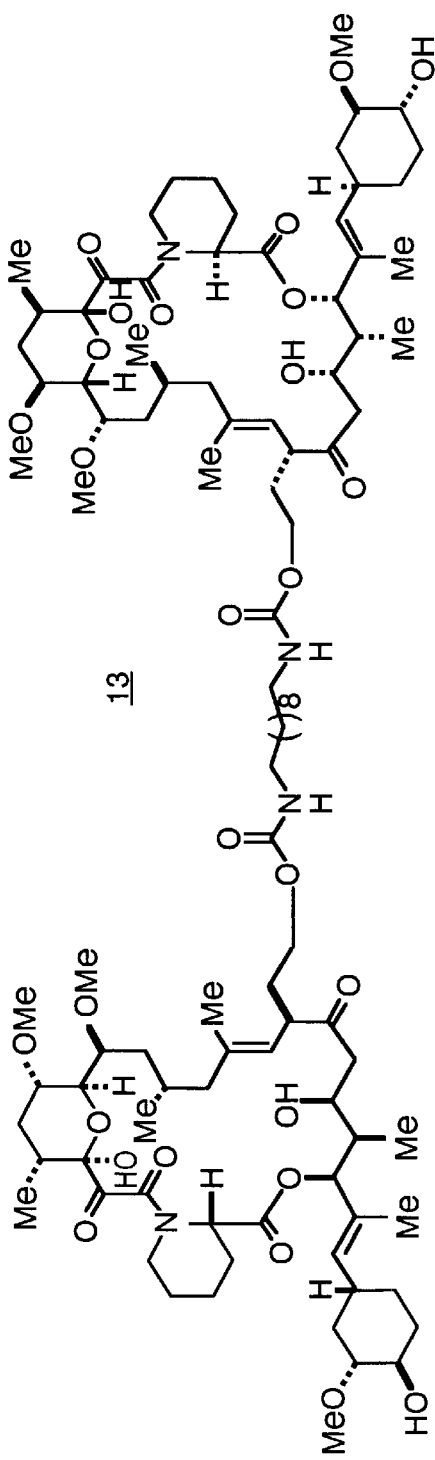
Figure 9B:
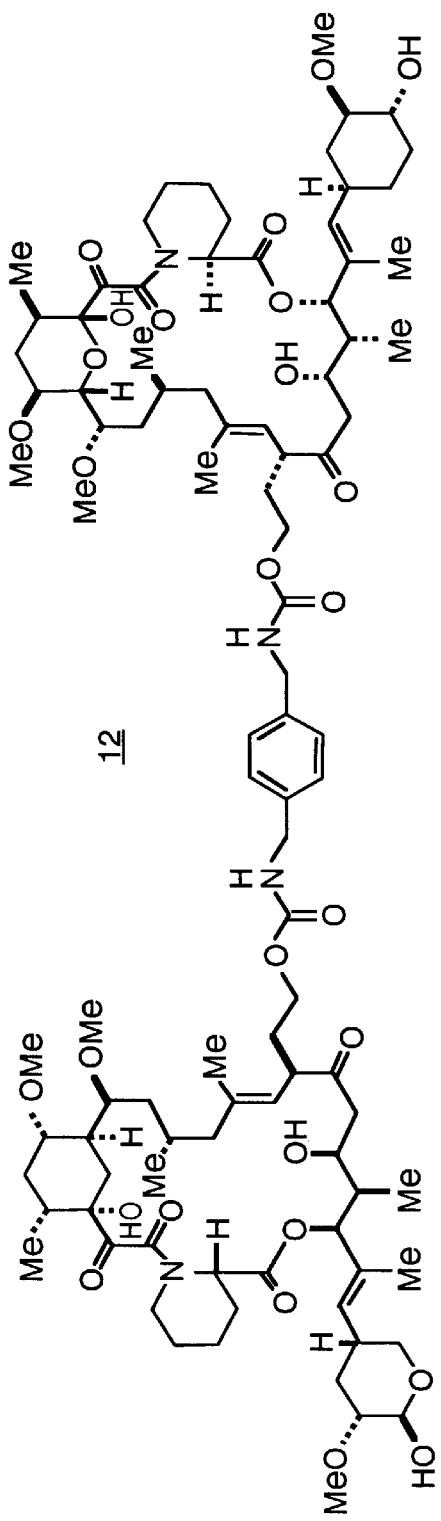
Figure 9C:
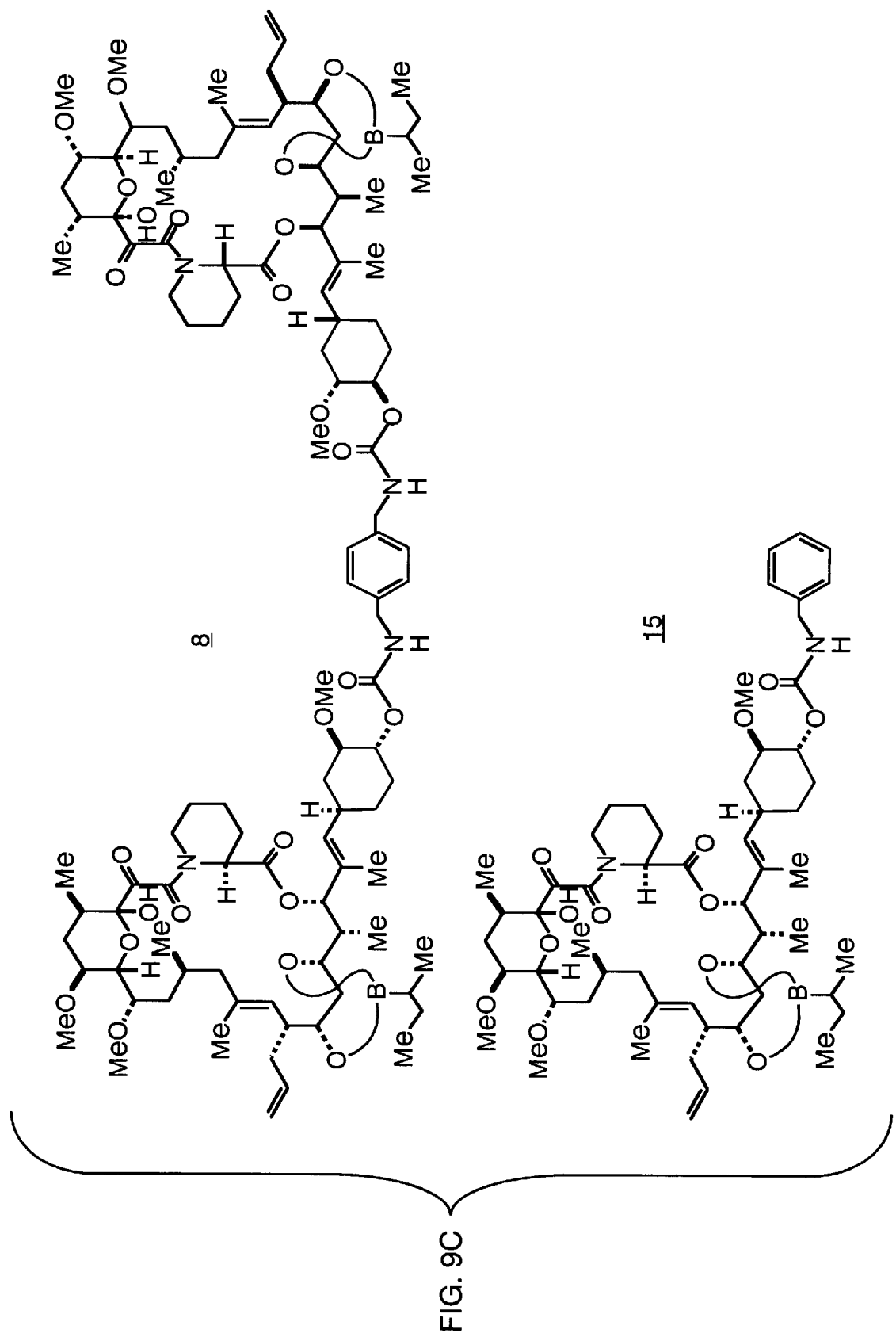
Figure 9D:
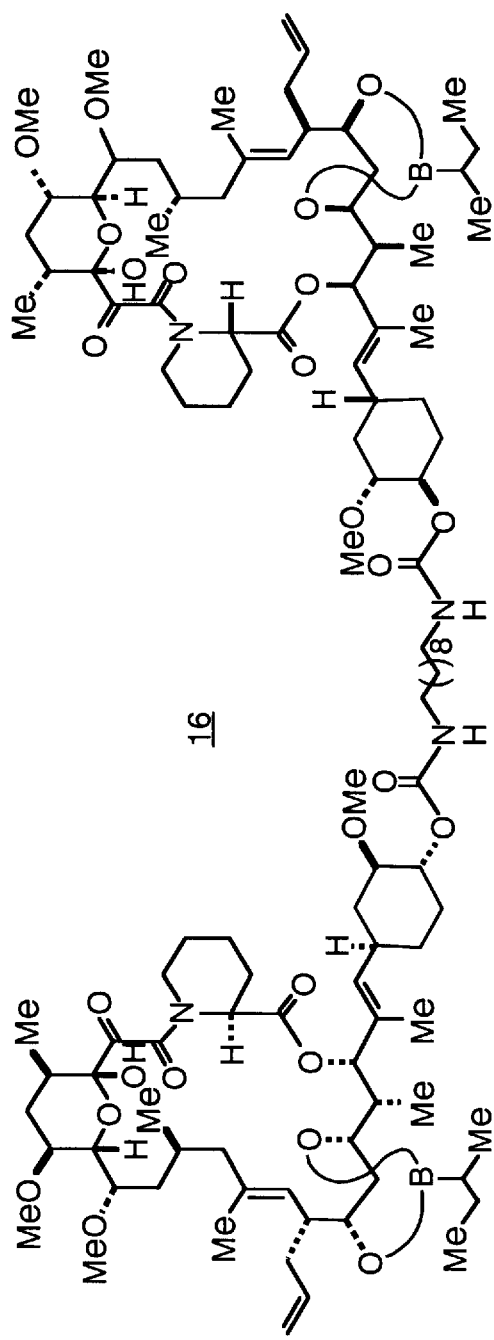
Figure 9D:
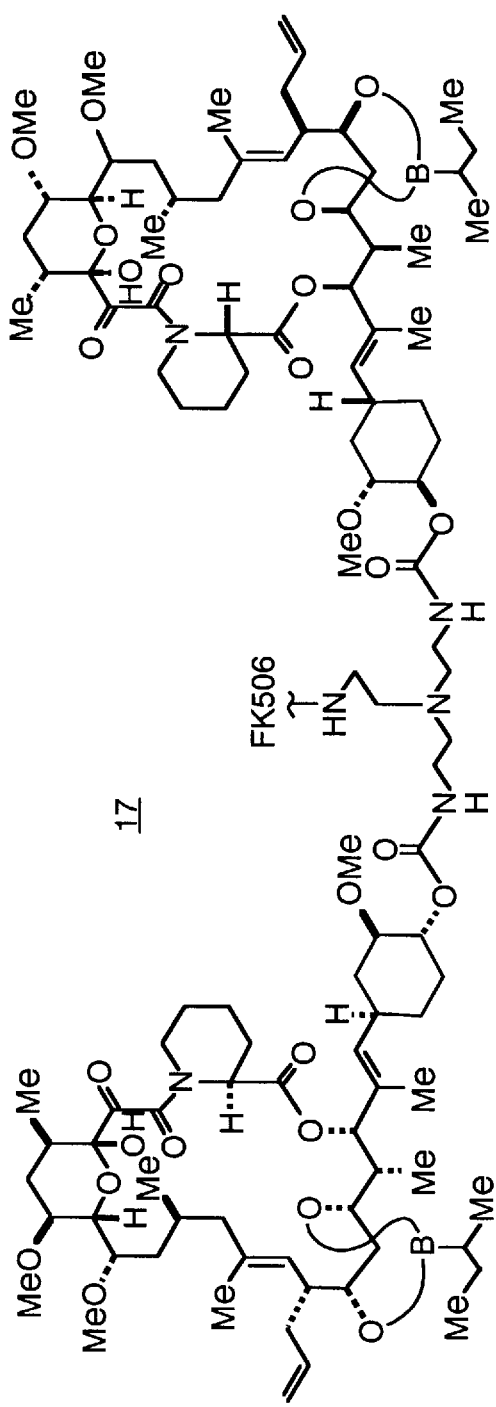
Figure 10:
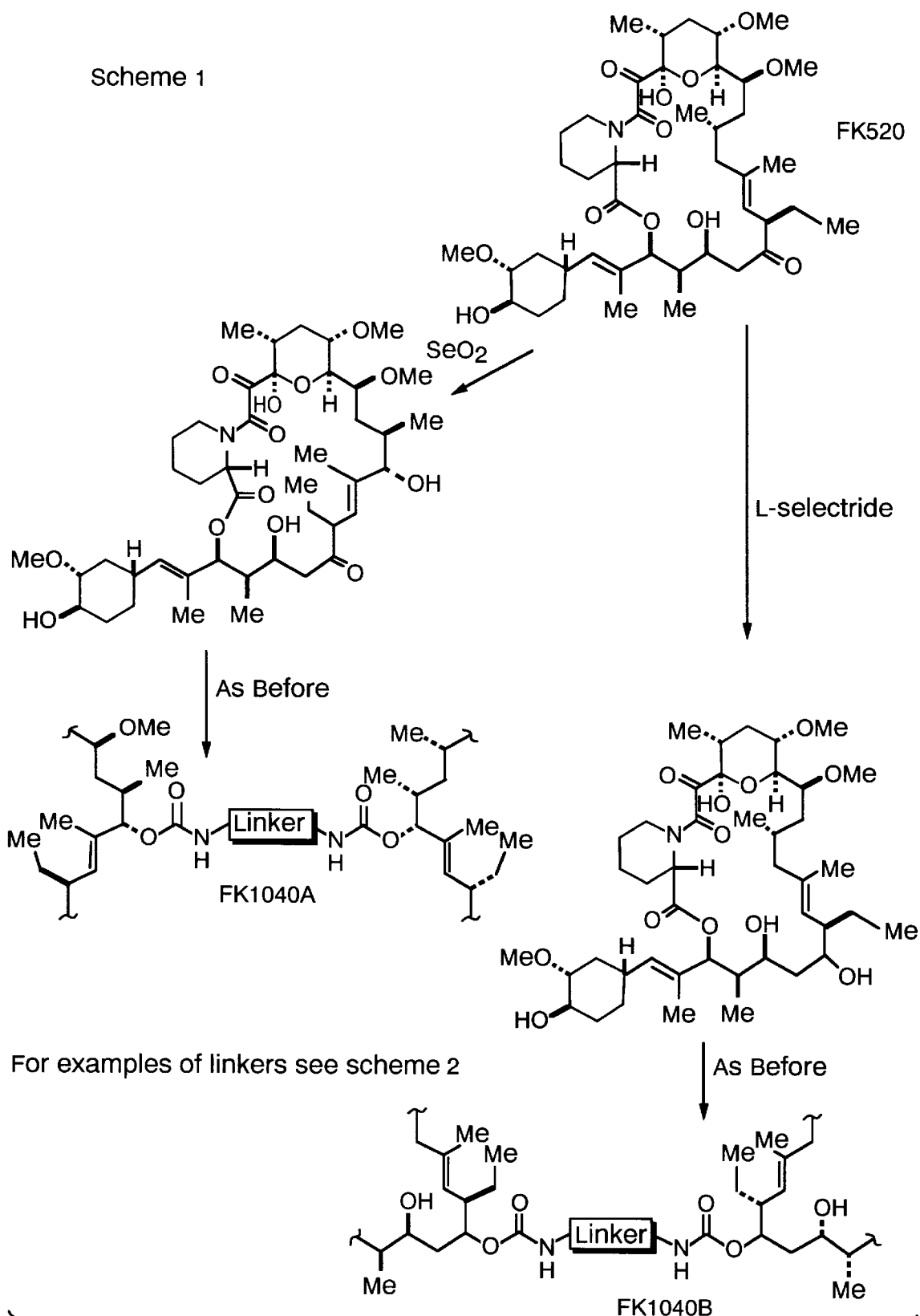
FIG. 10 is a flow diagram of the synthesis of derivatives of FK520.
Figure 11A:
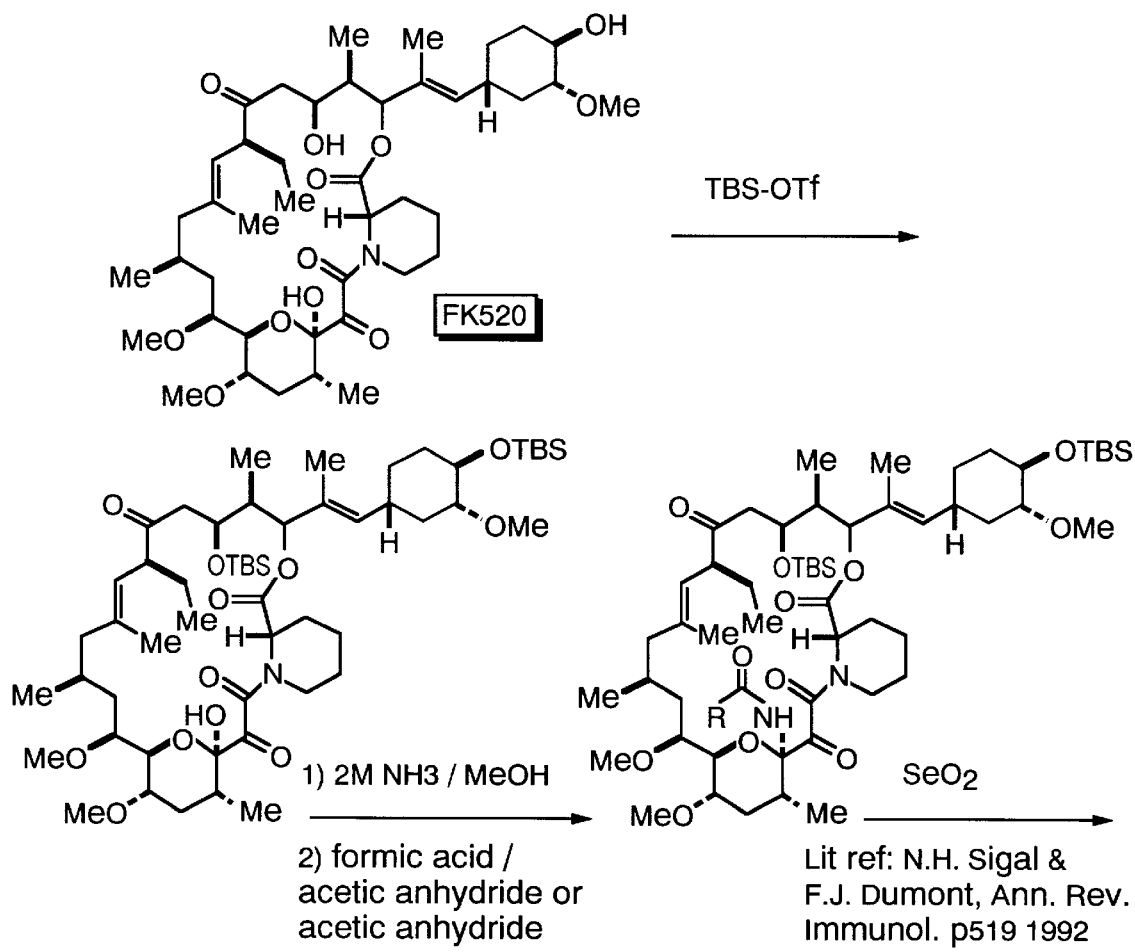
FIGS. 11A and 11C are a flow diagram of a synthesis of derivatives of FK520 and chemical structures of FK520, where the bottom structures are designed to bind to mutant FKBP12.
Figure 11A:
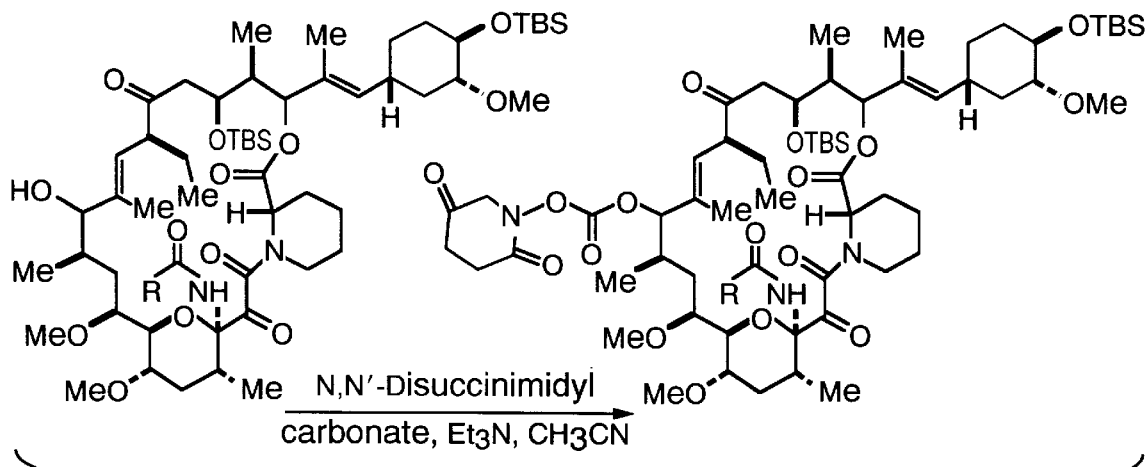
Figure 11B:
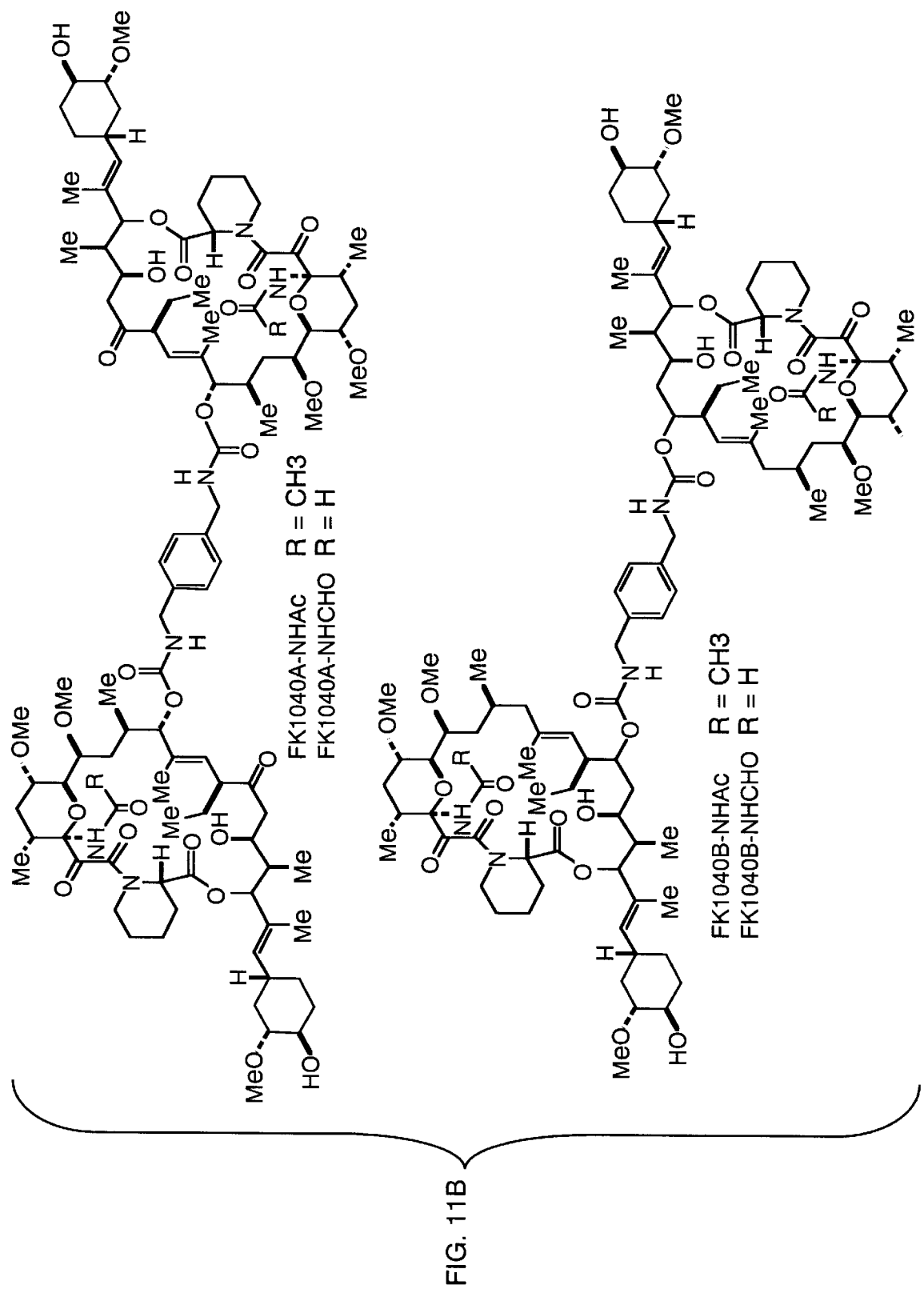
Figure 11C:
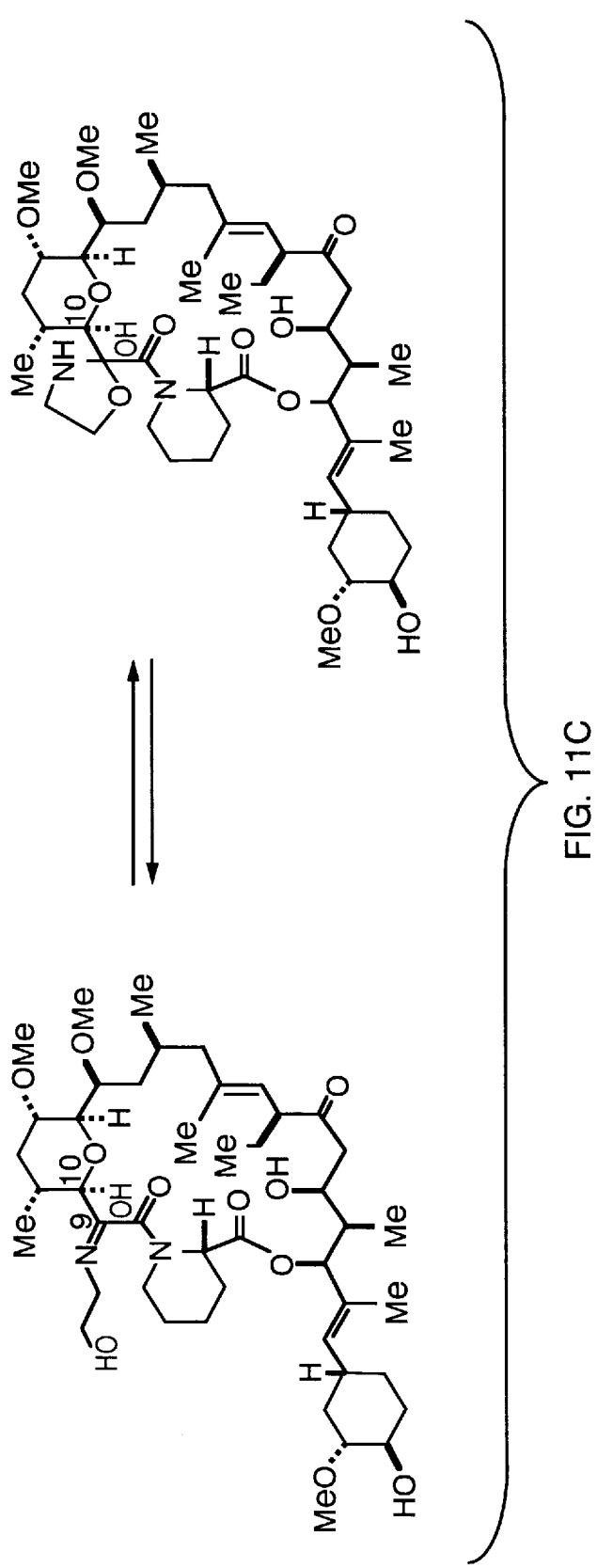
Figure 12:
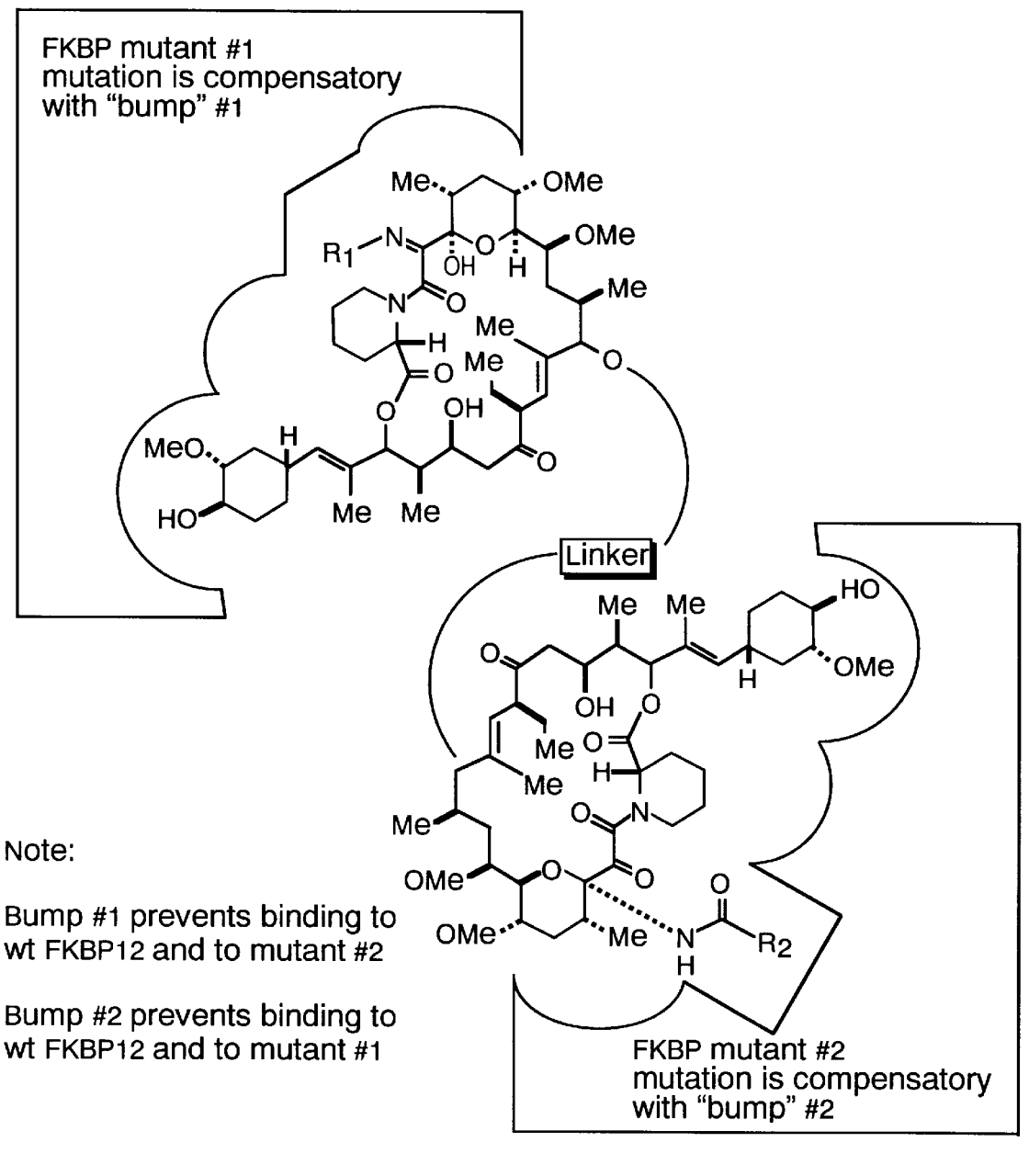
FIG. 12 is a diagrammatic depiction of mutant FKBP with a modified FK520 in the putative cleft.
Figure 13A:
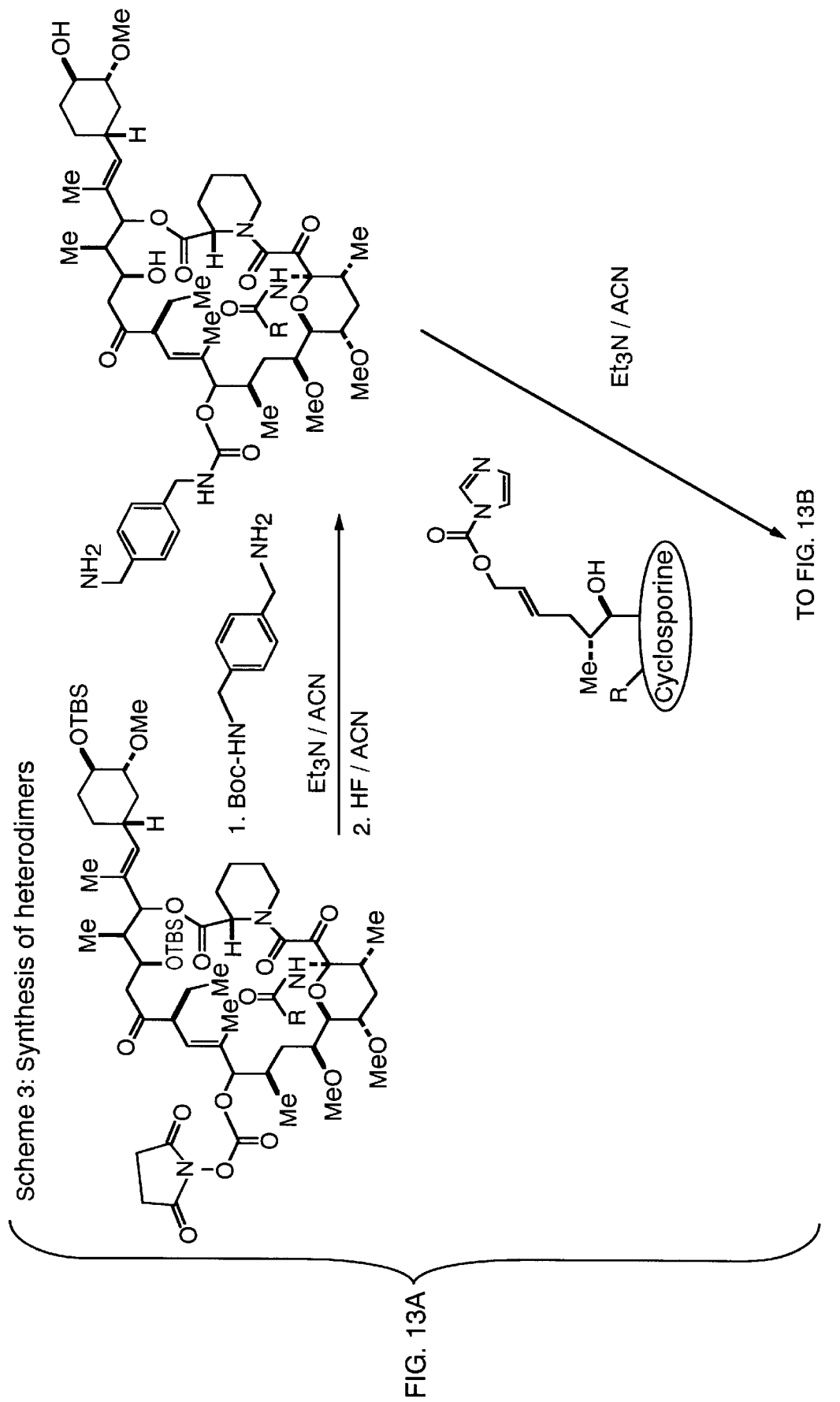
FIG. 13 is a flow diagram of the synthesis of heterodimers of FK520 and cyclosporin.
Figure 13B:
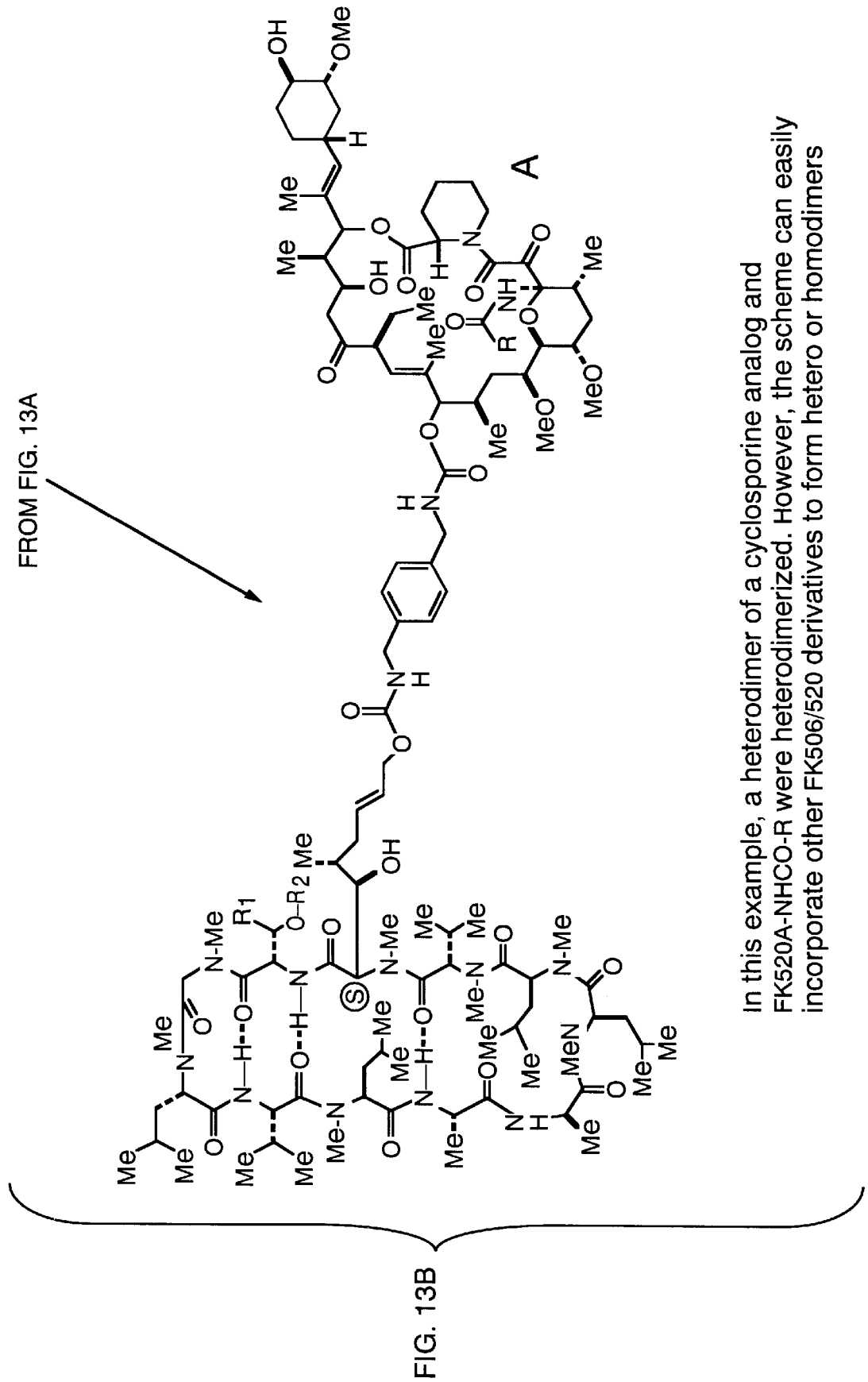

Example 4
Activity of the Dimeric FK506 Derivative, FK1012B, on the Myristoylated Chimeric CD3ζ/FKBP12 (MZF3E) Receptor 5 μg of the eukaryotic expression vector, pBJ5, containing a myristoylated chimeric receptor was co-transfected with 4 μg NFAT-SX. MZE, MZF1E, MZF2E and MZF3E contain 0, 1, 2, or 3 copies of FKBP12, respectively, downstream of a myristoylated CD3ζ cytoplasmic domain (see FIG. 2). As a control, 5 μg of pBJ5 was used in a parallel transfection. After 24 hours, aliquots of each transfection containing approximately $10^5$ cells were incubated with log dilutions of the drug, FK1012B, as indicated. As a positive control and to control for transfection efficiency, ionomycln (1 μm) and PMA (25 ng/ml) were added to aliquots from each transfection. After an additional 12 hour incubation, the supernatants were assayed for alkaline phosphatase activity and these activities were expressed relative to that or the positive control samples. The addition of 1 ng/ml FK506 dropped all stimulations to near background levels, demonstrating that the activations are in the same pathway as that blocked by FK506. This result is further evidence of the reversibility of the subject cell activation. Each data point obtained was the average of two samples and the experiment was performed several times with similar results. See FIG. 8. The myristoylated derivatives respond to lower concentrations of the ligand by about an order of magnitude and activate NF-AT dependent transcription to comparable levels, but it should be noted that the ligands are different. Compare FIGS. 7 and 8.

Example 5
Construction of Murine Signalling Chimeric Protein

Figure 4A:
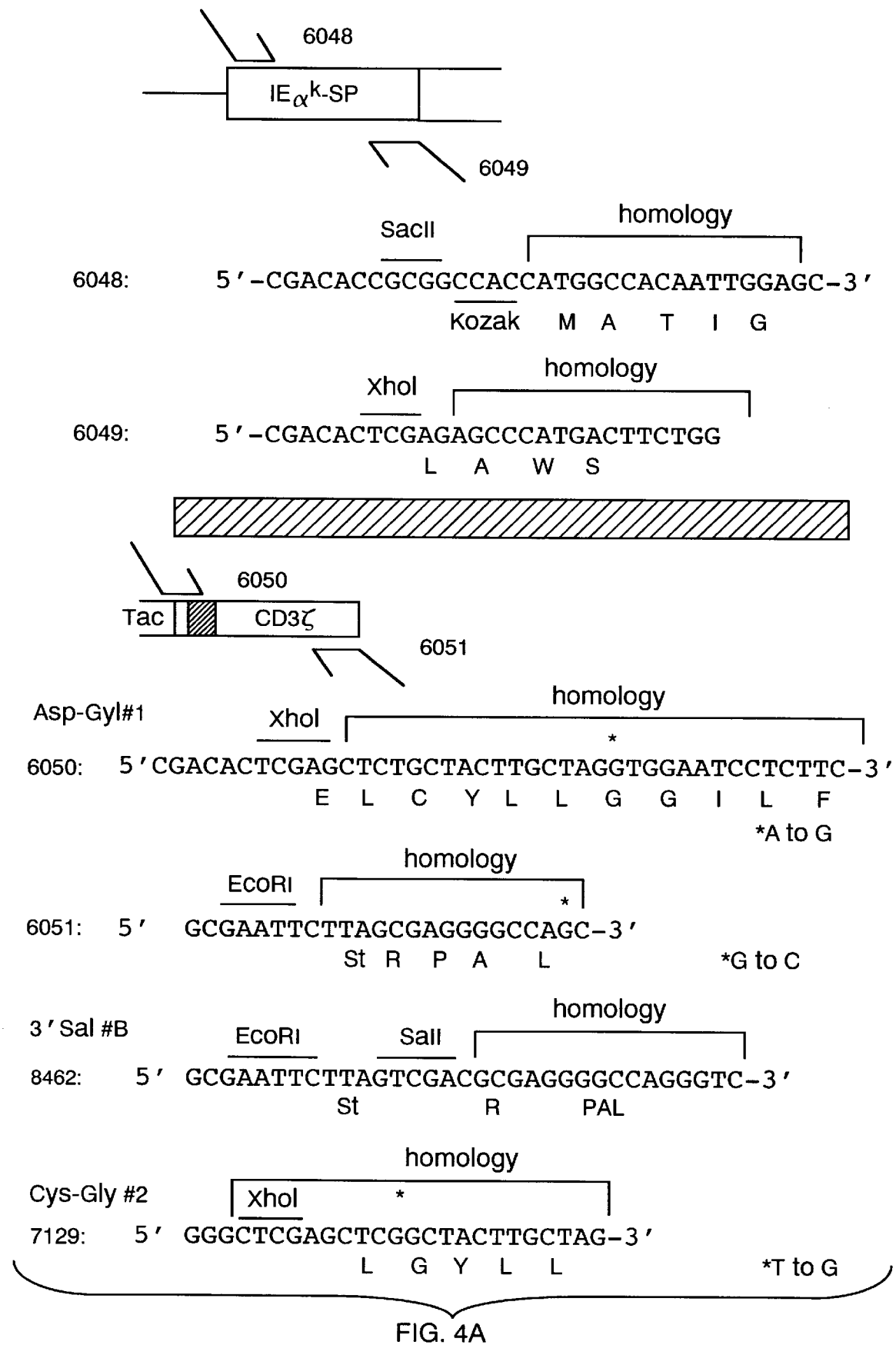
Figure 4C:
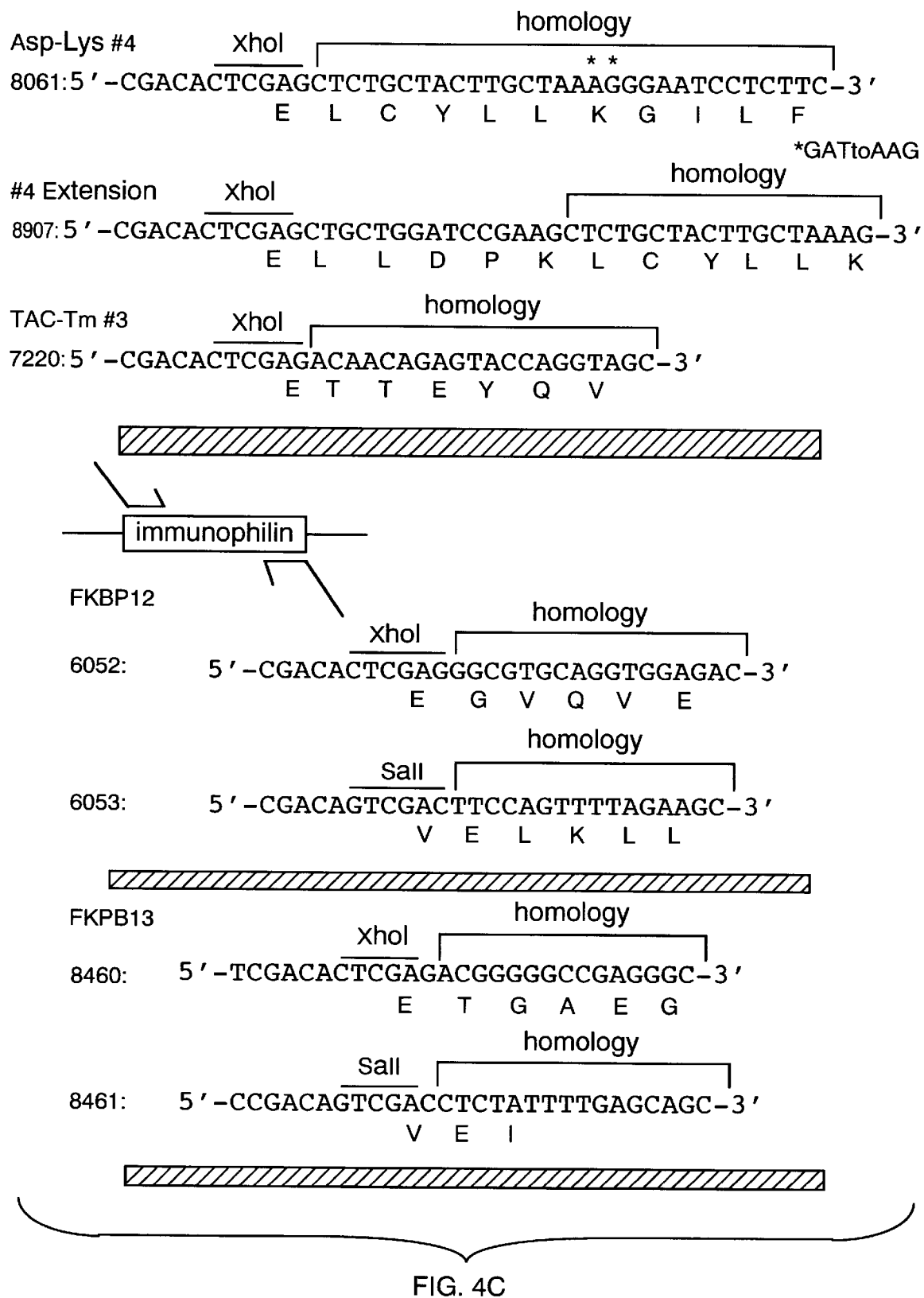

The various fragments were obtained by using primers described in FIG. 4 (SEQ ID NOS. 4 through 40). In referring to primer numbers, reference should be made to FIG. 4.

An approximately 1.2 kb cDNA fragment comprising the I-E$_\alpha$κ chain of the murine class II MHC receptor (Cell, 32, 745) was used as a source of the signal peptide, employing P#6048 (SEQ ID NO. 4) and P#6049 (SEQ ID NO. 6) to give a 70 bp SacII-XhoI fragment using PCR as described by the supplier (Promega). A second fragment was obtained using a plasmid comprising Tac (IL2 receptor α chain) joined to the transmembrane and cytoplasmic domains of CD3ζ (PNAS, 88, 8905). Using P#6050 (SEQ ID NO. 8) and P#6051 (SEQ ID NO. 10), a 320 bp XhoI-EcoRI fragment was obtained by PCR comprising the transmembrane and cytoplasmic domains of CD3ζ. These two fragments were ligated and inserted into a SacII-EcoRI digested pBluescript (Stratagene) to provide plasmid, SPZ/KS.

To obtain the binding domain for FK506, plasmid rhFKBP (provided by S. Schreiber, Nature (1990) 346, 674) was used with P#6052 (SEQ ID NO. 33) and P#6053 (SEQ ID NO. 35) to obtain a 340 bp XhoI-SalI fragment containing human FKBP12. This fragment was inserted into pBluescript digested with XhoI and SalI to provide plasmid FK12/KS, which was the source for the FKBP12 binding domain. SPZ(KS was digested with XhoI, phosphatased (cell intestinal alkaline phosphatase; CIP) to prevent self-annealing, and combined with a 10-fold molar excess of the XhoI-SalI FKBP12-containing fragment from FK12/KS. Clones were isolated that contained monomers, dimers, and timers of FKBP12 an the correct orientation. The clones 1FK1/KS, 1FK2/KS, and 1FK3/KS are comprised of in the direction of transcription; the signal peptide from the murine MHC class II gene I-E$_\alpha$κ, a monomer, dimer or trimer, respectively, of human FKBP12, and the transmembrane and cytoplasmic portions of CD3ζ. Lastly, the SacII-EcoRI fragments were excised from pBluescript using restriction enzymes and ligated into the polylinker of pBJ5 digested with SacII and EcoRI to create plasmids 1FK1/pBJ5, 1FK2/pBJ5, and 1FK3/pBJ5, respectively. See FIGS. 3 and 4.

Example 6

Construction of Intracellular Signaling Chimera

A myristoylation sequence from c-src was obtained from Pellman, et al., *Nature* 314, 374, and joined to a complementary sequence of CD3ζ to provide a primer which was complementary to a sequence 3' of the transmembrane domain, namely P#8908 (SEQ ID NO. 23). This primer has a SacII site adjacent to the 5' terminus and a XhoI sequence adjacent to the 3' terminus of the myristoylation sequence. The other primer P#8462 (SEQ ID NO. 12) has a SalI recognition site 3' of the sequence complementary to the 3' terminus of CD3ζ, a stop codon and an EcoRI recognition site. Using PCR, a 450 bp SacII-EcoRI fragment was obtained, which was comprised of the myristoylation sequence and the CD3' sequence fused in the 5' to 3' direction. This fragment was ligated into SacII/EcoRI-digested pBJ5(XhoI) (SalI) and cloned, resulting (in plasmid MZ/pBJ5. Lastly, MZ/pBJ5 was digested with SalI, phosphatased, and combined with a 10-fold molar excess of the XhoI-SalI FKBP12-containing fragment from FK12/KS and ligated. After cloning, the plasmids comprising the desired constructs having the myristoylation sequence, CD3ζ and FKBP12 multimers in the 5'–3' direction were isolated and verified as having the correct structure. See FIGS. 2 and 4.

Example 7

Construction of Nuclear Chimera

A. GAL4 DNA binding domain—FKBP domain(s)—epitope tag

The GAL4 DNA binding domain (amino acids 1–147) was amplified by PCR using a 5' primer (#37) (SEQ ID NO. 41) that contains a SacII site upstream of a Kozak sequence and a translational start site, and a 3', primer (#38) (SEQ ID NO. 42) that contains a SalI site. The PCR product was isolated, digested with SacII and SalI, and ligated into pBluescript II KS (+) at the SacII and SalI Sites, generating the construct pBS-GAL4. The construct was verified by sequencing. The SacII/SalI fragment from pBS-GAL4 was isolated and ligated into the 7FK1/pBJ5 and IFK3/pBJ5 constructs (containing the myristoylation sequence, see Example 6) at the SacII and XhoI sites, generating constructs GF1E, GF2E and GF3E.

5' end of PCR amplified product (SEQ ID NOS. 43 and 44):

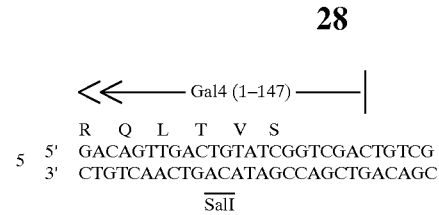

```
                                 M  K  L  L  S  S  I
5'  CGACACCGCGGCCACCATGAAGCTACTGTCTTCTATCG
         Kozak
```

3' end of PCR amplified product (SEQ ID NOS. 45 and 46):

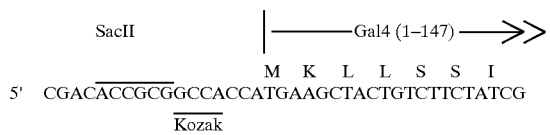

```
       R  Q  L  T  V  S
5'  GACAGTTGACTGTATCGGTCGACTGTCG
3'  CTGTCAACTGACATAGCCAGCTGACAGC
                         SalI
```

B. HNF1 dimerization/DNA binding domain—FKBP domain(s)—tag

The HNF1a dimerization/DNA binding domain (amino acids 1–282) was amplified by PCR using a 5' primer (#39) (SEQ ID NO. 47) that contains a SacII site upstream of a Kozak sequence and a translational start site, and a 3' primer (X#40) (SEQ ID NO. 48) that contains a SalI site. The PCR product was isolated, digested with SacII and SalI, and ligated into pBluescript II KS (+) at the SacII and SalI sites, generating the construct pBS-HNF. The construct was verified by sequencing. The SacII/SalI fragment from pBS-HNF was isolated and ligated into the IFK1/pBJ5 and IFK3/pBJ5 constructs at the SacII and XhoI sites, generating constructs HF1E, HF2E and HF3E.

5' end of PCR amplified product (SEQ ID NOS. 49 and 50):

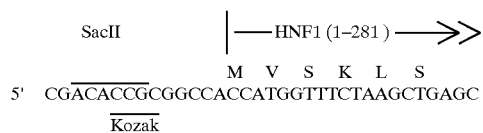

```
                      M  V  S  K  L  S
5'  CGACACCGCGGCCACCATGGTTTCTAAGCTGAGC
         Kozak
```

3' end of PCR amplified product (SEQ ID NOS. 51 and 52):

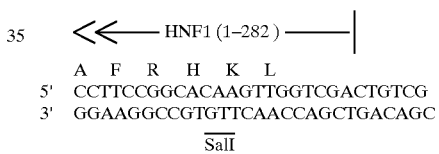

```
       A  F  R  H  K  L
5'  CCTTCCGGCACAAGTTGGTCGACTGTCG
3'  GGAAGGCCGTGTTCAACCAGCTGACAGC
                         SalI
```

C. FKBP domain(s)-VP16 transcrip. activation domain(s)-epitope tag

These constructs were made in three steps: (i) a construct was created from IFK3/pBJ5 in which the myristoylation sequence was replaced by a start site immediately upstream of an XhoI site, generating construct SF3E; (ii) a nuclear localization sequence was inserted into the XhoI site, generating construct NF3E; (iii) the VP16 activation domain was cloned into the SalI site of NF3E, generating construct NF3V1E.

(i). Complementary oligonucleotides (#45 (SEQ ID NO. 53) and #46 (SEQ ID NO. 55)) encoding a Kozak sequence and start site flanked by SacII and XhoI sites were annealed, phosphorylated and ligated into the SacII and XhoI site of MF3E, generating construct SF3E.

Insertion of generic start site (SEQ ID NOS. 53 through 55)

```
           Kozak
                  M  L  E
5'      GGCCACCATGC
3'      CGCCGGTGGTACGAGCT
        SacII       XhoI
        overhang    overhang
```

(ii). Complementary oligonucleotides (#47 (SEQ ID NO. 56) and #48(SEQ ID NO. 57)) encoding the SV40 T antigen nuclear localization sequence flanked by a 5' SalI site and a 3' XhoI site were annealed, phosphorylated and ligated into the XhoI site of SF1E, generating the construct NF1E. The construct was verified by DNA sequencing. A construct containing the mutant or defective form of the nuclear localization sequence, in which a threonine is substituted for the lysine at position 128, was also isolated. This is designated NF1E-M. Multimers of the FKBP12 domain were obtained by isolating the FKBP12 sequence as an XhoI/SalI fragment from pBS-FKBP12 and ligating this fragment into NF1E linearized with XhoI. This resulted in the generation of the constructs NF2E and NF3E.

Insertion of NLS into generic start site (SEQ ID NOS. 58 through 60)

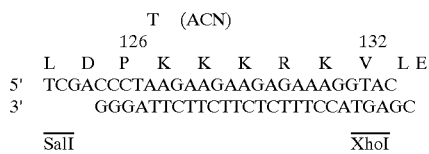

Threonine at position 128 results in a defective NLS.

(iii). The VP16 transcriptional activation domain (amino acids 413–490) was amplified by PCR using a 5' primer (#43) (SEQ ID NO. 61) that contains SalI site and a 3' primer (#44) (SEQ ID NO. 62) that contains an XhoI site. The PCR product was isolated, digested with SalI and XhoI, and ligated into MF3E at the XhoI and SalI sites, generating the construct MV1E. The construct was verified by sequencing. Multimerized VP16 domains were created by isolating the single VP16 sequence as a XhoI/SalI fragment from MV1E and ligating this fragment into MV1E linearized with XhoI. Constructs MV2E, MV3E and MV4E were generated in this manner. DNA fragments encoding one or more multiple VP16 domains were isolated as XhoI/SalI fragments from MV1E or MV2E and ligated into NF1E linearized with SalI, generating the constructs NF1V1E and NF1V3E. Multimers of the FKBP12 domain were obtained by isolating the FKBP12 sequence as an XhoI/SalI fragment from pBS-FKBP12 and ligating this fragment into NF1V1E linearized with XhoI. This resulted in the generation of the constructs NF2V1E and NF3V1E.

5' end of PCR amplified product (SEQ ID NOS. 63 and 64):

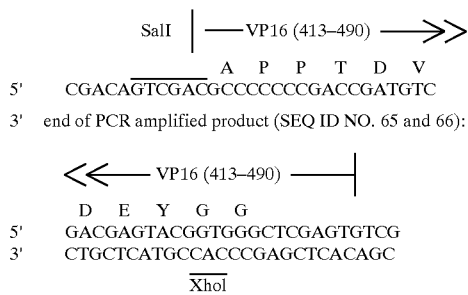

oligonucleotides
37 (SEQ ID NO. 41) 38mer/0.2 um/OFF 5'CGACAC-CGCGGCCACCATGAAGCTACTGTCTTC TATCG
38 (SEQ ID NO. 42) 28mer/0.2 um/OFF 5'CGACAGTC-GACCGATACAGTCAACTGTC
39 (SEQ ID NO. 47) 34mer/0.2 um/OFF 5'CGACAC-CGCGGCCACCATGGTTTCTAAGCTGAGC
40 (SEQ ID NO. 48) 28mer/0.2 um/OFF 5'CGACAGTC-GACCAACTTGTGCCGGAAGG

43 (SEQ ID NO. 61) 29mer/0.2 um/OFF 5'CGACAGTC-GACGCCCCCCCGACCGATGTC
44 (SEQ ID NO. 62) 26mer/0.2 um/OFF 5'CGACACTC-GAGCCCACCGTACTCGTC
45 (SEQ ID NO. 53) 26mer/0.2 um/OFF 5'GGCCAC-CATGC
46 (SEQ ID NO. 55) 18mer/0.2 um/OFF 5'TCGAGCATG-GTGGCCGC
47 (SEQ ID NO. 56) 27mer/0.2 um/OFF 5'TCGACCCTAAGA-(C/A)-GAAGAGAAAGGTAC
48 (SEQ ID NO. 57) 27mer/0.2 um/OFF 5'TCGAGTACCTTTCTCTLC-(G/T)-TCTTAGGG Example 8
Demonstration of Transcriptional Induction Jurkat TAg cells were transfected with the indicated constructs (5 μg of each construct) by electroporation (960 μF, 250 v). After 24 hours, the cells were resuspended in fresh media and aliquoted. Half of each transfection was incubated with the dimeric FK506 derivative, (Example 14) at a final concentration of 1 μM. After 12 hours, the cells were washed and cellular extracts were prepared by repeated freeze-thaw. Chloramphenicol acetyltransferase (CAT) activity was measured by standard protocols. Molecular Cloning: A Laboratory Manual, Sambrook et al. ads. (1989) CSH Laboratory, pp. 16–59 ff. The data demonstrates CAT activity present in 70 μL of extract (total extract volume was 120 μL) after incubation at 37° C. for 18 hours. The following are the different samples which were assayed.

1. G5E4TCAT (GAL4-CAT reporter plasmid)
2. G5E4TCAT, GAL4-VP16
3. G5E4TCAT, NF3V1E
4. G5E4TCAT, GF2E
5. G5E45CAT, GF2E, NF3V1E
6. G5E4TCAT, GF3E, NF3V1E Preparation of FK506 Derivatives A. General Procedures All reactions were performed in oven-dried glassware under a positive pressure of nitrogen or argon. Air and moisture sensitive compounds were introduced via syringe or cannula through a rubber septum.

B. Physical Data

Proton magnetic resonance spectra ($^1$H NMR) were recorded on Bruker AM-500 (500 MHz), and AM-400 (400 MHz) spectrometers. Chemical shifts are reported in ppm from tetramethylsilane using the solvent resonance as an internal standard (chloroform, 7.27 ppm). Data are reported as follows: chemical shift, multiplicity (s=singlet, d=doublet, t=triplet, q=quartet, br=broadened, m=multiplet), coupling constants (Hz), integration. Low and high-resolution mass spectra were obtained.

C. Chromatography

Reactions were monitored by thin layer chromatography (TLC) using E. Merck silica gel 60F glass plates (0.25 mm). Components were visualized by illumination with long wave ultraviolet light, exposed to iodine vapor, and/or by dipping in an aqueous ceric ammonium molybdate solution followed by heating. Solvents for chromatography were HPLC grade. Liquid chromatography was performed using forced flow (flash chromatography) of the indicated solvent system on E. Merck silica gel 60 (230–400 mesh).

D. Solvents and Reagents

All reagents and solvents were analytical grade and were used as received with the following exceptions. Tetrahydrofuran (THF), benzene, toluene, and diethyl ether were distilled from sodium metal benzophenone ketyl. Triethylamine and acetonitrile were distilled from calcium hydride. Dichloromethane was distilled from phosphorous pentoxide. Dimethylformamide (DMF) was distilled from calcium hydride at reduced pressure and stored over 4 Å molecular sieves.

Example 9

Hydroboration/Oxidation of FK506-TBS$_2$ (1 to 2)

The hydroboration was performed according to the procedure of Evans (Evans, et al., *JACS* (1992) 114, 6679; ibid. (1992) 6679–6685). (See Harding, et al., *Nature* (1989) 341, 758 for numbering.) A 10-mL flask was charged with 24,32-bis[(tert-butyldimethylsilyl)oxy]-FK506 (33.8 mg, 0.033 mmol) and [Rh(nbd)(diphos-4)]BF$_4$(3.1 mg, 0.004 mmol, 13 mol %). The orange mixture was dissolved in toluene (2.0 mL) and the solvent was removed under reduced pressure over four hours. The flask was carefully purged with nitrogen and the orangish oil was dissolved in THF (3.0 mL, 10 mM final concentration) and cooled to 0° C. with an ice water bath. Catecholborane (98 μL, 0.098 mmol, 1.0M solution in THF, 3.0 equiv.) was added via syringe and the resulting solution was stirred at 0° C. for 45 min. The reaction was quenched at 0° C. with 0.2 mL of THF/EtOH (1:1) followed by 0.2 mL of pH 7.0 buffer (Fisher; 0.05M phosphate) then 0.2 mL of 30% H$_2$O$_2$. The solution was stirred at room temperature for at least 12 h. The solvent was removed under reduced pressure and the remaining oil was dissolved in benzene (10 mL) and washed with saturated aqueous sodium bicarbonate solution (10 mL). The phases were separated and the aqueous phase was back-extracted with benzene (2×10 mL). The organic phases were combined and washed once with saturated aqueous sodium bicarbonate solution (10 mL). The benzene phase was dried with MGSO$_4$, concentrated, and subjected to flash chromatography (2:1 hexane:ethyl acetate) providing the desired primary alcohol as a clear, colorless oil (12.8 mg, 0.012 mmol, 37%).

Preparation of Mixed Carbonate (2 to 3)

The preparation of the mixed carbonate was accomplished by the method of Ghosh (Ghosh, et al., *Tetrahedron Lett.* (1992) 33, 2781–2784). A 10-mL flask was charged with the primary alcohol (29.2 mg, 0.0278 mmol) and benzene (4 mL). The solvent was removed under reduced pressure over 60 min. The oil was dissolved in acetonitrile (2.0 mL, 14 mM final concentration) and stirred at 20° C. as triethylamine (77 μL, 0.56 mmol) was added. N,N'-disuccinimidyl carbonate (36 mg, 0.14 mmol) was added in one portion and the solution was stirred at 20° C. for 46 h. The reaction mixture was diluted with dichloromethane and washed with saturated aqueous sodium bicarbonate solution (10 mL). The phases were separated and the aqueous layer was back-extracted with dichloromethane (2×10 mL). The organic phases were combined and dried (MgSO$_4$), concentrated, and subjected to flash chromatography (3:1 to 2:1 to 1:1 hexane:ethyl acetate). The desired mixed carbonate was isolated as a clear, colorless oil (16.8 mg, 0.014 mmol, 51%).

Dimerization of FK506 (3 to 4)

A dry, 1-mL conical glass vial (Kontes Scientific Glassware) was charged with the mixed carbonate (7.3 mg, 0.0061 mmol) and acetonitrile (250 μL, 25 mM final concentration). Triethylamine (10 μL, 0.075 mmol) was added followed by p-xylylenediamine (8.3 μL, 0.0027 mmol, 0.32M solution in DMF). The reaction stirred 22 h at 20° C. and was quenched by dilution with dichloromethane (10 mL). The solution was washed with saturated aqueous sodium bicarbonate solution (10 mL). The phases were separated and the aqueous layer was back-extracted with dichloromethane (2×10 mL). The organic phases were combined and dried (MgSO$_4$), concentrated, and subjected to flash chromatography (3:1 to 2:1 to 1:1 hexane:ethyl acetate) providing the desired protected dimer as a clear, colorless oil (4.3 mg, 1.9 μmol, 70%).

Deprotection of the FK506 Dimer (4 to 5)

The protected dimer 3.3 mg, 1.4 μmol) was placed in a 1.5-mL polypropylene tube fitted with a spin vane. Acetonitrile (0.5 mL, 3 mM final concentration) was added and the solution stirred at 20° C. as HF (55 μL, 48% aqueous solution; Fisher) was added. The solution was stirred 18 h at room temperature. The deprotected FK506 derivative was then partitioned between dichloromethane and saturated aqueous sodium bicarbonate in a 15-mL test tube. The tube was vortexed extensively to mix the phases and, after separation, the organic phase was removed with a pipet. The aqueous phase was back-extracted with dichloromethane (4×2 mL), and the combined organic phases were dried (MgSO$_4$), concentrated and subjected to flash chromatography (1:1:1 hexane:THF:ether to 1:1 THF:ether) providing the desired dimer as a clear, colorless oil (1.7 mg, 0.93 μmol, 65%).

Following the above procedure, other monoamines and diamines may be used, such as benzylamine (14) octamethylenediamine, decamethylenediamine, etc.

Example 10

Reduction of FK506 with L-Selectride (FK506 to 6)

Danishefsky and coworkers have shown that the treatment of FK506 with L-Selectride provides 22-dihydro-FK506 with a boronate ester engaging the C24 and C22 hydroxyl groups (Coleman and Danishefsky, *Heterocycles* (1989) 28, 157–161; Fisher, et al., *J. Org. Chem.* (1991) 56, 2900–2907).

Preparation of the Mixed Carbonate (6 to 7)

A 10-mL flask was charged with 22-dihydro-FK506-sec-butylboronate (125.3 mg, 0.144 mmol) and acetonitrile (3.0 mL, 50 mM final concentration) and stirred at room temperature as triethylamine (200 μL, 1.44 mmol, 10 equiv.) was added to the clear solution. N,N'-disuccinimidyl carbonate (184.0 mg, 0.719 mmol) was added in one portion, and the clear solution was stirred at room temperature for 44 h. The solution was diluted with ethyl acetate (20 mL) and washed with saturated aqueous sodium bicarbonate (10 mL) and the phases were separated. The aqueous phase was then back-extracted with ethyl acetate (2×10 mL), and the organic phases were combined, dried (MgSO$_4$), and the resulting oil was subjected to flash chromatography (1:1 to 1:2 hexane:ethyl acetate) providing the desired mixed carbonate as a clear, colorless oil (89.0 mg, 0.088 mmol, 61%).

Dimerization of FK506 Mixed Carbonate (7 to 8)

A dry, 1-mL conical glass vial (Kontes Scientific Glassware) was charged with the mixed carbonate (15.0 mg, 0.0148 mmol) and dichloromethane (500 μL, 30 mM final concentration). The solution was stirred at room temperature as triethylamine (9 μL, 0.067 mmol, 10 equiv.) was added followed by p-xylylenediamine (0.8 mg, 0.0059 mmol). The reaction stirred 16 h at 20° C. and was quenched by dilution with dichloromethane (5 mL). The solution was washed with saturated aqueous sodium bicarbonate solution (5 mL). The phases were separated and the aqueous layer was back-extracted with dichloromethane (2×5 mL). The organic phases were combined and dried (MgSO$_4$), concentration, and subjected to flash chromatography (1:1 to 1:2 hexane:ethyl acetate) providing the desired dimer as a clear, colorless oil (7.4 mg, 3.8 μmol, 65%).

Following the above procedure, other, monoamines, diamines or triamines may be used in place of the xylylenediamine, such as benzylamine (15), octylenediamine, decamethylenediamine (16), bis-p-dibenzylamine, N-methyl diethyleneamine, tris-aminoethylamine (17), trisaminopropylamine, 1,3,5-triaminomethylcyclohexane, etc.

Example 11
Oxidative Cleavage and Reduction of FK506 (1 to 9)

The osmylation was performed according to the procedure of Kelly (VanRheenen, et al., *Tetrahedron Lett.* (1976) 17, 1973–1976). The cleavage was performed according to the procedure of Danishefsky (Zell, et al., *J. Org. Chem.* (1986) 51, 5032–5036). The aldehyde reduction was performed according to the procedure of Krishnamurthy (*J. Org. Chem.*, (1981) 46, 4628–4691). A 10 mL flask was charged with 24,32-bis[tert-butyldimethylsilyl)oxy]-FK506 (84.4 mg, 0.082 mmol), 4-methylmorpholine N-oxide (48 mg, 0.41 mmol, 5 equiv), and THF (2.0 mL, 41 mM final concentration). Osmium tetroxide (45 $\mu$L, 0.008 mmol, 0.1 equiv) was added via syringe. The clear, colorless solution was stirred at room temperature for 5 hr. The reaction was then diluted with 50% aqueous methanol (1.0 mL) and sodium periodate (175 mg, 0.82 mmol, 10 equiv) was added in one portion. The cloudy mixture was stirred 40 min at room temperature, diluted with ether (10 mL), and washed with saturated aqueous sodium bicarbonate solution (5 mL). The phases were separated and the aqueous layer was back-extracted with ether (2×5 mL). The combined organic layers were dried (MgSo$_4$) and treated with solid sodium sulfite (50 mg). The organic phase was then filtered and concentrated and the oil was subjected to flash chromatography (3:1 to 2:1 hexane:ethyl acetate) providing the intermediate, unstable aldehyde (53.6 mg) as a clear, colorless oil. The aldehyde was immediately dissolved in THF (4.0 mL) and cooled to −78° C. under an atmosphere of nitrogen, and treated with lithium tris[(3-ethyl-3-pentyl)oxy]aluminum hydride (0.60 mL, 0.082 mmol, 0.14M solution in THF, 1.0 equiv). The clear solution was allowed to stir for 10 min at −78° C. then quenched by dilution with ether (4 mL) and addition of saturated aqueous ammonium chloride (0.3 mL). The mixture was allowed to warm to room temperature and solid sodium sulfate was added to dry the solution. The mixture was then filtered and concentrated and the resulting oil was subjected to flash chromatography (2:1 hexane:ethyl acetate) giving the desired alcohol as a clear, colorless oil (39.5 mg, 0.038 mmol, 47%).

Preparation of Mixed Carbonate (9 to 10)

The preparation of the mixed carbonate was accomplished by the method of Ghosh, et al., *Tetrahedron Lett.* (1992) 33, 2781–2784). A 10 mL flask was charged with the primary alcohol (38.2 mg, 0.0369 mmol) and acetonitrile (2.0 mL, 10 mM final concentration) and stirred at room temperature as 2,6-lutidine (43 $\mu$L, 0.37 mmol, 10 equiv) was added. N,N'-disuccinimidyl carbonate (48 mg, 0.18 mmol) was added in one portion and the solution was stirred at room temperature for 24 h. The reaction mixture was diluted with ether (10 mL) and washed with saturated aqueous sodium bicarbonate solution (10 mL). The phases were separated and the aqueous layer was back-extracted with ether (2×10 mL). The organic phases were combined and dried (MgSO$_4$), concentrated, and subjected to flash chromatography (2:1 to 1:1 hexane:ethyl acetate). The desired mixed carbonate was isolated as a clear, colorless oil (32.6 mg, 0.028 mmol, 75%).

Preparation of Benzyl Carbamate (10 to 11)

A dry, 1 mL conical glass vial (Kontes Scientific Glassware) was charged with the mixed carbonate 10 (8.7 mg, 0.0074 mmol) and acetonitrile (500 $\mu$L, 15 mM final concentration). The solution was stirred at room temperature as triethylamine (10 $\mu$L, 0.074 mmol, 10 equiv) was added followed by benzylamine (1.6 $\mu$L, 0.015 mmol, 2 equiv). The reaction stirred 4 h at room temperature. The solvent was removed with a stream of dry nitrogen and the oil was directly subjected to flash chromatography (3:1 to 2:1 hexane:ethyl acetate) providing the desired protected monomer as a clear, colorless oil (6.2 mg, 5.3 $\mu$mol, 72%).

The protected monomer (0.2 mg, 5.3 $\mu$mol) was placed in a 1.5 mL polypropylene tube fitted with a spin vane. Acetonitrile (0.5 mL, 11 mM final concentration) was added and the solution stirred at room temperature as HF (55 $\mu$L, 48% aqueous solution; Fisher, 3.0N final concentration) was added. The solution was stirred 18 h at room temperature. The deprotected FK506 derivative was then partitioned between dichloromethane and saturated aqueous sodium bicarbonate in a 15 mL test tube. The tube was vortexed extensively to mix the phases and, after separation, the organic phase was removed with a pipet. The aqueous phase was back-extracted with dichloromethane (4×2 mL), and the combined organic phases were dried (MgSo$_4$), concentrated and subjected to flash chromatography (1:1 to 0:1 hexane:ethyl acetate) providing for the desired deprotected benzylcarbamate as a clear, colorless oil (3.9 mg, 4.1 $\mu$mol, 78%).

By replacing the benzylamine with a diamine such as xylylenediamine (12), hexamethylenediamine, octamethylenediamine, decamethylenediamine (13) or other diamines, dimeric compounds of the subject invention are prepared.

Example 12
Preparation of the Mixed Carbonate of FK506 (12)

A 10-EL flask was charged with 24, 32-bis [(tert-butyldimethylsilyl)oxy]-FK506 (339.5 mg., 0.329 mmol), 4-methylmorpholine N-oxide (193 mg, 1.64 mmol, 5 equiv), water (0.20 mL) and THF (8.0 mL, 41 mN final concentration). Osmium tetroxide (0.183 mL, 0.033 mmol, 0.1 equiv, 0.18M soln in water) was added via syringe. The clear, colorless solution was stirred at room temperature for 4.5 h. The reaction was diluted with 50% aqueous methonol (4.0 mL) and sodium periodate (700 mg, 3.29 mmol, 10 equiv) was added in one portion. The cloudy mixture was stirred 25 min at room temperature, diluted with ether (20 mL), and washed with saturated aqueous sodium bicarbonate solution (10 mL). The phases were separated and the aqueous layer was back-extracted with ether (2×10 mL). The combined organic layers were dried over MgSO$_4$ and solid sodium sulfite (50 mg). The organic phase was then filtered and concentrated and the resulting aldehyde was immediately dissolved in THF (8.0 mL) and cooled to −78° C. under an atmosphere of nitrogen, and treated with lithium tris [(3-ethyl-3-pentyl)oxy] aluminum hydride (2.35 mL, 0.329 mmol, 0.14M solution of THF, 1.0 equiv). The clear solution was allowed to stir for 60 min at −78° C. (monitored closely by TLC) then quenched at −78° C. by dilution with ether (5 mL) and addition of saturated aqueous ammonium chloride (0.3 mL). The mixture was allowed to warm to room temperature and solid sodium sulfate was added to dry the solution. The mixture was stirred 20 min, filtered, concentrated, and the resulting oil was immediately dissolved in acetonitrile (10 mL). To the solution of the resulting primary alcohol in CH$_3$CN was added 2,6-lutidine (0.380 mL, 3.3. mmol, 10 equiv) and N,N'-disuccinimidyl carbonate (420 mg, 1.65 mmol, 5 equiv). The heterogenous mixture was stirred at room temperature for 19 h, at which time the solution was diluted with ether (30 mL) and washed with saturated aqueous sodium bicarbonate (20 mL) The aqueous phase was back-extracted with ether (2×10 mL). The organic phases were combined and dried (MgSO$_4$)

concentrated, and subjected to flash chromatography (3:1 to 2:1 to 1:1 hexane/ethyl acetate). The desired mixed carbonate 12 was isolated as a clear, colorless oil (217 mg, 0.184 mmol, 56% overall for 4 steps)

Example 13
Preparation of 24, 24', 32, 32'-tetrakis [(tert-butyldimethylsilyl)oxy]-FK1012-A A dry, 1-mL conical glass vial was charged with the mixed carbonate (23.9 mg, 0.0203 mol) and acetonitrile (500 μL, 41 mM final concentration). Triethylamine (28 μL, 0.20 mmol, 10 equiv) was added followed by p-xylylenediamine (46 μL, 0.0101 mmol, 0.22M solution in DMF). The reaction stirred 18 h at room temperature, the solvent was removed with a stream of dry nitrogen, and the oil was directly subjected to flash chromatography (3:1 to 2:1 to 1:1 hexane/ethyl acetate) affording the desired protected dimer as a clear, colorless oil (11.9 mg, 5.3 μmol, 52%)

Example 14
Preparation of FK1012-A (p-xylylenediamine bridge) (13)

The protected dimer (11.0 mg, 4.9 μmol) was placed in a 1.5-mL polypropylene tube fitted with a spin vane. Acetonitrile (0.50 mL, 10 mM final concentration) was added, and the solution stirred at 20° C. as HF (55 μL, 48% aqueous solution; Fisher, 3.0N final concentration) was added. The solution was stirred 16 h at room temperature. The deprotected FK506 derivative was then partitioned between dichloromethane and saturated aqueous sodium bicarbonate in a 15-mL test tube. The tube was vortexed extensively to mix the phases and, after separation, the organic phase was removed with a pipet. The aqueous phase was back-extracted with dichloromethane (4×2 mL), and the combined organic phases were dried (MgSo$_4$), concentrated and subjected to flash chromatography (1:1:1 hexane/THF/ether to 1:1 THF/ether) providing FK1012-A as a clear, colorless oil (5.5 mg, 3.0 μmol, 63%)

Example 15
Preparation of 24, 24', 32, 32'-tetrakis[(tert-butyldimethylsilyl)oxy]-FK1012-B (diaminodecane bridge)

A dry, 1-mL conical glass vial was charged with the mixed carbonate (53.3 mg, 0.0453 mmol) and acetonitrile (2.0 mL, 11 m M final concentration). Triethylamine (16 μL, 0.11 mmol, 5 equiv) was added followed by diaminodecane (61 μL, 0.0226 mmol, 0.37M solution in DMF). The reaction stirred 12 h at room temperature, the solvent was removed with a stream of dry nitrogen, and the oil was directly subjected to flash chromatography (3:1 to 2:1 to 1:1 hexane/ethyl acetate) affording the desired protected dimer as a clear, colorless oil (18.0 mg, 7.8 μmol, 35%).

Example 16
Preparation of FK1012-B (diaminodecane-1,10 bridge) (14)

The protected dimer (18.0 mg, 7.8 μmol) was placed in a 1.5-mL polypropylene tube fitted with a stirring flea. Acetonitrile (0.45 mL, 16 mM final concentration) was added, and the solution stirred at room temperature as HF (55 μL, 48% aqueous solution; Fisher, 3.6N final concentration) was added. The solution was stirred 17 h at 23° C. The product FK1012-B was then partitioned between dichloromethane and saturated aqueous sodium bicarbonate in a 15-mL test tube. The tube was vortexed extensively to mix the phases and, after separation, the organic phase was removed with a pipet. The aqueous phase was back-extracted with dichloromethane (4×2 mL), and the combined organic phases were dried (MgSO$_4$), concentrated and subjected to flash chromatography (100% ethyl acetate to 20:1 ethyl acetate/methanol) affording FK1012-B as a clear, colorless oil (5.3 mg, 2.9 μmol, 37%).

Example 17
Preparation of 24, 24', 32, 32'-tetrakis[(tert-butyldimethylsilyl)oxy]-FK1012-C (bis-p-aminomethylbenzoyl diaminodecane bridge)

A dry 25-mL tear-shaped flask was charged with the diamine linker (15.1 mg, 0.0344 mmol) and 1.0 mL of DMF. In a separate flask, the mixed carbonate 12 and triethylamine (0.100 mL, 0.700 mmol, 20 equiv) were dissolved in 2.0 mL of dichloromethane then added slowly (4×0.50 mL) to the stirring solution or bis-p-aminomethylbenzoyl diaminodecane-1,10. The flask containing 12 was washed with dichloromethane (2×0.50 mL) to ensure complete transfer of 12. The reaction stirred 16 h at 23° C., the solvent was removed with a stream of dry nitrogen, and the oil was directly subjected to flash chromatography (1:1 to 1:2 hexane/ethyl acetate) to afford the desired protected dimer as a clear, colorless oil (29.6 mg, 11.5 μmol, 34%).

Example 18
Preparation of FK1012-C (15)

The protected dimer (29.6 mg, 11.5 μmol) (17) was placed in a 1.5-mL polypropylene tube Witted with a stirring flea. Acetonitrile (0.45 mL, 23 mM final concentration) was added, and the solution stirred at room temperature as HF (55 μL, 48% aqueous solution; Fisher, 3.6N final concentration) was added. The solution was stirred 17 h at room temperature. The desired symmetrical dimer was then partitioned between dichloromethane and saturated aqueous sodium bicarbonate in a 15-mL test tube. The tube was vortexed extensively to mix the phases and, after separation, the organic phase was removed with a pipet. The aqueous phase was back-extracted with dichloromethane (4×2 mL), and the combined organic phases were dried (MgSO$_4$), concentrated and subjected to flash chromatography (100% ethyl acetate to 15:1 ethyl acetate/methanol) affording FK1012-C as a clear, colorless oil (11.5 mg, 5.5 μmol, 47%).
Preparation of CsA Derivatives Example 19
MeBmt(OAc)-η-OH$^1$-CsA (2)

MeBmt(OAc)-η-OAc$^1$-CsA (1) (161 mg, 124 mmol) (see Eberle and Nuninger, *J. Org. Chem.* (1992) 57, 2689) was dissolved in Methanol (10 mL). KOH (196 mg) was dissolved in water (8 mL). 297 mL of the KOH solution (0.130 mmol, 1.05 eq.) was added to the solution of (1) in MeOH. This new solution was stirred at room temperature under an inert atmosphere for 4 hours at which time the reaction was quenched with acetic acid (2 mL). The reaction mixture was purified by reversed phase HPLC using a 5 cm×25 cm, 12μ, 100 A, C18 column at 70° C. eluting with 70% acetonitrile/ H$_2$O containing 0.1% (v/v) Trifluoroacetic acid to give 112 mg (72%) of the desired monoacetate (2).
MeBmt(OAc)-η-OCOIm$^1$-CsA (3)

MeBmt(OAc)-η-OH$^1$-CsA (2) (57 mg, 45.5 μmol) and carbonyldiimidazole (15 mg, 2 eq., 91 μmol.) were transferred into a 50 mL round bottom flask and dissolved in dry THF (6 mL). Diisopropylethylamine (32 μL, 4 eq., 182 μmol) was added and then the solvent was removed on a rotary evaporator at room temperature. The residue was purified by flash chromatography on silica gel using ethyl acetate as eluent to give 45 mg (73%) of the desired carbamate (3).
Tris-(2-aminoethyl)amine CsA Trimer Triacetate (6)

MeBmt(OAc)-η-OCOIm$^1$-CsA (3) (7.5 mg, 5.54 μmol, 3.1 eq.) was dissolved in THF (100 μL). Diisopropylethylamine (62 μL, 5 eq., 8.93 μmol of a solution containing 100 μL of amine in 4 mL THF) was added followed by tris(2-aminoethyl)amine (26 μL, 1.79 μmol, 1 eq. of a solution containing 101 mg of tris-amine in 10 mL THF). This solution was allowed to stir under $N_2$ atmosphere for 5 days. The reaction mix was evaporated and then purified by flash chromatography on silica gel using 0–5% methanol in chloroform to give 4.1 mg of desired product (6).

Example 20
Diaminodecane CsA Dimer (8)

Solid Na metal (200 mg, excess) was reacted with dry methanol (10 mL) at 0° C. Diaminodecane CsA Dimer Diacetate (5) (4.0 mg) was dissolved in MeOH (5 mL). 2.5 mL of the NaOMe solution was added to the solution of (5). After 2.5 hours of stirring at room temperature under an inert atmosphere, the solution was quenched with acetic acid (2 mL) and the product was purified ha reversed phase HPLC using a 5 mm×25 mm, 12μ, 100 A, C18 column at 70° C. eluting with 70–95% acetonitrile/$H_2O$ over 20 minutes containing 0.1% (v/v) Trifluoroacetic acid to give 2.5 mg (60%) of the desired diol.

The diaminodecane CsA Dimer Diacetate (5) was prepared by replacing the tris(2-aminoethyl)amine with 0.45 eq. of 1,10-diaminodecane.

Example 21
p-Xylylenediamine CsA Dimer (4)

The p-xylene diamine CsA Dimer (4) Was prepared by replacing the tris(2-aminoethyl)amino with 0.45 eq. of p-xylylene diamine.

Following procedures described in the literature other derivatives of cyclophilin are prepared by linking at a site other than the 1(MeBmt 1) site.

Position 8 D-isomer analogues are produced by feeding the producing organism with the D-amino analogue to obtain incorporation specifically at that site. See Patchett, et al., *J. Antibiotics* (1992) 45, 943 (β-MeSO)D-Ala$^8$-CsA); Traber, et al., ibid. (1989) 42, 591). The position 3 analogues are prepared by poly-lithiation/alkylation of CsA, specifically at the α-carbon of Sac3. See Wenger, *Transplant Proceeding* (1986) 18, 213, supp. 5 (for cyclophilin binding and activity profiles, particularly D-MePhe$^3$-CsA); Seebach, U.S. Pat. No. 4,703,033, issued Oct. 27, 1987 (for preparation of derivatives).

Instead of cyclosporin A, following the above-described procedures, other naturally-occurring variants of CsA may be multimerized for use in the subject invention.

It is evident from the above results, that the subject method and compositions provide for great versatility in the production of cells for a wide variety of purposes. By employing the subject constructs, one can use cells for therapeutic purposes, where the cells may remain inactive until needed, and then be activated by administration of a safe drug. Because cells can have a wide variety of lifetimes in a host, there is the opportunity to treat both chronic and acute indications so as to provide short- or long-term protection. In addition, one can provide for cells which will be directed to a particular site, such as an anatomic site or a functional site, where therapeutic effect may be provided.

Cells can be provided which will result in secretion of a wide variety of proteins, which may serve to correct a deficit or inhibit an undesired result, such as activation of cytolytic cells, to inactivate a destructive agent, to kill a restricted cell population, or the like. By having the cells present in the host over a defined period of time, the cells may be readily activated by taking the drug at a dose which can result in a rapid response of the cells in the host. Cells can be provided where the expressed chimeric receptor is intracellular, avoiding any immune response due to a foreign protein on the cell surface. Furthermore, the intracellular chimeric receptor protein provides for efficient signal transduction upon ligand binding, apparently more efficiently than the receptor binding at an extracellular receptor domain.

By using relatively simple molecules which bind to chimeric membrane bound receptors, resulting in the expression of products of interest or inhibiting the expression of products, one can provide for cellular therapeutic treatment. The compounds which may be administered are safe, can be administered in a variety of ways, and can ensure a very specific response, so as not to upset homeostasis.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound comprising two or more multimerized ligands each independently selected from the group consisting of FK506, FK520 and cyclosporin, or macrocyclic derivatives thereof.

2. A compound comprising two or more multimerized ligands each independently selected from the group consisting of FK506, FK520, and macrocyclic derivatives thereof, which compound cross-links two or more FKBP proteins.

3. A compound according to claim 2, wherein said ligands are linked though any of annular carbon atoms at positions 17 to 24 or 32 or through ring substituents.

4. The compound of claims 1, wherein at least one of the ligands is a macrolide derivative of FK506, FK520 or cyclosporin A.

5. The compound of claim 2, wherein at least one of the ligands is a macrolide derivative of FK506 or FK520.

6. A compound according to claim 1 or 2, wherein said ligands are linked through amide groups.

7. A compound comprising two or more multimerized ligands independently selected from cyclosporin A or macrocyclic derivatives thereof, which compound cross-links two or more cyclophilin proteins.

8. A compound according to claim 7, wherein said ligands are linked through amide groups.

9. A compound according to claim 7, wherein said ligands are linked through the MeBmt1 sidechain.

10. The compound of claim 7, wherein at least one of the ligands is a macrolide derivative of cyclosporin A.

11. The compound of claim 2, wherein one or more of said ligands of the compound is a macrocycle derivative of a parent compound FK506 or FK520, which derivative has a reduced binding affinity for a native FKBP relative to the parent compound.

12. The compound of claim 7, wherein one or more of said ligands of the compound is a macrocycle derivative of a parent compound cyclosporin, which derivative has a reduced binding affinity for a native cyclophilin relative to the patent compound.

13. The compound of any of claims 11 or 12, wherein the derivative of the parent compound has a reduced immunosuppressive activity relative to the parent compound.

14. The compound of any of claims 1, 2, 7, 11 or 12, wherein the compound is membrane permeable.

15. The compound of any of claims 1, 2, 7, 11 or 12, wherein the compound has a molecular weight less than 5 Kd.

16. A compound according to claim 1, 2 or 7 consisting of 2 to 3 ligands covalently joined by a linker group.

17. A compound according to any of claims 1, 2, or 7, wherein the linker is selected from the group consisting of alkylene, azalkylene, N-alkylene azalkylene, arylene, aradialkylene, and bis-carbozamidoalkylene.

18. A compound, having a molecular weight of less than 5 Kd and comprising from 2 to 3 ligands, each ligand of which independently comprises a macrocycle or portion thereof which binds to FKBP or cyclophilin, said units covalently joined together through a common linking group does not include an ester group in the backbone of the linker.

19. A compound, having a molecular weight less than 5 kd and comprising two or more ligands covalently joined through one or more linker groups, each ligand independently comprising a macrocycle or portion thereof which binds an FKBP or cyclophilin protein, wherein said compound has a reduced immunosuppressive effect in a Tag Jurkat cell mitogen activation assay.

20. The compound of claim 19, wherein said compound has a reduced immunosuppressive effect in a Tag Jurkat cell mitogen activation assay.

21. The compound of claim 19, consisting of 2 to 3 ligands covalently joined by the linker group.

22. The compound of claim 19, wherein the compound is membrane permeable.

23. The compound claim 18 or 19, wherein each ligand independently comprises a macrolide or portion thereof which binds an FKBP or cyclophilin protein.

24. The compound of claim 19, wherein the linker group does not include an ester or amide susceptible to cleavage under physiological conditions.

25. The compound of claim 19 or 24, wherein the linker group is resistant to cleavage by proteases.

26. The compound of any of claims 19 or 24, wherein the linker group is selected from the group consisting of alkylene, azaalkylene, N-alkylene azalkylene, arylene, ardialkylene group, and bis-carbozamidoalkylene.

27. The compound of any of claims 1, 2, 7, 18 or 19, wherein the compound is at least 100 fold less immunosuppressive than FK506, cyclosporin A or rapamycin.

28. A compound, having a molecular weight less than 5 kd and comprising two or more ligands covalently joined through one or more linker group, each ligand independently comprising a macrocycle or portion thereof which binds an FKBP or cyclophilin protein or mutagenized derivative thereof, wherein the compound is at least 100 fold less immunosuppressive than FK506, cyclosporin A or rapamycin.

29. The compound of claim 28, wherein the linker group is resistant to cleavage by proteases.

30. The compound of claim 28, consisting of 2 to 3 ligands covalently joined by the linker group.

31. The compound of claim 28, wherein the compound is membrane permeable.

32. The compound of claim 28, wherein the compound is at least 1000 fold less immunosuppressive than FK 506, cyclosporin A or rapamycin in a Tag Jurkat cell mitogen activation assay.

33. The compound of claim 28, wherein the linker group does not include an ester or amide susceptible to cleavage under physiological conditions.

34. The compound of any of claims 28 or 33, wherein the linker group is selected from the group consisting of alkylene, azaalkylene, N-alkylene azalkylene, arylene, ardialkylene group, and bis-carbozamidoalkylene.

35. The compound of claim 27, wherein the compound is at least 1000 fold less immunosuppressive than FK 506, Cyclosporin A or rapamycin in a Tag Jurkat cell mitogen activation assay.

* * * * *

SEQUENCE LISTING ( 1 ) GENERAL INFORMATION:

( i i i ) NUMBER OF SEQUENCES: 66

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Met  Gly  Ser  Ser  Lys  Ser  Lys  Pro  Lys  Asp  Pro  Ser  Gln  Arg
 1              5                        10
```

-continued (2) INFORMATION FOR SEQ ID NO:2:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

GTTAAGTTAA C                                      11

(2) INFORMATION FOR SEQ ID NO:3:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TGACTCAGCG C                                      11

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Sac II restriction site."

(ix) FEATURE:
        (A) NAME/KEY: misc_signal
        (B) LOCATION: 12..16
        (D) OTHER INFORMATION: /note= "Kozak sequence."

(ix) FEATURE:
        (A) NAME/KEY: CDS
        (B) LOCATION: 17..31

(ix) FEATURE:
        (A) NAME/KEY: misc_feature
        (B) LOCATION: 17..33
        (D) OTHER INFORMATION: /note= "Region of homology with
            target sequence."

(xi) SEQUENCE DESCRIPTION: SEQ ID NO:4:

CGACACCGCG GCCACC ATG GCC ACA ATT GGA GC              33
                         Met Ala Thr Ile Gly
                          1            5

(2) INFORMATION FOR SEQ ID NO:5:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:5:

Met Ala Thr Ile Gly
1            5

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 6..11
        ( D ) OTHER INFORMATION: /note= "Xho I restriction site."

( i x ) FEATURE:
        ( A ) NAME/KEY: misc_feature
        ( B ) LOCATION: 12..27
        ( D ) OTHER INFORMATION: /note= "Region of homology with target sequence."

( x i ) SEQUENCE DESCRIPTION: SEQ ID NO:6:

CGACACTCGA GAGCCCATGA CTTCTGG     27

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..4
        ( D ) OTHER INFORMATION: /note= "Translation product of complement of SEQ ID NO:6, bases 9 to 20."

( x i ) SEQUENCE DESCRIPTION: SEQ ID NO:7:

Ser Trp Ala Leu
1

( 2 ) INFORMATION FOR SEQ ID NO:8:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 6..11
        ( D ) OTHER INFORMATION: /note= "Xho I restriction site."

( i x ) FEATURE:
        ( A ) NAME/KEY: misc_feature
        ( B ) LOCATION: 12..41
        ( D ) OTHER INFORMATION: /note= "Region of homology with target sequence."

( i x ) FEATURE:
        ( A ) NAME/KEY: CDS
        ( B ) LOCATION: 9..41

( i x ) FEATURE:
        ( A ) NAME/KEY: misc_feature
        ( B ) LOCATION: 28
        ( D ) OTHER INFORMATION: /note= "A to G."

-continued ( x i ) SEQUENCE DESCRIPTION: SEQ ID NO:8:

```
CGACACTC GAG CTC TGC TAC TTG CTA GGT GGA ATC CTC TTC              41
         Glu Leu Cys Tyr Leu Leu Gly Gly Ile Leu Phe
         1               5                   10
```

( 2 ) INFORMATION FOR SEQ ID NO:9:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Glu Leu Cys Tyr Leu Leu Gly Gly Ile Leu Phe
1               5                   10
```

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 3..8
        ( D ) OTHER INFORMATION: /note= "Eco RI restriction site."

( i x ) FEATURE:
        ( A ) NAME/KEY: misc_feature
        ( B ) LOCATION: 9..24
        ( D ) OTHER INFORMATION: /note= "Region of homology with
            target sequence."

( i x ) FEATURE:
        ( A ) NAME/KEY: misc_feature
        ( B ) LOCATION: 24
        ( D ) OTHER INFORMATION: /note= "G to C."

( i x ) FEATURE:
        ( A ) NAME/KEY: misc_signal
        ( B ) LOCATION: complement (9..11)
        ( D ) OTHER INFORMATION: /note= "Translational stop encoded
            in complementary strand."

( x i ) SEQUENCE DESCRIPTION: SEQ ID NO:10:

```
GCGAATTCTT AGCGAGGGGC CAGC                                        24
```

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..4
        ( D ) OTHER INFORMATION: /note= "Translational product of
            complement to SEQ ID NO:10, bases 12 to 23."

( x i ) SEQUENCE DESCRIPTION: SEQ ID NO:11:

```
Leu Ala Pro Arg
1
```

( 2 ) INFORMATION FOR SEQ ID NO:12:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 3..8
        ( D ) OTHER INFORMATION: /note= "Eco RI restriction."

( i x ) FEATURE:
        ( A ) NAME/KEY: misc_feature
        ( B ) LOCATION: 12..17
        ( D ) OTHER INFORMATION: /note= "Sal I restriction site."

( i x ) FEATURE:
        ( A ) NAME/KEY: misc_signal
        ( B ) LOCATION: complement (9..11)
        ( D ) OTHER INFORMATION: /note= "Translational stop signal
            encoded on complementary strand."

( i x ) FEATURE:
        ( A ) NAME/KEY: misc_feature
        ( B ) LOCATION: 18..33
        ( D ) OTHER INFORMATION: /note= "Region of homology with
            target sequence."

( x i ) SEQUENCE DESCRIPTION: SEQ ID NO:12:

```
GCGAATTCTT   AGTCGACGCG   AGGGGCCAGG   GTC                                      33
```

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..4
        ( D ) OTHER INFORMATION: /note= "Translational product of
            complement to SEQ ID NO:12, bases 18 to 29."

( x i ) SEQUENCE DESCRIPTION: SEQ ID NO:13:

```
Leu  Ala  Pro  Arg
 1
```

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 4..9
        ( D ) OTHER INFORMATION: /note= "Xho I restriction site."

( i x ) FEATURE:
        ( A ) NAME/KEY: misc_feature
        ( B ) LOCATION: 13
        ( D ) OTHER INFORMATION: /note= "T to G."

( i x ) FEATURE:
    ( A ) NAME/KEY: misc_feature
    ( B ) LOCATION: 4..25
    ( D ) OTHER INFORMATION: /note= "Region of homology with
        target sequence."

( i x ) FEATURE:
    ( A ) NAME/KEY: CDS
    ( B ) LOCATION: 10..24

( x i ) SEQUENCE DESCRIPTION: SEQ ID NO:14:

```
GGGCTCGAG CTC GGC TAC TTG CTA G                                          25
          Leu Gly Tyr Leu Leu
           1               5
```

( 2 ) INFORMATION FOR SEQ ID NO:15:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: protein ( x i ) SEQUENCE DESCRIPTION: SEQ ID NO:15:

```
Leu Gly Tyr Leu Leu
 1               5
```

( 2 ) INFORMATION FOR SEQ ID NO:16:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 6..11
    ( D ) OTHER INFORMATION: /note= "Xho I restriction site."

( i x ) FEATURE:
    ( A ) NAME/KEY: misc_feature
    ( B ) LOCATION: 12..26
    ( D ) OTHER INFORMATION: /note= "Region of homology with
        target sequence."

( x i ) SEQUENCE DESCRIPTION: SEQ ID NO:16:

```
CGACACTCGA GGTGACGGAC AAGGTC                                             26
```

( 2 ) INFORMATION FOR SEQ ID NO:17:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 6..11
    ( D ) OTHER INFORMATION: /note= "Sal I restriction site."

( i x ) FEATURE:
    ( A ) NAME/KEY: misc_feature
    ( B ) LOCATION: 12..26
    ( D ) OTHER INFORMATION: /note= "Region of homology with
        target sequence."

( x i ) SEQUENCE DESCRIPTION: SEQ ID NO:17:

```
CGACAGTCGA  CCCAATCAGG  GACCTC                                                              26
```

( 2 ) INFORMATION FOR SEQ ID NO:18:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..5
        ( D ) OTHER INFORMATION: /note= "Xho I restriction site."

( i x ) FEATURE:
        ( A ) NAME/KEY: misc_feature
        ( B ) LOCATION: 10..15
        ( D ) OTHER INFORMATION: /note= "Bsi WI restriction site."

( i x ) FEATURE:
        ( A ) NAME/KEY: CDS
        ( B ) LOCATION: 6..32

( x i ) SEQUENCE DESCRIPTION: SEQ ID NO:18:

```
TCGAG TAT CCG TAC GAC GTA CCA GAC TAC GCA G                                                 33
      Tyr Pro Tyr Asp Val Pro Asp Tyr Ala
       1               5
```

( 2 ) INFORMATION FOR SEQ ID NO:19:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Tyr Pro Tyr Asp Val Pro Asp Tyr Ala
 1               5
```

( 2 ) INFORMATION FOR SEQ ID NO:20:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..5
        ( D ) OTHER INFORMATION: /note= "Sal I restriction site."

( x i ) SEQUENCE DESCRIPTION: SEQ ID NO:20:

```
TCGACTGCGT  AGTCTGGTAC  GTCGTACGGA  TAC                                                     33
```

( 2 ) INFORMATION FOR SEQ ID NO:21:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..5
        ( D ) OTHER INFORMATION: /note= "Sal I restriction site."

( x i ) SEQUENCE DESCRIPTION: SEQ ID NO:21:

TCGACTATCC GTACGACGTA CCAGACTACG CAC         33

( 2 ) INFORMATION FOR SEQ ID NO:22:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..5
        ( D ) OTHER INFORMATION: /note= "Xho I restriction site."

( x i ) SEQUENCE DESCRIPTION: SEQ ID NO:22:

TCGAGTGCGT AGTCTGGTAC GTCGTACGGA TAG         33

( 2 ) INFORMATION FOR SEQ ID NO:23:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 6..11
        ( D ) OTHER INFORMATION: /note= "Sac II restriction site."

( i x ) FEATURE:
        ( A ) NAME/KEY: misc_signal
        ( B ) LOCATION: 12..16
        ( D ) OTHER INFORMATION: /note= "Kozak sequence."

( i x ) FEATURE:
        ( A ) NAME/KEY: misc_signal
        ( B ) LOCATION: 17..58
        ( D ) OTHER INFORMATION: /note= "Myristoylation signal."

( i x ) FEATURE:
        ( A ) NAME/KEY: misc_feature
        ( B ) LOCATION: 59..64
        ( D ) OTHER INFORMATION: /note= "Xho I restriction site."

( i x ) FEATURE:
        ( A ) NAME/KEY: misc_feature
        ( B ) LOCATION: 65..80
        ( D ) OTHER INFORMATION: /note= "Zeta homology."

( i x ) FEATURE:
        ( A ) NAME/KEY: CDS
        ( B ) LOCATION: 17..79

( x i ) SEQUENCE DESCRIPTION: SEQ ID NO:23:

```
CGACACCGCG GCCACC ATG GGG AGT AGC AAG AGC AAG CCT AAG GAC CCC        49
               Met Gly Ser Ser Lys Ser Lys Pro Lys Asp Pro
                1               5                  10

AGC CAG CGC CTC GAG AGG AGT GCA GAG ACT G                            80
Ser Gln Arg Leu Glu Arg Ser Ala Glu Thr
         15                  20
```

( 2 ) INFORMATION FOR SEQ ID NO:24:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Met Gly Ser Ser Lys Ser Lys Pro Lys Asp Pro Ser Gln Arg Leu Glu
 1               5                  10                  15
Arg Ser Ala Glu Thr
             20
```

( 2 ) INFORMATION FOR SEQ ID NO:25:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 12..26

( i x ) FEATURE:
        ( A ) NAME/KEY: misc_feature
        ( B ) LOCATION: 6..11
        ( D ) OTHER INFORMATION: /note= "Xho I restriction site."

( i x ) FEATURE:
        ( A ) NAME/KEY: misc_feature
        ( B ) LOCATION: 12..27
        ( D ) OTHER INFORMATION: /note= "Region of homology with
            target sequence."

( x i ) SEQUENCE DESCRIPTION: SEQ ID NO:25:

```
CGACACTCGA G GAG CTC TGT GAC GAT G                                27
             Glu Leu Cys Asp Asp
              1               5
```

( 2 ) INFORMATION FOR SEQ ID NO:26:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Glu Leu Cys Asp Asp
 1               5
```

( 2 ) INFORMATION FOR SEQ ID NO:27:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 6..11
        ( D ) OTHER INFORMATION: /note= "Xho I restriction site."

( i x ) FEATURE:
    ( A ) NAME/KEY: misc_feature
    ( B ) LOCATION: 12..41
    ( D ) OTHER INFORMATION: /note= "Region of homology with
        target sequence."

( i x ) FEATURE:
    ( A ) NAME/KEY: misc_feature
    ( B ) LOCATION: 27..29
    ( D ) OTHER INFORMATION: /note= "GAT to AAG."

( i x ) FEATURE:
    ( A ) NAME/KEY: CDS
    ( B ) LOCATION: 9..41

( x i ) SEQUENCE DESCRIPTION: SEQ ID NO:27:

```
CGACACTC GAG CTC TGC TAC TTG CTA AAG GGA ATC CTC TTC         41
         Glu Leu Cys Tyr Leu Leu Lys Gly Ile Leu Phe
         1               5                   10
```

( 2 ) INFORMATION FOR SEQ ID NO:28:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Glu Leu Cys Tyr Leu Leu Lys Gly Ile Leu Phe
1               5                   10
```

( 2 ) INFORMATION FOR SEQ ID NO:29:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 6..11
        ( D ) OTHER INFORMATION: /note= "Xho I restriction site."

( i x ) FEATURE:
        ( A ) NAME/KEY: CDS
        ( B ) LOCATION: 9..44

( i x ) FEATURE:
        ( A ) NAME/KEY: misc_feature
        ( B ) LOCATION: 27..44
        ( D ) OTHER INFORMATION: /note= "Region of homology with
            target sequence."

( x i ) SEQUENCE DESCRIPTION: SEQ ID NO:29:

```
CGACACTC GAG CTG CTG GAT CCG AAG CTC TGC TAC TTG CTA AAG         44
         Glu Leu Leu Asp Pro Lys Leu Cys Tyr Leu Leu Lys
         1               5                   10
```

( 2 ) INFORMATION FOR SEQ ID NO:30:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

Glu Leu Leu Asp Pro Lys Leu Cys Tyr Leu Leu Lys
 1               5                   1 0

( 2 ) INFORMATION FOR SEQ ID NO:31:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 6..11
        ( D ) OTHER INFORMATION: /note= "Xho I restriction site."

( i x ) FEATURE:
        ( A ) NAME/KEY: misc_feature
        ( B ) LOCATION: 12..31
        ( D ) OTHER INFORMATION: /note= "Region of homology with
            target sequence."

( i x ) FEATURE:
        ( A ) NAME/KEY: CDS
        ( B ) LOCATION: 9..31

( x i ) SEQUENCE DESCRIPTION: SEQ ID NO:31:

CGACACTC GAG ACA ACA GAG TAC CAG GTA GC                      31
        Glu Thr Thr Glu Tyr Gln Val Ala
         1               5

( 2 ) INFORMATION FOR SEQ ID NO:32:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

Glu Thr Thr Glu Tyr Gln Val Ala
 1               5

( 2 ) INFORMATION FOR SEQ ID NO:33:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 6..11
        ( D ) OTHER INFORMATION: /note= "Xho I restriction site."

( i x ) FEATURE:
        ( A ) NAME/KEY: misc_feature
        ( B ) LOCATION: 12..28
        ( D ) OTHER INFORMATION: /note= "Region of homology with
            target sequence."

( i x ) FEATURE:
        ( A ) NAME/KEY: CDS
        ( B ) LOCATION: 9..28

( x i ) SEQUENCE DESCRIPTION: SEQ ID NO:33:

CGACACTC GAG GGC GTG CAG GTG GAG AC                          28
        Glu Gly Val Gln Val Glu Thr (2) INFORMATION FOR SEQ ID NO:34:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:34:

Glu Gly Val Gln Val Glu Thr
1               5

(2) INFORMATION FOR SEQ ID NO:35:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Sal I restriction site."

(ix) FEATURE:
        (A) NAME/KEY: misc_feature
        (B) LOCATION: 12..27
        (D) OTHER INFORMATION: /note= "Region of homology with
            target sequence."

(ix) FEATURE:
        (A) NAME/KEY: CDS
        (B) LOCATION: complement (9..26)

(xi) SEQUENCE DESCRIPTION: SEQ ID NO:35:

CGACAGTCGA CTTCCAGTTT TAGAAGC    27

(2) INFORMATION FOR SEQ ID NO:36:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:36:

Leu Leu Lys Leu Glu Val
1               5

(2) INFORMATION FOR SEQ ID NO:37:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 7..12
        (D) OTHER INFORMATION: /note= "Xho I restriction site."

(ix) FEATURE:
        (A) NAME/KEY: CDS ( B ) LOCATION: 10..27

( i x ) FEATURE:
              ( A ) NAME/KEY: misc_feature
              ( B ) LOCATION: 13..27
              ( D ) OTHER INFORMATION: /note= "Region of homology with
                    target sequence."

( x i ) SEQUENCE DESCRIPTION: SEQ ID NO:37:

TCGACACTC GAG ACG GGG GCC GAG GGC                                                27
          Glu Thr Gly Ala Glu Gly
          1               5

( 2 ) INFORMATION FOR SEQ ID NO:38:

( i ) SEQUENCE CHARACTERISTICS:
              ( A ) LENGTH: 6 amino acids
              ( B ) TYPE: amino acid
              ( D ) TOPOLOGY: linear ( i i ) MOLECULE TYPE: protein ( x i ) SEQUENCE DESCRIPTION: SEQ ID NO:38:

Glu Thr Gly Ala Glu Gly
1               5

( 2 ) INFORMATION FOR SEQ ID NO:39:

( i ) SEQUENCE CHARACTERISTICS:
              ( A ) LENGTH: 28 base pairs
              ( B ) TYPE: nucleic acid
              ( C ) STRANDEDNESS: single
              ( D ) TOPOLOGY: linear ( i i ) MOLECULE TYPE: cDNA ( i x ) FEATURE:
              ( A ) NAME/KEY: misc_feature
              ( B ) LOCATION: 7..12
              ( D ) OTHER INFORMATION: /note= "Sal I restriction site."

( i x ) FEATURE:
              ( A ) NAME/KEY: CDS
              ( B ) LOCATION: complement (10..18)

( i x ) FEATURE:
              ( A ) NAME/KEY: misc_feature
              ( B ) LOCATION: 13..28
              ( D ) OTHER INFORMATION: /note= "Region of homology with
                    target sequence."

( x i ) SEQUENCE DESCRIPTION: SEQ ID NO:39:

CCGACAGTCG ACCTCTATTT TGAGCAGC                                                   28

( 2 ) INFORMATION FOR SEQ ID NO:40:

( i ) SEQUENCE CHARACTERISTICS:
              ( A ) LENGTH: 3 amino acids
              ( B ) TYPE: amino acid
              ( D ) TOPOLOGY: linear ( i i ) MOLECULE TYPE: protein ( x i ) SEQUENCE DESCRIPTION: SEQ ID NO:40:

Ile Glu Val
1

( 2 ) INFORMATION FOR SEQ ID NO:41:

( i ) SEQUENCE CHARACTERISTICS:
              ( A ) LENGTH: 38 base pairs
              ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:41:

CGACACCGCG GCCACCATGA AGCTACTGTC TTCTATCG    38

( 2 ) INFORMATION FOR SEQ ID NO:42:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:42:

CGACAGTCGA CCGATACAGT CAACTGTC    28

( 2 ) INFORMATION FOR SEQ ID NO:43:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: misc_feature
( B ) LOCATION: 6..11
( D ) OTHER INFORMATION: /note= "Sac II restriction site."

( i x ) FEATURE:
( A ) NAME/KEY: misc_signal
( B ) LOCATION: 12..16
( D ) OTHER INFORMATION: /note= "Kozak sequence."

( i x ) FEATURE:
( A ) NAME/KEY: CDS
( B ) LOCATION: 17..37

( i x ) FEATURE:
( A ) NAME/KEY: misc_feature
( B ) LOCATION: 17..38
( D ) OTHER INFORMATION: /note= "Gal4 (1-147) coding
region."

( x i ) SEQUENCE DESCRIPTION: SEQ ID NO:43:

CGACACCGCG GCCACC ATG AAG CTA CTG TCT TCT ATC G    38
                  Met Lys Leu Leu Ser Ser Ile
                   1               5

( 2 ) INFORMATION FOR SEQ ID NO:44:

( i ) SEQUENCE CHARACTERISTICS:
( A ) LENGTH: 7 amino acids
( B ) TYPE: amino acid
( D ) TOPOLOGY: linear ( i i ) MOLECULE TYPE: protein ( x i ) SEQUENCE DESCRIPTION: SEQ ID NO:44:

Met Lys Leu Leu Ser Ser Ile
 1               5

( 2 ) INFORMATION FOR SEQ ID NO:45:

( i ) SEQUENCE CHARACTERISTICS:

(A) LENGTH: 28 base pairs
                (B) TYPE: nucleic acid
                (C) STRANDEDNESS: double
                (D) TOPOLOGY: linear (ii) MOLECULE TYPE: cDNA (ix) FEATURE:
                (A) NAME/KEY: misc_feature
                (B) LOCATION: 1..17
                (D) OTHER INFORMATION: /note= "Region encoding for
                    C-terminal end of Gal4 (1-147)."

(ix) FEATURE:
                (A) NAME/KEY: CDS
                (B) LOCATION: 3..17

(ix) FEATURE:
                (A) NAME/KEY: misc_feature
                (B) LOCATION: 18..23
                (D) OTHER INFORMATION: /note= "Sal I restriction site."

(xi) SEQUENCE DESCRIPTION: SEQ ID NO:45:

```
GA CAG TTG ACT GTA TCG GTCGACTGTC G                          28
   Arg Gln Leu Thr Val Ser
    1               5
```

(2) INFORMATION FOR SEQ ID NO:46:

(i) SEQUENCE CHARACTERISTICS:
                (A) LENGTH: 6 amino acids
                (B) TYPE: amino acid
                (D) TOPOLOGY: linear (ii) MOLECULE TYPE: protein (xi) SEQUENCE DESCRIPTION: SEQ ID NO:46:

```
Arg Gln Leu Thr Val Ser
 1               5
```

(2) INFORMATION FOR SEQ ID NO:47:

(i) SEQUENCE CHARACTERISTICS:
                (A) LENGTH: 34 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:47:

```
CGACACCGCG  GCCACCATGG  TTTCTAAGCT  GAGC                     34
```

(2) INFORMATION FOR SEQ ID NO:48:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:48:

```
CGACAGTCGA  CCAACTTGTG  CCGGAAGG                             28
```

(2) INFORMATION FOR SEQ ID NO:49:

(i) SEQUENCE CHARACTERISTICS:
                (A) LENGTH: 34 base pairs
                (B) TYPE: nucleic acid
                (C) STRANDEDNESS: single (D) TOPOLOGY: linear (ii) MOLECULE TYPE: cDNA (ix) FEATURE:
    (A) NAME/KEY: misc_feature
    (B) LOCATION: 6..11
    (D) OTHER INFORMATION: /note= "Sac II restriction site."

(ix) FEATURE:
    (A) NAME/KEY: misc_signal
    (B) LOCATION: 12..16
    (D) OTHER INFORMATION: /note= "Kozak sequence."

(ix) FEATURE:
    (A) NAME/KEY: CDS
    (B) LOCATION: 17..34

(ix) FEATURE:
    (A) NAME/KEY: misc_feature
    (B) LOCATION: 17..34
    (D) OTHER INFORMATION: /note= "Region encoding N-terminal end of HNF1 (1-281)."

(xi) SEQUENCE DESCRIPTION: SEQ ID NO:49:

```
CGACACCGCG GCCACC ATG GTT TCT AAG CTG AGC                                34
               Met Val Ser Lys Leu Ser
                1              5
```

(2) INFORMATION FOR SEQ ID NO:50:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:50:

```
Met Val Ser Lys Leu Ser
 1              5
```

(2) INFORMATION FOR SEQ ID NO:51:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: misc_feature
        (B) LOCATION: 1..20
        (D) OTHER INFORMATION: /note= "Region encoding for C-terminal end of HNF1 (1-282)."

(ix) FEATURE:
        (A) NAME/KEY: CDS
        (B) LOCATION: 3..17

(xi) SEQUENCE DESCRIPTION: SEQ ID NO:51:

```
CC TTC CGG CAC AAG TTG GTCGACTGTC G                                      28
Ala Phe Arg His Lys Leu
 1               5
```

(2) INFORMATION FOR SEQ ID NO:52:

(i) SEQUENCE CHARACTERISTICS:
        (A) LENGTH: 6 amino acids
        (B) TYPE: amino acid
        (D) TOPOLOGY: linear (i i) MOLECULE TYPE: protein (x i) SEQUENCE DESCRIPTION: SEQ ID NO:52:

Ala Phe Arg His Lys Leu
 1               5

(2) INFORMATION FOR SEQ ID NO:53:

(i) SEQUENCE CHARACTERISTICS:
        (A) LENGTH: 11 base pairs
        (B) TYPE: nucleic acid
        (C) STRANDEDNESS: both
        (D) TOPOLOGY: linear (i i) MOLECULE TYPE: cDNA (i x) FEATURE:
        (A) NAME/KEY: misc_signal
        (B) LOCATION: 3..7
        (D) OTHER INFORMATION: /note= "Kozak sequence."

(i x) FEATURE:
        (A) NAME/KEY: misc_feature
        (B) LOCATION: 1..11
        (D) OTHER INFORMATION: /note= "Complementary to bases 5 to
            15 of SEQ ID NO:54."

(x i) SEQUENCE DESCRIPTION: SEQ ID NO:53:

GGCCACCATG C                                      11

(2) INFORMATION FOR SEQ ID NO:54:

(i) SEQUENCE CHARACTERISTICS:
        (A) LENGTH: 3 amino acids
        (B) TYPE: amino acid
        (C) STRANDEDNESS: single
        (D) TOPOLOGY: linear (i x) FEATURE:
        (A) NAME/KEY: Peptide
        (B) LOCATION: 1..3
        (D) OTHER INFORMATION: /note= "Translation product of SEQ
            ID NO:53 and SEQ ID NO:55. Translational start
            site at base 8 of SEQ ID NO:53."

(x i) SEQUENCE DESCRIPTION: SEQ ID NO:54:

Met Leu Glu
 1

(2) INFORMATION FOR SEQ ID NO:55:

(i) SEQUENCE CHARACTERISTICS:
        (A) LENGTH: 17 base pairs
        (B) TYPE: nucleic acid
        (C) STRANDEDNESS: both
        (D) TOPOLOGY: linear (i i) MOLECULE TYPE: cDNA (i x) FEATURE:
        (A) NAME/KEY: misc_feature
        (B) LOCATION: 14..17
        (D) OTHER INFORMATION: /note= "Sac II restriction site
            overhang."

(i x) FEATURE:
        (A) NAME/KEY: misc_feature
        (B) LOCATION: 1..5
        (D) OTHER INFORMATION: /note= "Xho I restriction site
            overhang."

(i x) FEATURE:
        (A) NAME/KEY: misc_feature
        (B) LOCATION: 5..15

( D ) OTHER INFORMATION: /note= "Complementary to bases 1 to
  11 of SEQ ID NO:53."

( x i ) SEQUENCE DESCRIPTION: SEQ ID NO:55:

TCGAGCATGG TGGCCGC                                                                                          17

( 2 ) INFORMATION FOR SEQ ID NO:56:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:56:

TCGACCCTAA GAMGAAGAGA AAGGTAC                                                                               27

( 2 ) INFORMATION FOR SEQ ID NO:57:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:57:

TCGAGTACCT TTCTCTTCKT CTTAGGG                                                                               27

( 2 ) INFORMATION FOR SEQ ID NO:58:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: misc_feature
        ( B ) LOCATION: 1..5
        ( D ) OTHER INFORMATION: /note= "Sal I restriction site
            overhang."

( i x ) FEATURE:
        ( A ) NAME/KEY: misc_feature
        ( B ) LOCATION: 5..27
        ( D ) OTHER INFORMATION: /note= "Complementary to SEQ ID
            NO:60, bases 5 to 27."

( x i ) SEQUENCE DESCRIPTION: SEQ ID NO:58:

TCGACCCTAA GAAGAAGAGA AAGGTAC                                                                               27

( 2 ) INFORMATION FOR SEQ ID NO:59:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i x ) FEATURE:
        ( A ) NAME/KEY: Peptide
        ( B ) LOCATION: 1..11
        ( D ) OTHER INFORMATION: /note= "Translation product of SEQ
            ID NOS:58 and 60."

( x i ) SEQUENCE DESCRIPTION: SEQ ID NO:59:

Leu Asp Pro Lys Lys Lys Arg Lys Val Leu Glu
1               5                       10

(2) INFORMATION FOR SEQ ID NO:60:

(i) SEQUENCE CHARACTERISTICS:
        (A) LENGTH: 27 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: misc_feature
        (B) LOCATION: 1..5
        (D) OTHER INFORMATION: /note= "Xho I restriction site overhang."

(ix) FEATURE:
        (A) NAME/KEY: misc_feature
        (B) LOCATION: 5..27
        (D) OTHER INFORMATION: /note= "Complementary to SEQ ID NO:58, bases 5 to 27."

(xi) SEQUENCE DESCRIPTION: SEQ ID NO:60:

TCGAGTACCT TTCTCTTCTT CTTAGGG                                        27

(2) INFORMATION FOR SEQ ID NO:61:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

CGACAGTCGA CGCCCCCCCG ACCGATGTC                                      29

(2) INFORMATION FOR SEQ ID NO:62:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

CGACACTCGA GCCCACCGTA CTCGTC                                         26

(2) INFORMATION FOR SEQ ID NO:63:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 6..11
        (D) OTHER INFORMATION: /note= "Sal I restriction site."

(ix) FEATURE:
        (A) NAME/KEY: CDS
        (B) LOCATION: 12..29

( i x ) FEATURE:
        ( A ) NAME/KEY: misc_feature
        ( B ) LOCATION: 12..29
        ( D ) OTHER INFORMATION: /note= "Region encoding N-terminal end of VP16 (413-490)."

( x i ) SEQUENCE DESCRIPTION: SEQ ID NO:63:

```
CGACAGTCGA C GCC  CCC  CCG  ACC  GAT  GTC                    29
             Ala  Pro  Pro  Thr  Asp  Val
             1                   5
```

( 2 ) INFORMATION FOR SEQ ID NO:64:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:64:

```
Ala  Pro  Pro  Thr  Asp  Val
1                   5
```

( 2 ) INFORMATION FOR SEQ ID NO:65:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..15

( i x ) FEATURE:
        ( A ) NAME/KEY: misc_feature
        ( B ) LOCATION: 1..15
        ( D ) OTHER INFORMATION: /note= "Region encoding C-terminal end of VP16 (413-490)."

( x i ) SEQUENCE DESCRIPTION: SEQ ID NO:65:

```
GAC  GAG  TAC  GGT  GGG  CTCGAGTGTC  G                       26
Asp  Glu  Tyr  Gly  Gly
1                   5
```

( 2 ) INFORMATION FOR SEQ ID NO:66:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:66:

```
Asp  Glu  Tyr  Gly  Gly
1                   5
```